US005773243A

United States Patent [19]
Fritzinger et al.

[11] Patent Number: 5,773,243
[45] Date of Patent: Jun. 30, 1998

[54] COBRA PRO CVF1

[75] Inventors: David C. Fritzinger, Alexandria, Va.; Reinhard Bredehorst; Carl-Wilhelm Vogel, both of Hamburg, Germany

[73] Assignee: Georgetown University, Washington, D.C.

[21] Appl. No.: 447,411

[22] Filed: May 23, 1995

Related U.S. Application Data

[63] Continuation of Ser. No. 43,747, Apr. 7, 1993, abandoned.

[51] Int. Cl.[6] .............................. C12P 21/02; C07K 14/46

[52] U.S. Cl. ........................................... 435/69.1; 530/350

[58] Field of Search .................................... 435/212, 69.1, 435/320.1, 252.3; 530/350, 380; 536/23.5

[56] References Cited

U.S. PATENT DOCUMENTS

| | | | |
|---|---|---|---|
| 4,289,690 | 9/1981 | Pestka et al. | 530/351 |
| 4,727,028 | 2/1988 | Santerro et al. | 435/240.2 |

OTHER PUBLICATIONS

Fritzinger, D.C. et al. (1992) "Complete sequence of two different cobra venom factor cDNAs" *Faseb J.* 6(4):A1453.
Alberts, B. et al. (1989) *Molecular Biology of the Cell*, Garland Publ., New York, pp. 265–266.

Vogel, C.–W. (1991) *Handbook of Natural Toxins* (Tu, A.T. ed.), vol. 5, Marcel Dekker, New York, pp. 147–188.

O'Keefe, M.C. et al. (1988) "A novel cleavage product of human complement component C3 with structural and functional properties of cobra venom factor" *J. Biol. Chem.* 263(25):12690–12697.

E. Teicher et al, *Immunochemistry*, (1973), 10, pp. 265–271, "The Role of Specific Amino Acid Residues in the Antigenic Reactivity of the Loop Peptide of Lysozyme".

R. Arnon et al, *Proc. Nat. Acad. Sci. USA*, (1971), 68, pp. 1450–1455, "Antibodies Reactive with Native Lysozyme Elicited by a Completely Synthetic Antigen".

D. C. Fritzinger et al, *Proc. Nat. Acad. Sci. USA*(1994), 91, pp. 12775–12779, "Molecular Cloning and Derived Primary Structure of Cobra Venom Factor".

C.–W. Vogel et al, *Journal of Immunological Methods*, (1984), 73, pp. 203–220, "Cobra Venom Factor: Improved Method for Purification and Biochemical Characterization".

D. C. Fritzinger et al, "Complete Structure of Cobra Complement Component C3 mRNA", Abstract, 15th International Congress of Biochemistry, Jerusalem, Israel, Aug. 4–8, 1991.

Poster Material (9 sheets) Presented at Cambridge, England, Sep. 1991 and at Anaheim, California, on Tuesday Apr. 7, 1992. See Fritzinger et al, *Complement and Inflation*, (1991), 8, p. 152 and Fritzinger et al, *FASEB Journal*, (1992), 4, p. A1903; both already of record for published Abstracts.

Beuhelman et al. 1987. J. Immunol. Methods 97:119–122.

Mierendorf et al. 1987 Methods in Enzymology 152:458–469.

Weir et al. (eds.). 1986 *Handbook of Experimental Immunology: vol. 1: Immunochemistry*, Boston, MA, pp. 39.34–39.49.

Petrella et al. 1989. Complement Inflammation 6:386–387.

Fritzinger et al. (abstract, Pecilog File 155 accession No. 93056528) 1992, J. Immunol. 149(11):3554–3562.

*Primary Examiner*—Robert A. Wax
*Assistant Examiner*—Kawai Lau
*Attorney, Agent, or Firm*—Oblon, Spivak, McClelland, Maier & Neustadt, P.C.

[57] ABSTRACT

DNA sequences encoding cobra C3, CVF1, and CVF2, as well as plasmids and transformed hosts comprising such DNA sequences, are provided.

3 Claims, 29 Drawing Sheets

```
       M  E  G  M  A  L  Y  L  V  A  A  L  L  I  G  F  P  G  S  S  H  G  A  L  Y  T  L       5
  1  GGACTACCATGGAGGGGATGGCTCTCTATCTGGTGGCTGCTGCTCTATTGATTGGTTTTCCAGGGTCTTCCCAGGGGCTCTCTATACCCTC   89

I  T  P  A  V  L  R  T  D  T  E  E  Q  I  L  V  E  A  H  G  D  S  T  P  K  S  L  D  I  F      35
 90  ATCACCCCTGCTGTTTTGCGAACAGAGACACAGAAGAGCAAATTTTGGTGGAGGCCCATGGAGACAGTACTCCAAAATCGCTTGACATCTTT  179

V  H  D  F  P  R  K  Q  K  T  L  F  Q  S  R  V  D  M  N  Q  A  G  S  M  F  V  T  P  T  I      65
180  GTTCATGATTTTCCACGGAAGCAGAAAACCTTGTTCCAAAGCAGAGTAGATATGAATCAGGCAGGAAGCATGTTTGTCACTCCAACTATA   269

K  V  P  A  K  E  L  N  K  D  S  K  Q  N  Q  Y  V  V  V  K  V  T  G  P  Q  V  A  L  E  K      95
270  AAGGTTCCTGCAAAAGAACTGAATAAGGACTCCAAGCAAAATCAGTATGTGGTTGTGAAAGTAACTGGTCCTCAAGTGGCATTGGAAAAG   359

V  V  L  L  S  Y  Q  S  G  F  V  F  I  Q  T  D  K  G  I  Y  T  P  G  S  P  V  R  Y  R  V     125
360  GTGGTTCTCCTTTCTTACCAGAGTGGCTTTGTGTTCATCCAGACAGATAAAGGCATCTATACACCAGGCTCTCCAGTGCGTTATCGTGTC   449

F  S  V  D  H  N  M  H  R  M  D  K  T  V  I  V  E  F  Q  T  P  E  G  I  V  V  S  S  K  P     155
450  TTTTCTGTGGATCACAACATGCACAGGATGGACAAAACTGTGATTGTGGAGTTCAGACTCCAGAAGGCATTGTTGTCAGTTCTAAACCA   539

V  N  P  S  G  S  I  R  P  Y  N  L  P  E  L  V  S  F  G  T  W  K  A  V  A  K  Y  E  H  S     185
540  GTCAATCCATCAGGCTCGATCCGGCCTTACAATTTACCAGAGCTTGTCAGTTTTGGGACATGGAAGGCTGTGGCCAAATATGAACATTCA   629

P  E  E  S  Y  T  A  Y  F  D  V  R  E  Y  V  L  P  S  F  E  V  R  L  Q  P  S  D  K  F  L     215
630  CCAGAAGAGAGCTACACTGCATATTTTGATGTCAGAGAATATGTGTTACCAAGCTTTGAAGTTCGTCTGCAACCATCAGATAAGTTTCTT  719

Y  I  D  G  N  K  N  F  H  V  S  I  T  A  R  Y  L  Y  G  K  K  V  E  G  V  A  F  V  V  F     245
720  TACATTGATGGGAATAAAAATTTCCACGTGTCTATCACTGCAAGGTACTTATATGGAAAGAAAGTGGAAGGTGTGGCCTTTGTCGTCTTT  809

G  V  K  I  D  D  A  K  K  S  I  P  D  S  L  T  R  I  P  I  I  D  G  D  E  A  T  L  K     275
810  GGAGTCAAAATAGATGATGCTAAAAAGAGTATTCCAGACTCACTCACGAGAATTCCGATTATTGATGGAGATGGGAAGCAACACTAAAA   899
```

FIG. 2A

```
276  R   D   T   L   R   S   R   F   Q   D   L   N   Q   L   V   G   H   T   L   Y   V   S   V   T   V   I   T   E   S   G       305
900  AGAGATACACTACGTTCCGATTTCAAGATCTCAATCAGCTTGTTGGTCATATACTTGTATGTATCTGTAACAGTGATAACAGAATCAGGC    989

306  S   D   M   V   V   T   E   Q   G   G   I   H   I   V   T   S   P   Y   Q   I   Y   F   T   K   T   P   K   Y   F   K       335
990  AGTGATATGGTAGTGACTGAGCAAGGCGGCATTCATATTGTGACATCTCCTATCAGATCTACTTCACAAAAACCCCAAATATTCAAG      1079

336  P   G   M   P   Y   E   L   T   V   Y   V   T   N   P   D   G   S   P   A   A   H   V   P   V   V   S   E   A   I   H       365
1080 CCAGGAATGCCATATGAACTGACGGTGTATGTTACCAACCCTGATGGCTCACCAGCTGCCCATGTGCCAGTGGTATCAGAGGCCATTCAT    1169

366  S   E   G   T   T   L   S   D   G   T   A   K   L   I   L   N   T   P   L   N   I   Q   S   L   P   I   T   V   R   I       395
1170 TCTGAGGGAACCACTTTGAGTGATGGAACTGCTAAGCTCATTCTGAACACACTGAACATTCAAAGCCTACCGATCACTGTTAGAACT      1259

396  N   H   G   D   L   P   R   E   R   Q   A   I   K   S   M   T   A   Y   Q   T   Q   G   G   S   E   N   Y   L              425
1260 AACCATGGAGACCTCCCAAGAGAGAACGGCCAGGCAATAAAGTCCATGACAGCCACAGCCTACCAAACCCAGGAGGGTCTGAAAACTATCTT  1349

426  H   V   A   I   T   S   T   E   I   K   P   G   D   N   L   P   V   N   F   N   V   R   G   N   A   N   S   L   N   Q       455
1350 CATGTAGCCATTACATCTACAGAGATTAAGCCCGGAGATAACCTCCCTGTCAATTTCAATGTGAGGGCAATGCAAATTCACTGAACCAG     1439

456  I   K   Y   F   T   Y   L   I   L   N   K   G   I   F   K   V   G   R   Q   P   R   R   D   G   Q   N   L   V   T          485
1440 ATCAAATATTTCACATACCTCATATTGAATAAAGGGAAGATTTTCAAGGTTGGCAGACAACCAGGAGAGATGGGCAGAATCTGGTGACC      1529

486  M   N   L   H   I   T   P   D   L   I   P   S   F   R   F   V   A   Y   Y   Q   V   G   N   N   E   I   V   A   D   S       515
1530 ATGAATCTGCATATCACTCCAGATCTCATCCCTTCCTTCCGGTTTGTGGCTTACTACCAAGTGGGAAATAACGAAATTGTGGCTGATTCT    1619

516  V   W   V   D   V   K   D   T   C   M   G   T   L   V   V   K   G   A   S   S   R   D   D   R   I   Q   K   P   G   A       545
1620 GTCTGGGTGGATGTGAAGGATACCTGCATGGGAACGTTGGTTGTGAAAGGAGCGTCTTCCAGAGACGATCGAATACAAAAGCCAGGAGCT   1709

546  A   M   K   I   K   L   E   G   D   P   G   A   R   V   G   L   V   A   V   D   K   A   V   Y   V   L   N   D   K   Y       575
1710 GCAATGAAAATCAAATTGGAAGGGGATCCAGGTGCTCGGGTTGGTCTTGTGGCTGTGGACAAAGCAGTATATGTTCTCAATGATAAATAT    1799
```

FIG.2B

```
576  K   I   S   Q   A   K   I   W   D   T   I   E   K   S   D   F   G   C   T   A   G   S   G   Q   N   N   L   G   V   F    605
1800 AAGATTAGCCAAGCTAAGATATGGGACACAATAGAAAAAGAGTGACTTTGGCTGTACAGCTGGCAGTGGCCAGAATAATCTGGGTGTGTTT 1889

606  E   D   A   G   L   A   L   T   T   S   T   N   L   N   T   K   Q   R   S   A   A   K   C   P   Q   P   A   N   R   R    635
1890 GAAGATGCTGGACTGGCTCTGACAACCAGCACTAATCTCAACACCAAACAGAGATCAGCAGCTAAGTGTCCTCAGCCTGCAAATCGGAGG 1979

636  R   R   S   S   V   L   L   L   D   S   K   A   S   K   A   A   Q   F   Q   D   Q   G   L   R   K   C   C   E   D   G    665
1980 CGTCGCAGTTCTGTTTTGCTTGACAGCAAAGCAAGCAAAGGCTCAGGATCAAGGCCTGCGTAAATGCTGTGAAGATGGC 2069

666  M   H   E   N   P   M   G   Y   T   C   E   K   R   A   K   Y   I   Q   E   G   D   A   C   K   A   F   L   E   C         695
2070 ATGCATGAGAACCCCATGGGCTACACTTGTGAAAAGCGTGCAAAATACATCCAGGAGGGAGATGCTTGTAAGGCTGCCTTCCTTGAATGT 2159

696  C   H   Y   I   K   G   I   R   D   E   N   Q   R   E   S   E   L   F   L   A   R   S   D   F   E   D   E   L   F   G    725
2160 TGTCACTACATCAAAGGGATCCGAGATGAAAACCAACGGGAGAGCGAGTTGTTTCTGGCAAGAAGTGATTTTGAAGATGAACTCTTTGGA 2249

726  D   D   N   I   I   S   R   D   F   P   E   S   W   L   W   T   E   E   L   T   G   E   P   N   N   Q   G   I         755
2250 GATGACAACATCATCTCCAGGTCTGATTTTCCCGAGAGTTGGTTGTGGCTAACAGAGGAATTGACCGGGAGCCTAACAATCAAGGGATT 2339

756  S   S   K   T   V   P   F   Y   L   R   D   S   I   T   T   W   E   L   L   A   V   G   L   S   P   T   K   G   I   C    785
2340 TCAAGCAAGACAGTACCTTTTATCTGAGGGATTCCATCACAACCTGGGAGTTGCTGGCTGTGGGCCTTTCACCCACCAAAGGGATCTGT 2429

786  V   A   E   P   Y   E   I   T   V   M   K   D   F   F   I   D   L   R   L   P   Y   S   V   V   K   N   E   Q   V   E    815
2430 GTGGCTGAACCGTATGAAATAACAGTCATGAAAGACTTCTTCATTGATCTTCGACTGCCATATTCAGTAGTAGTGAAGAATGAGCAGGTGGAG 2519

816  I   R   A   I   L   Y   N   Y   A   D   E   D   I   Y   V   R   V   E   L   I   Y   N   P   A   F   C   S   A   S   T    845
2520 ATTCGAGCTATTCTGTACAACTACGCTGACGAGGATATTTATGTGCGAGTGGAACTGATATACAACCCAGCCTTCTGCAGTGCTTCCACA 2609

846  E   G   Q   R   Y   R   Q   Q   F   P   I   K   A   L   S   S   R   A   V   P   F   V   I   V   P   L   E   Q   G   L    875
2610 GAAGGACAAAGATACCGACAGCAGTTCCCAATTAAAGCCCTGTCCTCCAGAGCAGTACCATTTGTGATAGTCCCATTAGAGCAAGGATTG 2699
```

FIG.2C

```
876   H  D  V  E  V  I  A  S  V  R  G  E  L  A  S  D  G  V  R  K  K  L  K  V  V  P  E  G  E  R      905
2700  CATGATGTTGAGGTTATAGCAAGTGTCCGGGGAGAGTTGGCATCAGATGGTGTGAGGAAGAAACTGAAAGTTGTACCTGAAGGGAACGG      2789

906   K  N  I  V  T  I  I  E  L  D  P  S  V  K  G  V  G  G  T  Q  E  L  T  V  I  A  N  K  L  D      935
2790  AAAAATATTGTGACTATTATTGAACTGGACCCAAGTGTAAAAGGAGTTGGTGGAACCCAGGAACTAACGGTCATAGCCAATAAATTAGAT    2879

936   D  K  V  P  D  T  E  V  E  T  R  I  S  V  L  G  D  P  V  A  Q  I  I  E  N  S  I  D  G  S      965
2880  GACAAGGTGCCTGATACAGAAGTTGAGACGAGGATTTCTGTTCTAGGTGACCCTGTGGCTCAGATTATTGAAAACTCAATTGATGGAAGT    2969

966   K  L  N  H  L  I  I  T  P  S  G  C  G  E  Q  N  M  I  T  M  T  P  S  V  I  A  T  Y  Y  L      995
2970  AAACTCAATCATCTCATTATTACTCCTTCGGCTGTGGGGAGCAAAATATGATCACCATGACTCCATCGGTCATTGCCACTACTACTTG     3059

996   D  A  T  G  Q  W  E  N  L  G  V  D  R  R  T  E  A  I  K  Q  I  M  T  G  Y  A  Q  Q  M  V      1025
3060  GACGCAACAGGGCAGTGGGAGAATCTTGGTGTGGATCGCAGGACTGAAGCTATCAAACAGATCATGACTGGTTATGCCCAGCAGATGGTG    3149

1026  Y  K  K  A  D  H  S  Y  A  A  F  T  N  R  A  S  S  S  W  L  T  A  Y  V  K  V  L  A  M          1055
3150  TACAAGAAAGCAGATCATTCCTATGCAGCATTTACAAACCGTGCTAGCAGTTCTTGGCTAACAGCATATGTGGTGAAAGTTCTTAGCCATG   3239

1056  A  S  N  M  V  K  D  I  S  H  E  I  I  C  G  G  V  K  W  L  I  L  N  R  Q  Q  P  D  G  V      1085
3240  GCTTCCAACATGGTAAAAGACATTAGCCATGAGATTATTTGTGGAGGTGTGAAATGGCTCATTCTGAACAGGCAACAACCAGATGGAGTG    3329

1086  F  K  E  N  A  P  V  I  H  G  E  M  L  G  G  T  K  G  A  E  P  E  A  S  L  T  A  F  I  V      1115
3330  TTCAAAGAAAATGCCCCTGTGATCCATGGAGAAATGCTGGGAGGAACTAAAGGTGCTGAACCTGAAGCATCTTTAACAGCATTCATTGTG    3419

1116  T  A  L  L  E  S  R  S  V  C  K  E  Q  I  N  I  L  D  S  S  I  N  K  A  T  D  Y  L  L  K      1145
3420  ACTGCATTATTGGAATCCAGATCAGTCTGCAAAGAACAAATCAATATTCTAGACAGCAGCATCAATAAGGCCACAGATTATTTACTCAAA    3509

1146  K  Y  E  K  L  Q  R  P  Y  T  T  A  L  T  A  Y  A  L  A  A  A  D  R  L  N  D  D  R  V  L      1175
3510  AAGTATGAGAAACTGCAAAGGCCTTACACTACAGCCCTAACAGCCTATGCTTTGGCTGCTGCAGACCGACTCAATGATGACAGGGTACTC    3599
```

FIG.2D

```
1176  M  A  A  S  T  G  R  N  R  W  E  E  Y  N  A  R  T  H  N  I  E  G  T  S  Y  A  L  L  A  L  1205
3600 ATGGCAGCATCAACAGGAAGGAATCGTTGGGAAGAATATAATGCTGCACCCATAATATTGAAGGCACTTCCTATGCCTTGTTGGCCCTG 3689

1206  L  K  M  K  K  F  A  E  V  G  P  V  V  R  W  L  I  D  Q  K  Y  Y  G  G  T  Y  G  Q  T  Q  1235
3690 CTGAAAAATGAAGAAATTTGCTGAGGTCGGTCCTGTAGTCAGATGGCTGATAGATCAGAATATTATGGGGAACATATGGACAAACCCAA 3779

1236  A  T  V  M  V  F  Q  A  L  A  E  Y  E  I  Q  M  P  T  H  Q  D  L  N  L  D  I  S  I  K  L  1265
3780 GCAACAGTTATGGTGTTCAAGCTCTTGCTGAATATGAGATTCAGATGCCTACCCATCAGGACTTAAATTTAGATATTTCTATTAAACTG 3869

1266  P  E  R  E  V  P  E  R  Y  S  I  N  D  R  N  A  V  Q  A  R  T  V  E  T  K  L  N  E  D  F  1295
3870 CCAGAACGAGAAGTACCTGAGAGATACAGCATTAATGATAGAAATGTGTCCAGGCCCGGACAGTAGAGACCAAACTCAACGAAGACTTC 3959

1296  T  V  S  A  S  G  D  G  K  A  T  M  T  I  L  T  V  Y  N  A  Q  L  R  E  D  A  N  V  C  N  1325
3960 ACTGTGTCAGCATCAGGTGATGGAAAAGCAACAATGACCATTTTGACGGTCTATAATGCACAATTGAGGGAGGATGCAAATGTTTGCAAC 4049

1326  K  F  H  L  D  V  S  V  E  N  V  E  L  N  L  K  Q  A  K  G  G  K  A  A  L  R  L  K  I  C  1355
4050 AAATTCCATCTTGATGTTTCTGTTGAAAACGTTGAACTTAAAACAGGCAAAGGAGGCAAGGCAGCCCTCAGGCTTAAAATCTGC 4139

1356  T  R  Y  L  G  E  V  D  S  T  M  T  I  I  D  I  S  M  L  T  G  F  F  P  D  A  E  D  L  K  1385
4140 ACTAGGTATCTGGGAGAAGTGGATTCTACAATGACAATAATTGATATTTCTATGCTGACTGGTTTTTTCCCTGATGCTGAAGACCTTAAA 4229

1386  L  S  N  G  V  D  R  Y  I  S  K  F  E  I  D  N  N  N  A  Q  K  G  T  V  V  I  Y  L  D  K  1415
4230 AGGCTTTCTAACGGAGTGGACAGATACATCTCCAAGTTTGAAATTGACAATAATAATGGCTCAGAAAGGAACTGTTGTCATTTACTTAGAC 4319

1416  R  V  S  H  S  E  D  E  C  L  H  F  K  I  H  K  H  F  E  V  G  F  I  Q  P  G  S  V  K  V  1445
4320 AGGGTCTCCCACTCTGAAGATGAATGCCTGCACTTTAAGATTCACAAGCATTTGAAGTTGGCTTCATTCAGCCAGGATCAGTCAAGGTG 4409

1446  Y  S  Y  Y  N  L  D  E  Q  C  T  K  F  Y  H  P  D  K  E  T  G  L  L  N  K  I  C  H  G  N  1475
4410 TACAGCTACTACAACTAGATGAACAATGTACCAAGTTCTACCATCCAGATAAAGAAACAGGTGTTCTCAATAAGATATGTCATGGTAAC 4499
```

FIG.2E

```
1476  I  C  R  C  A  E  E  T  C  S  L  L  N  Q  Q  K  K  I  D  L  Q  L  R  I  Q  K  A  C  A  Q      1505
4500  ATTGCCGATGTGCAGAAGAAACCTGTTCCTTGCTCAACCAGCAGAAAAGATTGATCTTCAATTACGAATTCAAAAAGCTGCGCGCAA        4589

1506  N  V  D  Y  V  Y  K  T  K  L  L  R  I  E  E  K  D  G  N  D  I  Y  F  M  D  V  L  E  V  I      1535
4590  AATGTGGATTATGTCTACAAAACCAAGCTGCTTCGAATAGAAGAAAAAGATGGTAATGATATCTATTTCATGGATGTTTAGAAGTTATT      4679

1536  K  G  G  T  D  R  N  A  Q  A  K  A  R  Q  Y  V  S  Q  R  K  C  Q  E  A  L  N  L  K  L  D      1565
4680  AAAGGAGGCACTGACCGAAATGCACAAGCAAAAGCCCGCCAGTATGTAAGTCAAAGGAAATGCCAGGAGGCTTTGAATCTGAAGCTGGAT     4769

1566  N  D  Y  L  I  W  G  L  S  S  D  L  W  P  M  K  D  D  I  S  Y  L  I  T  K  N  T  W  I  E      1595
4770  AATGATTATCTGATCTGGGGTCTCAGCAGTGACCTGTGGCCCATGAAAGATGATATCTCTACCTCATTACAAGAACACCTGGATTGAG       4859

1596  R  W  P  N  E  D  E  C  Q  D  E  E  F  Q  N  L  C  D  D  F  A  Q  L  S  N  T  L  T  I  F      1625
4860  AGATGGCCAAATGAAGATGAATGCCAGGATGAAGAATTCCAGAATTTGTGTGATGACTTTGCTCAGTTGTCCAATACACTGACTATTTTT     4949

1626  G  C  P  T                                                                                    1629
4950  GGCTGCCCTACTTAAAAGTTCAGAAGAACAATCAATGATAGGAAGAAATTCTCAGAAGACAGATTTTTGAGCCAATACATATATGTTACTTT  5039

5040  GCCTCTTGATTTTTTTTATCATTTTGCTCTGCGTGTTTCCTTCACAATTGTTTATACAGAAATAAATAATTGATTTCTTA               5129

5130  CTTTGAAAAAATGGAACTCTCTGATTTGGGTTTTCCAGATGTGCCAAAATGACAACTCTAATAAATGACTTGAGGAAAAAAA             5211
```

FIG.2F

|  | 628 | | 642 | % IDENTICAL | % SIMILAR |
|---|---|---|---|---|---|
| COBRA | CPQPAN | RRRR | SSVLL | | |
| HUMAN | CPQPAA | RRRR | .SVQL | 86 | 86 |
| MOUSE | CTKPAA | RRRR | .SVQL | 71 | 71 |
| RAT | CAKPAA | RRRR | .SVQL | 71 | 79 |

C-TERMINUS OF β-CHAIN     N-TERMINUS OF α-CHAIN

*FIG. 5*

|  | 714 | 727 | % IDENTICAL | % SIMILAR |
|---|---|---|---|---|
| COBRA | LAR | SDFEDELFGDD | | |
| HUMAN | LAR | SNLEDEIIAEE | 50 | 100 |
| MOUSE | LAR | SELEEDIIPGG | 29 | 93 |
| RAT | LAR | SDVDEDIIPEE | 29 | 86 |

C3 CONVERTASE CLEAVAGE SITE

*FIG. 6*

|        | 970                        995 | % IDENTICAL | % SIMILAR |
|--------|--------------------------------|-------------|-----------|
| COBRA  | LIITPSGCGEQNMITMTPSVIATYYL     |             |           |
| HUMAN  | LIVTPSGCGEQNMIGMTPTVIAYHYL     | 81          | 85        |
| MOUSE  | LIVTPSGCGEQNMIGMTPTVIAVHYL     | 81          | 85        |
| RAT    | LIVTPSGCGEQNMIGMTPTVIAVHYL     | 81          | 85        |
| RABBIT | LIVTGSGCGEQNMIAMTHTVIAVHYL     | 73          | 77        |

*FIG. 7*

|        | 720     729 | % IDENTICAL | % SIMILAR |
|--------|-------------|-------------|-----------|
| COBRA  | EDELFGDDNI  |             |           |
| HUMAN  | DEDIIAEENI  | 20          | 100       |
| MOUSE  | EEDIIPEEDI  | 20          | 100       |
| RAT    | DEDIIPEEDI  | 10          | 100       |

*FIG. 8*

|  | 1390 | 1420 | % IDENTICAL | % SIMILAR |
|---|---|---|---|---|
| COBRA | VDRYISKFEIDNNMAQKGTVVIYLDKVSHS | | | |
| HUMAN | VDRYISKYELDKAFSDRNTLIIYLDKVSHS | | 63 | 87 |
| MOUSE | VDRYISKYEMNKAFSNKNTLIIYLEKISHT | | 53 | 80 |
| RAT | VDRYISKYEMDKAFSNKNTLIIYLEKISHS | | 63 | 83 |
| RABBIT | VDRYISKYELNKAFSNKNTLIIYLDKISHS | | 60 | 83 |
| XENOPUS | VDKYISKYEVNKGANDKGTLILYLDKVSHI | | 57 | 83 |

*FIG. 10*

|  | 696 | 716 | % IDENTICAL | % SIMILAR |
|---|---|---|---|---|
| COBRA | CHYIKGIRDENQRESELFLAR | | | |
| HUMAN | CNYITELRRQHARASHLGLAR | | 48 | 71 |
| MOUSE | CNHITKLREQHRRDHVLGLAR | | 38 | 67 |
| RAT | CNYITKLREQHRRDHVLGLAR | | 43 | 71 |

*FIG. 11*

|  | 1349 | 1369 | % IDENTICAL | % SIMILAR |
|---|---|---|---|---|
| COBRA | ALRLKICTRYLGEVDSTMTII | | | |
| HUMAN | TMILEICTRYRGDQDATMSIL | | 52 | 67 |
| MOUSE | TMFLEICTKYLGDVDATMSIL | | 57 | 76 |
| RAT | SMILDICTRYLGDVDATMSIL | | 62 | 76 |
| RABBIT | TMILGHCTRYLGDEDATMSIL | | 52 | 67 |
| XENOPUS | TVSIEACARHLKNVDATMSII | | 43 | 57 |

*FIG. 12*

|  | 714 | 723 | % IDENTICAL | % SIMILAR |
|---|---|---|---|---|
| CVF1 | EDGFIADSDI | | | |
| COBRA C3 | EDELFGDDNI | | 40 | 90 |
| HUMAN C3 | DEDIIAEENI | | 30 | 90 |

*FIG. 15*

|  | 1382 | 1411 | % IDENTICAL | % SIMILAR |
|---|---|---|---|---|
| CVF1 | VDRYISRYEVDNNMAQKVAVIIYLNKVSHS | | | |
| COBRA C3 | VDRYISKFEIDNNMAQKGTVVIYLDKVSHS | | 77 | 93 |
| HUMAN C3 | VDRYISKYELDKAFSDRNTLIIYLDKVSHS | | 60 | 83 |

```
                                                                          -1 |+1  N-terminus or α-chain
               Signal Sequence                                          A   L   Y   T   L   I   T      7
     M  E  R  M  A  L  Y  L  V  A  A  L  L  I  G  F  P  G  S  S  H  G|
-22  CCCATGGAGAGGATGGCTCTCTACCTCGTGGCTGCCCTGCTCATTGGTTTTCCAGGGTCTTCTCATGGGCTCTCTACACCCTCATCACC        90

P  A  V  L  R  T  D  T  E  E  Q  I  L  V  E  A  H  G  D  S  T  P  K  Q  L  D  I  F  V  H       37
  8  CCTGCTGTTTTGGGAACAGACACAGAAGAACAGCAAATTTTGGTGGAGGCCCATGGAGACAGTACTCCAAAACAGCTTGACATCTTTGTTCAT    180
 91

D  F  P  R  K  Q  K  T  L  F  Q  T  R  V  D  M  N  P  A  G  G  M  L  V  T  P  T  I  E  I       67
 38  GATTTTCCACGGAAGCAGAAGACACTGTTCCAAACCAGAGTAGATATGAATCCAGCAGGAGGCATGCTTGTCACTCCAACTATAGAATT         270
181

P  A  K  E  V  S  T  D  S  R  Q  N  Q  Y  V  V  V  Q  V  T  G  P  Q  V  R  L  E  K  V  V       97
 68  CCAGCAAAGAAGTGAGTACGGACTCCAGGCAAAATCAATATGTGGTTGTGCAAGTAACTGGTCCTCAAGTGAGATTGGAAAAGGTGGTT         360
271

L  L  S  Y  Q  S  S  F  L  F  I  Q  T  D  K  G  I  Y  T  P  G  S  P  V  L  Y  R  V  F  S      127
 98  CTCCTTTCTTACCAGAGTAGCTTTCTGTTTATCCAGACAGATAAAGGCATCTATACACCAGGGTCTCCAGTACTCTATCGTGTTTTTCT        450
361
                                                            CHO   CHO

M  D  H  N  T  S  K  M  N  K  T  V  I  V  E  F  Q  T  P  E  G  I  L  V  S  S  N  S  V  D      157
128  ATGGATCACAACACAAGCAAGATGAACAAGACAGTGATTGTTGAGTTTCAGACTCCAGAAGGCATTCTTGTCAGTTCTAATTCAGTTGAC        540
451                                                                                          CHO

L  N  F  F  W  P  Y  N  L  P  D  L  V  S  L  G  T  W  R  I  V  A  K  Y  E  H  S  P  E  N      187
158  CTAAACTTCTTCTGGCCTTACAATTTACCAGACCTTGTCAGTTTGGGGACTTGGAGGATTGTGGCCAAATATGAACATTCCCCAGAGAAT        630
541

Y  T  A  Y  F  D  V  R  K  Y  V  L  P  S  F  E  V  R  L  Q  P  S  E  K  F  F  Y  I  D  G      217
188  TATACTGCATATTTTGATGTCAGGAAATATGTTCTGCCAAGCTTTGAAGTCCGTCTGCAACCATCAGAGAAGTTTTTTTACATTGACGGC       720
631

N  E  N  F  H  V  S  I  T  A  R  Y  L  Y  G  E  E  V  E  G  V  A  F  V  L  F  G  V  K  I      247
218  AATGAAAATTTCCACGTGTCTATCACTGCAAGGTACTTGTATGGAGAGGAAGTGGAAGGTGTGGCCTTTGTCCTCTTTGGAGTGAAAATA       810
721

D  D  A  K  K  S  I  P  D  S  L  T  R  I  P  I  I  D  G  D  G  K  A  T  L  K  R  D  T  F      277
248  GATGATGCTAAAAAGAGTATTCCAGACTCACTCACGAGAATTCCGATTATTGATGGAGATGGGAAAGCAACACTAAAAAGAGATACATTC       900
811
```

FIG.14B

```
278  R  S  R  F  P  N  L  N  E  L  V  G  H  T  L  Y  A  S  V  T  V  M  T  E  S  G  S  D  M  V    307
901  CGTTCTCGATTTCCAAATCTCAATGAGCTTGTTGGCCATACTCTGTATGCATCTGTAACAGTCATGACAGAATCAGGCAGTGATATGGTA  990

308  V  T  E  Q  S  G  I  H  I  V  A  S  P  Y  Q  I  H  F  T  K  T  P  K  Y  F  K  P  G  M  P    337
991  GTGACTGAGCAAAGCGGCATTCATATTGTGGCATCTCCCTATCAGATCCACTTCACAAAACCCCAAATATTCAAGCCAGGAATGCCA    1080

338  Y  E  L  T  V  Y  V  T  N  P  D  G  S  P  A  A  H  V  P  V  V  S  E  A  K  H  S  M  G  T    367
1081 TATGAACTGACGGTGTATGTTACCAACCCTGATGGCTCACCAGCTGCCCATGTGCCAGTGGTATCAGAGGCCTTTCATTCTATGGAACC  1170

368  T  L  S  D  G  T  A  K  L  I  L  N  I  P  L  N  A  Q  S  L  P  I  T  V  R  T  N  H  G  D    397
1171 ACTTTGAGTGATGGAACTGCTAAGCTCATCCTGAACATACCACTGAATGCTCAAAGCCTACCAATCACTGTTAGAACTAACCATGGAGAC  1260

398  L  P  R  E  R  Q  A  T  K  S  M  T  A  I  A  Y  Q  T  Q  G  G  S  G  N  Y  L  H  V  A  I    427
1261 CTCCCAAGACAGAACCCAGCAACAAAGTCCATGACAGCTATTGCTTACCAAACCCAGGAGGATCTGGAAACTATCTTCATGTAGCCATT  1350

428  T  S  T  E  I  K  P  G  D  N  L  P  V  N  F  N  V  K  G  N  A  N  S  L  K  Q  I  K  Y  F    457
1351 ACATCTACAGAGATTAAGCCCGGAGATAACTTACCTGTCAATTTCAATGTGAAGGGCAATGCCAATTCACTGAAGCAGATCAAATATTTC  1440

458  T  Y  L  I  L  N  K  G  K  I  F  K  V  G  R  Q  P  R  R  D  G  Q  N  L  V  T  M  N  L  H    487
1441 ACATACCTCATATTGAATAAAGGGAAGATTTTCAAGGTTGGCAGGCAACCCAGGAGAGATGGGCAGAATCTGGTGACCATGAATCTGCAT  1530

488  I  T  P  D  L  I  P  S  F  R  F  V  A  Y  Y  Q  V  G  N  N  E  I  V  A  D  S  V  W  V  D    517
1531 ATCACTCCAGATCTCATCCCTTCCTTCCGGTTTGTGGCTTACTACCAAGTGGGAAACAACGAAATTGTGGCTGATTCTGTCTGGGTGGAT  1620

518  V  K  D  T  C  M  G  T  L  V  V  K  G  D  N  L  I  Q  M  P  G  A  A  M  K  I  K  L  E  G    547
1621 GTGAAGGATACCTGCATGGAACCTGGTTGTTGTGAAAGGAGACAATCTAATACAAATGCCAGGAGCTGCAATGAAAATCAAATTGGAAGGC  1710

548  D  P  G  A  R  V  G  L  V  A  V  D  K  A  V  Y  V  L  N  D  K  Y  K  I  S  Q  A  K  I  W    577
1711 GATCCAGGTGCTCGGGTTGGTCTTGTGGCCTGTGGACAAAGCAGTATATGTTCTCAATGATAAAGATTAGCCAAGCTAAGATATGG     1800
```

```
 878  V Q E A L W S D G V R K K L K V V P E G V Q K S I V T I V K              907
2701  GTCCAGGAAGCGTTGTGTGGTCAGACGGTGTGAGGAAGAAACTGAAAGTTGTACCTGAAGGGTACAGAAATCCATTGTGACTATTGTTAAA  2790

908  L D P R A K G V G G T Q L E V I K A R K L D D R V P D T E I              937
2791  CTGGACCCAAGGGCAAAAGGAGTTGGTGGAACACAGCTAGAAGTGATCAAAGCCCGAAAATTAGATGACAGAGTGCCTGACACAGAAATT  2880

938  E T K I I Q G D P V A Q I I E N S I D G S K L N H L I I T                967
2881  GAAACCAAGATTATCATCCAAGGTGACCCTGTGGCTCAGATTATTGAAAACTCAATGATGAAGTAAACTCAACCATCTCATTATCACT    2970
                                              Thioester Site 968  P S G G E Q N M I R M A A P V I A T Y Y L D T T E Q W E T                997
2971  CCTTCTGGCTGTGGGGAGCAAAATATGATCCGCATGGCCGCACCAGTTATTGCCACCTACTACCTGGACACCACAGAGCAGTGGGAGACT  3060

998  L G I N R R T E A V N Q I V T G Y A Q Q M V Y K A D H S Y                1027
3061  CTCGGCATAAATCGCAGGACTGAAGCTGTCAATCAGATCGTGACTGGTTATGCCCAGCAGATGGTGTACAAGAAAGCAGATCATTCCTAT  3150

1028  A A F T N R A S S W L T A Y V V K V F A M A A K M V A G I                1057
3151  GCAGCATTTACAAACCGTGCATCTAGTTGGCTTACGGCCTATGTCGTAAAAGTCTTTGCCATGGCTGCCAAAATGGTAGCAGGCATT    3240

1058  S H E I I C G G V R W L I L N R Q Q P D G A F K E N A P V L                1087
3241  AGTCATGAAATCATTTGTGGAGGTGTGAGGTGGCTGATTCTGAACAGGCAACAGCCAGATGGAGCCTTCAAAGAAAATGCCCCTGTACTT  3330

1088  S G T M Q Q G I Q G A E E V Y L T A F I L V A L L E S K T                1117
3331  TCTGGAACAATGCAGCAGGGAATTCAAGGTGCTGAAGAAGTATATTTAACAGCTTTCATTCTGGTTGCCTTGTTGGAATCCAAAACA    3420

1118  I C N D Y V N S L D S S I K K A T N Y L L K K Y E K L Q R P                1147
3421  ATCTGCAATGACTATGTCAATAGTCTAGACAGCAGCATCAAGAAGGCCACAAATTATTTACTCAAAAAGTATGAGAAACTGCAAAGGCCT  3510
                                                       Factor H binding site (1)

1148  Y T T A L T A Y A L A A A D Q L N D D R V L M A A S T G R D              1177
3511  TACACTACAGCCCTCACAGCCTATGCTTTGGCTGCAGCAGATCAATGATGACAGGGTACTCATGGCAGCATCAACAGGAAGGGAT      3600
```

FIG. 14E

```
                    CB2 binding site (?)          Factor H binding site (2)
1207    H W E E Y N A H  T H N I E G  T  S Y A L L A L L K M K K F D Q
3690    CATTGGGAAGAATACAATGCTCACACCCACAACATTGAAGGCACTTCCTATGCCTTGTTGCCCTTGCTGAAAATGAAGAAATTTGATCAA 1237       C P I V R W L T D Q N F Y G E T Y G Q T O A T V  M A F Q A
3780    ACTGGTCCCATAGTCAGATCAGACAGATCAGACAGAATTTTATGGGGAAACATATGGACAAACAGTTATGGCATTTCAAGCT
        N-terminus of β-chain
1267    L A E Y E I Q M P T H K D L N L D I T I E L P D R E V P I R
3870    CTTGCTGAATATGAGATTCAGATGCCTACCCATAAGGACTTAAACTTAGATATTACTATTGAACTGCCAGATCGAGAAGTACCTATAAGG 1297    Y R I N Y E N A L L A R T V E T K L N Q D I T V T A S G D G
3960    TACAGAATTAATTATGAAAATGCTCTCCTGGCTCGGACAGTAGAGACAGAGACCAAACTCAACCAAGACACATCACTGTGACAGCATCAGGTGATGGA
                                                                              CHO
1327    K A T M T I L T F Y N A Q L Q E K A N V C N K F H L N V S V
4050    AAACCAACAATGACCATTTTGACATTCTATAACGCACAGTTGCAGGAGAAGGCCAAATGTTTGCAATAAATTCATCTTAATGTTTCTGTT 1357    E N I H L N A M G A K G A L M L K I C T R Y L G E V D S T M
4140    GAAAACATCCACTTGAATGCCAATGGGAGCCAAGGGAGCCCTCATGCTCAAGATCTGCACAAGGTATCTGGAGAAGTTGATTCTACAATG 1387    T I I D I S M L T G F L P D A E D L T R L S K G  V D R Y I S
4230    ACAATAATTGATATTTCTATGCTGACTGGTTTCTCCCTGATGCTGAAGACCTTACAAGGCTTTCTAAAGGAGTGGACAGATACATCTCC
                              Properdin binding site
1417    E D E C L H
4320    AGATATGAAGTTGACAATATGCTCAGAAAGTAGCTGTATCATTTACTTAAACAAGGTCTCCCACTCTGAAGATGAATGCCTGCAC 1447    F K I L K H F E V G F I Q P G S V K V Y S Y Y N L D E K C T
4410    TTTAAGATTCTCAAGCATTTTGAAGTTGGCTTCATTCAGCCAGGATCAGTCAAGGTGTACAGCTACTACAATCTAGATGAAAAATGTACC 1477    K F Y H P D K G T G L L N K I C I G N V C R C A G E T C S S
4500    AAGTTCTACCATCCAGATAAAGGAACAGGCCTTCTCAATAAGATATGTATTGGTAACGTTTGCCGATGTGCAGGAGAAACCTGTTCCTCG
```

```
1478  L   N   H   Q   E   R   I   D   V   P   L   Q   I   E   K   A   C   E   T   N   V   D   Y   V   Y   K   T   L   L      1507
4501  CTCAACCATCACGAAGGATTGATGTTCCATTACAAATTGAAAAAGCCTGCGAGACGAATGTGGATTATGTCACAAACCAAGCTGCTT                                    4590

1508  R   I   E   E   Q   D   G   N   D   I   Y   V   M   D   V   L   E   V   I   K   Q   G   T   D   E   N   P   R   A   K  1537
4591  CGAATAGAAGAACAAGATGGTAATGATATCTATGTCATGGATGTTTTAGAAGTTATTAAACAAGTACTGACGAAAATCCACGAGCAAAG                                    4680

1538  T   N   Q   Y   I   S   Q   R   K   C   Q   E   A   L   N   L   K   V   N   D   D   Y   L   I   W   G   S   R   S   D  1567
4681  ACCCACCAGTACATAAGTCAAAGGAAATGCCAGGAGCCTCTGAATCTGAAGGTGAATGATGATTATCTGATCTGGGGTTCCAGGAGTGAC                                    4770

1568  L   L   P   T   K   D   K   I   S   Y   I   I   T   K   N   T   W   I   E   R   W   P   H   E   D   E   C   Q   E   E  1597
4771  CTGTTGCCCACGAAAGATAAAATTTCCTACATCATTACAAAGAACACATGGATTGAGAGATGGCCACATGAAGACGAATGTCAGGAAGAA                                    4860

1598  E   F   Q   K   L   C   D   D   F   A   Q   F   S   Y   L   T   E   F   G   C   P   T                                     1620
                                                                      |C-terminus of β-chain|
4861  GAATTCCAAAAGTTGTGTGATGACTTTGCCCAGTTTAGCTACCTGACTGAGTTTGGCTGCCCTACTTAAAAGTTCAGAAGAATCAAT                                      4950

4951  GATAGGGAAGAAATTCTCAGAAGACAGATTTTTGACCAATGCATATATGTTACTTTGCCCTCTGATCTTTTAGTTTTATGTCAATTTGC                                    5040

5041  TCTGTTATTTCCCTTAAATGTTTATACATAAAATAATAATCGATTTCTTACTTTGATATGTTCTTGATTTTTAATAAACAATGGTGA                                      5130

5131  TTCATGATTATTTTTTCTCTTCTGATCCATCCAATATTTGAAGTGCTCTGAACAGAGCACTTATGGAGTAATGTTTAGTGATGGATC                                      5220

5221  AATAAGTTGGTGAGTCAATATTATCAGGCCCTATATACTCTTATGGAAGATCGATTTGTACCCAAAGAAACATAGATTGAAATGTGTAC                                    5310

5311  TTTGAAAACAGAGGTTTCAGTGTTGTATATGTTTTACACTGGATACAATCTTAACTCTTAATAAACACTGATCTCAGAACATTAACAGCTG                                   5400
```

```
5401 TTATTTAATAATGACAAATATCTTTGACTGCACCCACACAGAAAACATTGCATTACATTAGAATGGCTTTTATCAGATGACTAAGTCTGC  5490
5491 TAGACTTGCCATCTGTCAAAATGTGCCTCTTCCCCAGCTCCAACTTTAAGGATAGTAACTAATAGATGTTCTCTCATTGGCTCCTGACAG  5580
5581 ACGTGTGGTAGCCACTGAGTTCCCTGGATGACACTAGAAGCTGGCAGCACACTGCAGCCTGGTGGAGGGGCCTCTTTTGCTATCCCATG   5670
5671 AGCTTCTATTCATCCTCTTATCTGTTGGGATGGGACGTCTCTGATTTCCAGGTATACAGGTGATCTCATTTACTAACATCACC          5760
5761 ACTAACTTCAAGGATTGGTTGAGGGGTTATGCCAATGTGATTGAAGGTTTCACCCATGTGAATCTATTCTCCAATCCCAATGCTGTATCT  5850
5851 ATGCTGCTCATTTCTGCTTGTAAAAATGGTATAAAAAGAATAAACACTGCCCAGGCAGTCAGACATCGGAATTC                  5924
```

|           | 964                         | 989 | % IDENTICAL | % SIMILAR |
|-----------|-----------------------------|-----|-------------|-----------|
| CVF1      | LIITPSGCGEQNMIRMAAPVIATYYL  |     |             |           |
| COBRA C3  | LIITPSGCGEQNMITMTPSVIATYYL  |     | 85          | 88        |
| HUMAN C3  | LIVTPSGCGEQNMIGMTPTVIAVHYL  |     | 73          | 81        |

*FIG. 17*

|           | 708           | 721 | % IDENTICAL | % SIMILAR |
|-----------|---------------|-----|-------------|-----------|
| CVF1      | LARDDNEDGFIADS |    |             |           |
| COBRA C3  | LARSDFEDELFGDD |    | 50          | 79        |
| HUMAN C3  | LARSNLDEDIIAEE |    | 36          | 79        |

N-TERMINUS OF CVF1 γ-CHAIN
(C3 CONVERTASE CLEAVAGE SITE)

*FIG. 18*

```
            1                        15
CVF1      | .ALYTLITPAVLRTDT |
COBRA C3  | .ALYTLITPAVLRTDT |
HUMAN C3   SPMYSIITPNILRLES
MOUSE C3   IPMYSIITPNVLRLES
```

*FIG. 21A*

```
           1242                              1264
CVF1      | EIQMPTHKDLNLDITIELPDREV |
COBRA C3  | EIQMPTHQDLNLDISIKLPEREV |
HUMAN C3    QKDAPDHQELNLDVSLQLPSRSS
MOUSE C3    QTDVPDHKDLNMDVSFHLPSRSS
```

*FIG. 21B*

```
           711                         732
CVF1      | DDNEDGFIADSDIISRSDFPKS |
COBRA C3    SDFEDELFGDDNIISRSDFPES
HUMAN C3    SNLDEDIIAEENIVSRSEFPES
MOUSE C3    SELEEDIIPEEDIISRSHFPQS
```

*FIG. 21C*

```
     I  P  S  G  G  D  M  V  M  T  E  Q  S  G  I  H  I  V  T  S  P  Y  Q  I  Y  F  T  K  T
   1 GAATTCCATCAGGAGGTGATATGGTAATGACTGAGCAAAGTGGCATTCATATTGTGACATCTCCTATCAGATCTACTTCACAAAACC    89
     P  K  Y  F  K  P  G  M  P  Y  E  L  T  V  V  T  K  P  D  G  S  P  A  A  H  V  P  V  V
  90 CCCAAATATTTCAAGCCAGGAATGCCATATGAACTGACGGTGTATGTTACCAAACCTGATGGCTCACCAGCTGCCCATGTGCCAGTGGTA   179
     S  E  A  I  H  S  E  G  T  T  L  S  D  G  T  A  K  L  F  L  N  T  P  Q  N  A  Q  S  L  P
 180 TCAGAGGCCATTCATTCTGAGGGAACCACTTTGAGTGATGGAACTGCTAAGCTCTTCCTGAACACACCACAAAATGCTCAAAGCCTACCG   269
     I  T  V  R  T  N  H  G  D  L  P  R  E  R  Q  A  I  K  S  M  T  A  T  A  Y  Q  T  Q  G  G
 270 ATCACTGTTAGAACTAACCATGGAGACCTCCCAAGAGAACGCCAGGCAATAAAGTCCATGACAGCCACAGCCTACCAAACCCAGGGAGGA   359
     S  G  N  Y  L  H  V  A  I  T  S  T  E  I  K  P  G  D  N  L  P  V  N  F  N  V  R  G  N  A
 360 TCTGGAAACTATCTTCATGTAGCCATTACATCTACAGAGATTAAGCCCGGAGATAACTTACCTGTCAATTTCAATGTGAGGGCAATGCA   449
     N  S  L  N  Q  I  K  Y  F  T  Y  L  I  L  N  K  G  K  I  F  K  V  G  R  Q  H  R  G  D  G
 450 AATTCACTGAACCAGATACAAATATTTCACATACCTCACATCTGAATAAAGGGAAGATTTTCAAGGTTGGCAGGCAACACAGGGAGATGGG   539
     N  L  V  T  M  N  L  H  I  T  P  D  L  I  P  S  F  R  F  V  A  Y  Y  Q  V  G  N  N  E  I
 540 GAGAATCTGGTGACCATGAATCTACATATCACTCCAGATCTCATTCCTTCCTTCCGGTTTGTGGCTTACTACCAAGTGGGAAACAATGAA   629
     E  V  A  D  S  V  W  V  D  V  K  D  T  C  M  G  T  L  V  V  K  G  A  T  S  R  D  N  R  I
 630 ATTGTGGCTGATTCTGTCTGGGTGGATGTGAAGGATACCTGCATGGGAACGTTGGTTGTGAAAGGAGCGACTTCCAGAGACAATCGAATA   719
     Q  M  P  G  A  A  M  K  I  K  L  E  G  D  P  G  A  W  I  G  L  V  A  V  D  K  A  E  Y  V
 720 CAAATGCCAGGAGCTGCAATGAAAATCAAATTGGAAGGGGATCCAGGTGCTGTGGATTGGTCTTGTGGCTGTGGACAAAGCAGAATATGTT   809
     L  N  D  K  Y  K  I  S  Q  A  K  I  W  D  T  I  E  K  S  D  F  G  C  T  A  G  S  G  Q  N
 810 CTCAATGATAAATATAAGATTAGCCAAGCTAAGATATGGGACACAATAGAAAAGAGTGACTTTGGCTGTACAGCTGGCAGTGGCCAGAAT   899
     P  A  N  R  R  R  R  S  S  V  L  L  D  S  N  A  S  K  A  A  Q  F  Q  D  D  L  R  K
 900 CCTGCAAATCGGAGGCGTCGCAGTTCTGTTCTGTTTGCTGCTGACAGCAATGCCAGCAAAGCGGCACAGTTTCAGGATCAAGACCTGTAAA  989
     C  E  D  G  M  H  E  N  P  M  G  H  T  C  E  K  R  E  K  Y  I  Q  E  G  D  A  C  K  A
 990 CCTGCAAATCGGAGGCGTCGCAGTTCTGTTCTGTTTGCTGCTGACAGCAATGCCAGCAAAGCGGCACAGTTTCAGGATCAAGACCTGTAAA 1079
1080 TGCTGTGAAGATGGCATGCATGAGAACCCCATGGGGCACACTTGTGAAAAGCGTGAAAAATACATCCAGGAGGGAGATGCTTGTAAGGCT 1169
```

FIG.22A

```
        A  F  L  E  C  C  H  Y  I  K  G  I  Q  D  D  N  K  R  E  S  E  L  F  L  A  R  S  D  F  E
1170 GCCTTCCTGAATGCTGTCACTACATCAAGGGATCCAAGATGACAATAAACGGAGAGCGAGTTGTTTCTGGCAAGAAGTGATTTTGAA 1259
        D  D  L  F  G  E  G  N  I  T  S  R  S  D  F  P  E  S  W  L  W  L  M  E  Q  L  S  E  H  P
1260 GATGATTTATTTGGAGAAGGTAACATCACCTCAAGGTCTGATTTTCCTGAGAGTTGGTTGTGGCTAATGGAGCAGTTGCTGAACATCCT 1349
        N  S  K  G  I  S  S  K  I  V  P  F  Y  L  R  D  S  I  T  T  W  E  L  L  A  V  G  L  S  P
1350 AACAGTAAAGGGATTTCAAGCAAGATAGTACCTTTTTATCTCAGGGATTCCATCACAACCTGGGAGTTGCTGGTGTGGCCTTTCACCC 1439
        T  K  G  I  C  V  A  E  P  Y  E  I  T  V  M  K  D  F  F  I  D  L  Q  L  P  Y  S  V  V  K
1440 ACCAAAGGGATCTGTGTGGCTGAACCTTATGAAACAGTCATGAAAGACTTCTTCATTGATCTTCAACTGCCGTATTCAGTAGTGAAG 1529
        N  E  Q  V  K  I  R  A  V  L  Y  N  Y  A  D  K  D  I  Y  V  R  V  E  L  L  Y  S  P  A  F
1530 AATGAGCAGGTGAAAATTCGAGCTGTGTTTTGTACAACTACGGTGACAAGGATATATTTGTACGAGTGGAACTGTTATACAGCCCAGCCTTC 1619
        C  S  A  S  T  E  S  Q  R  Y  R  E  Q  L  P  I  K  A  L  S  S  R  A  V  S  F  V  I  V  P
1620 TGCAGTGCTTCCACAGAGAGTCAAAGATACCGAGAGCAGTTGCCAATTAAAGCCCTGTCCTCCAGGGCAGTATCGTTTGTGATAGTCCCA 1709
        L  E  Q  G  L  H  D  V  E  V  T  A  S  V  Q  G  E  L  M  S  D  G  V  K  K  L  K  V  V
1710 TTAGAGCAAGGATTGCATGATGTTGAGGTTACAGCAAGTGTCCAGGGAGAGTTGATGTCAGATGGTGTGAAGAAGAAACTGAAAGTTGTA 1799
        P  E  G  E  W  K  S  I  V  T  I  I  E  L  D  P  H  T  K  G  I  G  G  T  Q  V  E  L  V  K
1800 CCTGAAGGGGAATGGAAAAGTATTGTTACTATTATTGAACTGGACCCACACACAAAGGAATTGGTGGAACAGGTAGAATTGGTCAAA 1889
        A  N  K  L  N  D  R  V  P  D  T  E  I  E  T  K  I  T  I  Q  G  D  P  V  A  Q  T  I  E  N
1890 GCCAATAAATTAAATGACAGGGTTCCTGATACGGAAATAGAAACCAAGATTACTATTCAAGGTGATCCTGTGGCTCAGACTATTGAAAAC 1979
        S  I  D  G  S  K  L  N  H  L  I  T  P  F  G  C  G  E  Q  N  M  I  R  M  T  A  P  V  I
1980 TCAATTGATGGAAGTAAACTCAACCATCTCATTACTCCTTTTGGCTGTGGGGAGCAAAATATGATCCGCATGACTGCACCAGTTATT 2069
        A  T  Y  Y  L  D  T  T  Q  Q  W  E  T  L  G  I  N  R  R  T  E  A  V  N  Q  I  M  T  G  Y
2070 GCCACCTACTACCTGGACACCACACAGCAGTGGGAGACTCTCGGCATAAATCGCAGGACTGAAGCTGTCAATCAGATCATGACTGGTTAT 2159
        A  Q  L  V  Y  K  K  A  D  H  S  Y  A  A  F  T  N  S  A  S  S  S  W  L  T  A  Y  V  V
2160 GCCCAGCTTGGTGTACAAGAAAAGCAGACCATTCCTATGCAGCATTTACAACAGTGCATCTTGGCTAACAGCATATGTTGTA 2249
        K  I  F  A  L  A  A  K  I  V  K  D  I  N  H  E  I  V  C  G  G  M  R  W  L  I  L  N  R  Q
2250 AAAATCTTTGCCTTGGCTGCCAAAATTGTAAAAGACATTAACCATGAAATCGTTTGTGGAGGTATGAGGTGGCTGATTCTGAACAGGCAA 2339
        R  T  D  G  V  F  R  E  N  A  P  V  L  F  G  T  M  Q  G  G  I  Q  G  A  E  P  E  G  S  L
2340 CGAACAGATGGAGTGTTCAGAGAGAATGCCCCTGTACTTTTTGGAACAATGCAAGGAGGCATTCAAGGTGCTGAACCAGAAGGATCTTTA 2429
```

COBRA PRO CVF1

This application is a Continuation of application Ser. No. 08/043,747, filed on Apr. 7,1993, now abandoned.

BACKGROUND OF THE INVENTION

1. Field of the Invention

The present invention relates to DNA encoding cobra C3, CVF1, and CVF2, plasmids comprising such DNA, and microorganisms transformed with such a plasmid.

2. Discussion of the Background

The third component of complement, C3, plays a pivotal role in both the classical and alternative pathways of complement activation, and many of the physiologic C3 activation products have important functions in the immune response and host defense (Müller-Eberhard, H. J. 1988. Molecular organization and function of the complement system. *Annu. Rev. Biochem.* 57:321). In the alternative pathway, the activated form of C3, C3b, is a structural subunit of the C3 convertase. This bimolecular enzyme consists of C3b and Bb, the activated form of factor B. This enzyme is formed by the binding of C3b to factor B that is subsequently cleaved by factor D, resulting in the formation of the C3 convertase, C3b,Bb, and the release of the activation peptide Ba. The C3 convertase activates C3 by cleaving the molecule into C3b and the anaphylatoxin, C3a. The C3b molecule will bind in close proximity to the C3 convertase. Eventually, the bound C3b will allow for the activation of C5 into C5b and the anaphylatoxin, C5a. C5 activation occurs by the same C3b,Bb enzyme that can cleave C5 when it is bound to an additional C3b molecule. The C5-cleaving enzyme is called C5 convertase. It is a trimolecular complex composed of $(C3b)_2$,Bb. Inasmuch as the activation of both C3 and C5 occurs at the identical active site in the Bb subunit, the enzyme is also called C3/C5 convertase; and only one EC number has been assigned (EC 3.4.21.47).

Cobra venom contains a structural and functional analog of C3 called Cobra Venom Factor (CVF). This molecule can bind factor B in human and mammalian serum to form the complex, CVF,B (Hensley, P. M., C. O'Keefe, C. J. Spangler, J. C. Osborne, Jr. and C.-W. Vogel. 1986. The effects of metal ions and temperature on the interaction of cobra venom factor and human complement factor B. *J. Biol. Chem.* 261:11038), which is also cleaved by factor D into the bimolecular enzyme CVF,Bb and Ba (Vogel. C.-W., and H. J. Müller-Eberhard. 1982. The cobra venom factor-dependent C3 convertase of human complement. A kinetic and thermodynamic analysis of a protease acting on its natural high molecular weight substrate. *J. Biol. Chem.* 257:8292). The bimolecular complex CVF,Bb is a C3/C5 convertase that activates C3 and C5 analogously to the C3/C5 convertase formed with C3b (Vogel, C.-W. 1991. Cobra venom factor, the complement-activating protein of cobra venom. In *Handbook of Natural Toxins, Vol. 5, Reptile and Amphibian Venoms*. A. T. Tu, ed. Marcel Dekker, New York, p. 147). Although the two C3/C5 convertases C3b,Bb and CVF,Bb share the molecular architecture, the active site-bearing Bb subunit, and the substrate specificity, the two enzymes exhibit significant functional differences. The CVF, Bb enzyme is physicochemically far more stable than C3b, Bb (Vogel. C.-W., and H. J. Müller-Eberhard. 1982. The cobra venom factor-dependent C3 convertase of human complement. A kinetic and thermodynamic analysis of a protease acting on its natural high molecular weight substrate. *J. Biol. Chem.* 257:8292; Medicus, R. G., O. Gotze, and H. J. Müller-Eberhard. 1976. Alternative pathway of complement: recruitment of precursor properdin by the labile C3/C5 convertase and the potentiation of the pathway. *J. Exp. Med.* 144:1076), it is resistant to inactivation by the regulatory proteins factors H and 1 (Lachmann, P. J. and A. Halbwachs. 1975. The influence of C3b inactivator (KAF) concentration on the ability of serum to support complement activation. *Clin. Exp. Immunol.* 21:109; Nagaki, K., K. Iida, M. Okubo, and S. Inai. 1978. Reaction mechanisms of β-1H globulin. *Int. Arch. Allergy Appl. Immunol.* 57:221), it exhibits different kinetic properties (Vogel. C.-W., and H. J. Müller-Eberhard. 1982. The cobra venom factor-dependent C3 convertase of human complement. A kinetic and thermodynamic analysis of a protease acting on its natural high molecular weight substrate. *J. Biol. Chem.* 257:8292; Pangburn, M. K., and H. J. Müller-Eberhard. 1986. The C3 convertase of the alternative pathway of human complement. *Biochem J.* 235:723), and it does not require additional C3b for C5 cleavage (Miyama, A., T. Kato, S. Horai, J. Yokoo, and S. Kashiba. 1975. Trypsin-activated complex of human Factor B with cobra venom factor (CVF), cleaving C3 and C5 and generating a lyctic factor for unsensitized guinea pig erythrocytes. I. Generation of the activated complex. *Biken J.* 18:193; Von Zabern, I. B. Hinsch, H. Przyklenk, G. Schmidt, and W. Vogt. 1980. Comparison of Naja n. naja and Naja h. haje cobra venom factors: correlation between binding affinity for the fifth component of complement and mediation of its cleavage. *Immunobiology* 157:499).

CVF and mammalian C3 have been shown to exhibit several structural similarities including immunologic cross-reactivity (Alper, C. A. and D. Balavitch. 1983. Cobra venom factor: evidence for its being altered cobra C3 (the third component of complement. *Science* 191:1275; Eggertsen, G. A., U. Hellman, and J. Sjöquist. 1983. Antigenic relationships between human and cobra complement factors C3 and cobra venom factor (CVF) from Indian cobra (Naja naja). *J. Immunol.* 131:1920; Vogel, C.-W., C. A. Smith, and H. J. Müller-Eberhard. 1984. Cobra venom factor: structural homology with the third component of human complement. *J. Immunol.* 133:3235; Grier, A. H., M. Schultz, and C.-W.. Vogel. 1987. Cobra venom factor and human C3 share carbohydrate antigenic determinants. *J. Immunol.* 139:1245), amino acid composition (Vogel, C.-W., C. A. Smith, and H. J. Müller-Eberhard. 1984. Cobra venom factor: structural homology with the third component of human complement. *J. Immunol.* 133:3235; Vogel, C.-W.., and M. K. Pangburn. 1985. An improved statistical method for quantitation of similarities of amino acid compositions reveals homologies among complement proteins. *Complement* 2:81), circular dichroism spectra, and secondary structure (Vogel, C.-W.., C. A. Smith, and H. J. Müller-Eberhard. 1984. Cobra venom factor: structural homology with the third component of human complement. *J. Immunol.* 133:3235), electron microscopic ultrastructure (Vogel, C.-W.., C. A. Smith, and H. J. Müller-Eberhard. 1984. Cobra venom factor: structural homology with the third component of human complement. *J. Immunol.* 133:3235; Smith, C. A., C.-W.. Vogel, and H. J. Müller-Eberhard. 1982. Ultra-structure of cobra venom factor-dependent C3/C5 convertase and its zymogen. Factor B of human complement. *J. Biol. Chem.* 257:9879; Smith, C. A., C.-W.. Vogel, and H. J. Müller-Eberhard. 1984. MHC class III products: an electron microscopic study of the C3 convertases of human complement. *J. Exp. Med.* 159:324), and amino-terminal amino acid sequence (Vogel, C.-W.., C. A. Smith, and H. J. Müller-Eberhard. 1984. Cobra venom factor: structural homology with the third component of human complement. *J. Immunol.* 133:3235; Lundwall, A., U. Hellman, G. Eggertsen, and J. Sjöquist. 1984. Chemical characterization of cyanogen bromide fragments from the β-chain of human complement factor C3. *FEBS Lett.* 169:57). Nevertheless, significant structural differences exist between the two molecules. Whereas C3 is a two-chain molecule with an apparent molecular mass, dependent on the species, of 170 to 190 kDa (Eggertsen, G. A., U. Hellman, and J. Sjöquist. 1983. Antigenic relationships between human and cobra complement factors C3 and cobra venom factor (CVF) from Indian cobra (Naja naja). *J. Immunol.* 131:1920; DeBruijn, M. H. L., and G. H. Fey. 1985. Human complement component C3: cDNA coding sequence and derived primary structure. *Proc. Natl. Acad. Sci. USA* 82:708; Alsenz, J., D. Avila, H. P. Huemer, I. Esparza, J. D. Becherer, T. Kinoshita, Y. Wang, S. Oppermann, and J. D. Lambris. 1992. Phylogeny of the third component of complement C3: analysis of the conservation of human CR1, CR2, H, and B binding sites, ConA binding sites, and thioester bond in the C3 from different species. *Dev. Comp. Immunol.* 16:63; Vogel, C.-W.., and H. J. M üller-Eberhard. 1984. Biochemical characterization of the third component of the cobra complement system. *Dev. Comp. Immunol.* 8:239), CVF is a three-chain molecule with an apparent molecular mass of 136 kDa (Vogel, C.-W.., and H. J. Müller-Eberhard. 1984. Cobra venom factor: improved method for purification and biochemical characterization. *J. Immunol. Methods* 73:203) that resembles C3c, one of the physiologic activation products of C3 (Vogel, C.-W.. 1991. Cobra venom factor, the complement-activating protein of cobra venom. In *Handbook of Natural Toxins, Vol. 5, Reptile and Amphibian Venoms*. A. T. Tu, ed. Marcel Dekker, New York, p. 147; Vogel, C.-W.., C. A. Smith, and H. J. M üller-Eberhard. 1984. Cobra venom factor: structural homology with the third component of human complement. *J. Immunol.* 133:3235). Another significant structural difference between C3 and CVF lies in their glycosylation, CVF has a 7.4% (w/w) carbohydrate content consisting mainly of N-linked complex-type chains with unusual α-galactosyl residues at the non-reducing termini (Vogel, C.-W.., and H. J. Müller-Eberhard. 1984. Cobra venom factor: improved method for purification and biochemical characterization. *J. Immunol. Methods* 73:203; Gowda, D. C., M. Schultz, R. Bredehorst, and C.-W.. vogel. 1992. Structure of the major oligosaccharide of cobra venom factor. *Mol. Immunol.* 29:335). In contrast, human and rat C3 exhibit a lower extent of glycosylation with different structures of their oligosaccharide chains (Hase, S., N. Kikuchi, T. Ikenaka, and K. Inoue. 1985. Structures of sugar chains of the third component of human complement. *J. Biochem.* 98:863; Hirani, S., J. D. Lambris, and H. J. Müller-Eberhard. 1986. Structural analysis of the asparagine-linked oligosacchardies of human complement component C3. *Biochem. J.* 233:613; Miki, K., S. Ogata, Y. Misumi, and Y. Ikehara. 1986. Carbohydrate structures of the third component of rat complement. *Biochem J.* 240:691).

The multifunctionality of the C3 protein, which interacts specifically with more than 10 different plasma proteins or cell surface receptors, has spurred significant interest in a detailed structure/function analysis of the molecule. For some ligands of C3 the binding sites have been assigned to more or less defined regions of the C3 polypeptide including factor H (Ganu, V. S., and H. J. Müller-Eberhard. 1985. Inhibition of factor B and Factor H binding to C3b by synthetic peptide corresponding to residues 749–789 of human C3. *Complement* 2:27), properdin (Daoudaki, M. E., J. D. Becherer, and J. D. Lambris. 1988. A 34-amino acid peptide of the third component of complement mediates properdin binding. *J. Immunol.* 140:1577; Farries, T. C., T. Seya, R. A. Harrison, and J. P. Atkinson. 1990. Competition for binding sites on C3b by CR1, CR2, MCP, factor B, and factor H. *Complement Inflamm.* 7:30), factor B (Fishelson, Z. 1981. Complement C3: a molecular mosaic of binding sites. *Mol. Immunol.* 28:545), and the complement receptors CR1 (Becherer, J. D., and J. D. Lambris. 1988. Identification of the C3b receptor-binding domain in the third component of complement. *J. Biol. Chem.* 263:14586), CR2 (Lambris, J. D., V. S. Ganu, S. Hirani, and H. J. Müller-Eberhard. 1985. Mapping of the C3d receptor (CR2-binding site) and a neoantigenic site in the C3d domain of the third component C3 α-chain. *Proc. Natl. Acad. Sci. USA* 82:4235; Becherer, J. D., J. Alsenz, and J. D. Lambris. 1989. Molecular aspects of C3 interactions and structural/functional analysis of C3 from different species. *Curr. Top. Microbiol. Immunol.* 153:45), and CR3 (Becherer, J. D., J. Alsenz, and J. D. Lambris. 1989. Molecular aspects of C3 interactions and structural/functional analysis of C3 from different species. *Curr. Top. Microbiol. Immunol.* 153:45; Wright, S. D., P. A. Reddy, M. T. C. Jong, and B. W. Erickson, 1987. C3bi receptor (complement receptor type 3) recognizes a region of complement protein C3 containing the sequence Arg-Gly-Asp. *Proc. Natl. Acad. Sci. USA* 84:1965; Taniguchi-Sidle, A., and D. E. Isenman. 1992. Mutagenesis of the Arg-Gly-Asp (RGD) triplet of human complement component C3 does not abolish binding of iC3b to the leukocyte integrin complement receptor type III (CR3, CD11B/CD18). *J. Biol. Chem.* 267:635). The elucidation of structural differences between C3 and CVF, two closely related molecules that share some properties (e.g., formation of a C3/C5 convertase) but differ in others (e.g., susceptibility to regulation by factors H and I) can be expected to help identify functionally important regions of the C3 molecule.

The inventors have recently discovered that CVF actually exists in two forms, CVF1 and CVF2. It is desirable to obtain large quantities of cobra C3, CVF1, and CVF2 for a number of reasons. However, the isolation of large quantities of the peptides from cobras is problematic to say the least. Thus, it is desirable to clone the genes which encode cobra C3, CVF1, and CVF2.

SUMMARY OF THE INVENTION

Accordingly, one object of this invention is to provide a novel sequence of DNA which encodes cobra C3.

It is another object of the present invention to provide a novel sequence of DNA which encodes CVF1.

It is another object of the present invention to provide a novel sequence of DNA which encodes CVF2.

It is another object of the present invention to provide a plasmid which comprises a sequence of DNA which encodes cobra C3.

It is another object of the present invention to provide a plasmid which comprises a sequence of DNA which encodes CVF1.

It is another object of the present invention to provide a plasmid which comprises a sequence of DNA which encodes CVF2.

It is another object of the present invention to provide a microorganism which has been transformed with a plasmid comprising a sequence of DNA which encodes cobra C3.

It is another object of the present invention to provide a microorganism which has been transformed with a plasmid comprising a sequence of DNA which encodes CVF1.

It is another object of the present invention to provide a microorganism which has been transformed with a plasmid comprising a sequence of DNA which encodes CVF2.

It is another object of the present invention to provide a method for producing large quantities of cobra C3.

It is another object of the present invention to provide a method for producing large quantities of CVF1.

It is another object of the present invention to provide a method for producing large quantities of CVF2.

These and other objects, which will become apparent during the following detailed description, have been achieved by the inventors' cloning of the genes which encode cobra C3, CVF1, and CVF2.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 shows the cDNA (SEQ ID NO:1) and derived amino acid sequence (SEQ ID NO:2) of cobra C3. The $NH_2$- and C-termini of the α- and β-chains, functionally important regions, and known ligand binding sites are indicated. Amino acid residue numbering starts at the $NH_2$-terminus of the pro-C3 molecule ($NH_2$-terminus of the mature β-chain);

FIG. 5 provides a comparison of C3 sequences (SEQ ID NOS:3–6) at the junction of the α- and β-chain. Comparisons were made with a sequence analysis program (Devereux, J. R., P. Haeberli, and O. A. Smithies. 1984. Comprehensive set of sequence analysis programs for the VAX. Nucleic Acids Res. 12:387). Identical amino acid residues are boxed and shaded whereas conservative replacements are shaded only. Amino acid residue numbering is based on the cobra C3 sequence as shown in FIG. 2. The percent sequence identity and similarity with the cobra sequence is shown on the right. The C-terminus of the β-chain and the $NH_2$-terminus of the α-chain are indicated demonstrating the highly conserved sequence of four arginine residues in the pre-pro-C3 proteins in all species;

FIG. 6 provides a comparison of C3 sequences (SEQ ID NO:7–10) at the convertase cleavage site. Comparisons were made with a sequence analysis program (Devereux, J. R., P. Haeberli, and O. A. Smithies. 1984. Comprehensive set of sequence analysis programs for the VAX. Nucleic Acids Res. 12:387). Identical amino acid residues are boxed and shaded whereas conservative replacements are shaded only. Amino acid residue numbering is based on the cobra C3 sequence as shown in FIG. 2. The percent sequence identity and similarity with the cobra sequence is shown on the right. The C3 convertase cleavage site is indicated;

FIG. 7 provides a comparison of C3 sequences (SEQ ID NOS:11–14) at the thioester site. Comparisons were made with a sequence analysis program (Devereux, J. R., P. Haeberli, and O. A. Smithies. 1984. Comprehensive set of sequence analysis programs for the VAX. Nucleic Acids Res. 12:387). Identical amino acid residues are boxed and shaded whereas conservative replacements are shaded only. Amino acid residue numbering is based on the cobra C3 sequence as shown in FIG. 2. The percent sequence identity and similarity with the cobra sequence is shown on the right. The cysteine and glutamine residues involved in the intramolecular thioester are identified by asterisks;

FIG. 8 provides a comparison of C3 sequences (SEQ ID NO:15–18) at the factor B binding site. Comparisons were made with a sequence analysis program (Devereux, J. R., P. Haeberli, and O. A. Smithies. 1984. Comprehensive set of sequence analysis programs for the VAX. Nucleic Acids Res. 12:387). Identical amino acid residues are boxed and shaded whereas conservative replacements are shaded only. Amino acid residue numbering is based on the cobra C3 sequence as shown in FIG. 2. The percent sequence identity and similarity with the cobra sequence is shown on the right;

FIG. 10 provides a comparison of C3 sequences (SEQ ID NOS:28–33) at the properdin binding site. Comparisons were made with a sequence analysis program (Devereux, J. R., P. Haeberli, and O. A. Smithies. 1984. Comprehensive set of sequence analysis programs for the VAX. Nucleic Acids Res. 12:387). Identical amino acid residues are boxed and shaded whereas conservative replacements are shaded only. Amino acid residue numbering is based on the cobra C3 sequence as shown in FIG. 2. The percent sequence identity and similarity with the cobra sequence is shown on the right;

FIG. 11 provides a comparison of sequences (SEQ ID NOS:34–37) required for active C3a peptide. Comparisons were made with a sequence analysis program (Devereux, J. R., P. Haeberli, and O. A. Smithies. 1984. Comprehensive set of sequence analysis programs for the VAX. Nucleic Acids Res. 12:387). Identical amino acid residues are boxed and shaded whereas conservative replacements are shaded only. Amino acid residue numbering is based on the cobra C3 sequence as shown in FIG. 2. The percent sequence identity and similarity with the cobra sequence is shown on the right;

FIG. 12 provides a comparison of C3 sequences at the disputed CR3 binding site. Comparisons were made with a sequence analysis program (Devereux, J. R., P. Haeberli, and O. A. Smithies. 1984. Comprehensive set of sequence analysis programs for the VAX. *Nucleic Acids Res.* 12:387). Identical amino acid residues are boxed and shaded whereas conservative replacements are shaded only. Amino acid residue numbering is based on the cobra C3 sequence as shown in FIG. 2. The percent sequence identity and similarity with the cobra sequence is shown on the right;

FIG. 14 shows the cDNA (SEQ ID NO:44) and derived amino acid sequence (SEQ ID NO:45) of CVF1. The $NH_2$- and C-termini of the α-, γ-, and β-chains, functionally important regions, and known ligand binding sites are indicated. Amino acid residue numbering starts at the $NH_2$-terminus of the pro-CVF1 molecule;

FIG. 15 provides a comparison of CVF1 and C3 sequences (SEQ ID NOS:46–48) at the factor B binding site. Comparisons were made with a sequence analysis program (Devereux, J. R., P. Haeberli, and O. A. Smithies. 1984. Comprehensive set of sequence analysis programs for the VAX. *Nucleic Acids Res.* 12:387). Identical amino acid residues are boxed and shaded whereas conservative replacements are shaded only. Amino acid residue numbering is based on the CVF1 sequence as shown in FIG. 14. The percent sequence identity and similarity with the CVF1 sequence is shown on the right;

FIG. 16 provides a comparison of CVF1 and C3 sequences (SEQ ID NOS:49–51) at the properdin binding site. Comparisons were made with a sequence analysis program (Devereux, J. R., P. Haeberli, and O. A. Smithies. 1984. Comprehensive set of sequence analysis programs for the VAX. *Nucleic Acids Res.* 12:387). Identical amino acid residues are boxed and shaded whereas conservative replacements are shaded only. Amino acid residue numbering is based on the CVF1 sequence as shown in FIG. 14. The percent sequence identity and similarity with the CVF1 sequence is shown on the right;

FIG. 17 provides a comparison of CVF1 and C3 sequences (SEQ ID NOS:52–54) at the thioester site. Comparisons were made with a sequence analysis program (Devereux, J. R., P. Haeberli, and O. A. Smithies. 1984. Comprehensive set of sequence analysis programs for the VAX. *Nucleic Acids Res.* 12:387). Identical amino acid residues are boxed and shaded whereas conservative replacements are shaded only. Amino acid residue numbering is based on the CVF1 sequence as shown in FIG. 14. The percent sequence identity and similarity with the CVF1 sequence is shown on the right;

FIG. 18 provides a comparison of C3 sequences (SEQ ID NO:55–57) at the convertase cleavage site with the N-terminus of the γ-chain of CVF1. Comparisons were made with a sequence analysis program (Devereux, J. R., P. Haeberli, and O. A. Smithies. 1984. Comprehensive set of sequence analysis programs for the VAX. *Nucleic Acids Res.* 12:387). Identical amino acid residues are boxed and shaded whereas conservative replacements are shaded only. Amino acid residue numbering is based on the CVF1 sequence as shown in FIG. 14. The percent sequence identity and similarity with the CVF1 sequence is shown on the right;

FIG. 21 provides a comparison of cobra, human, and mouse C3 with: (a) the N-terminal CVF1 α-chain (SEQ ID NOS:64–66); (b) the N-terminal CVF1 β-chain (SEQ ID NOS:67–70); and (c) the N-terminal CVF1 γ-chain (SEQ ID NOS:71–74). Comparisons were made with a sequence analysis program (Devereux, J. R., P. Haeberli, and O. A. Smithies. 1984. Comprehensive set of sequence analysis programs for the VAX. *Nucleic Acids Res.* 12:387). Identical amino acid residues are boxed and shaded whereas conservative replacements are shaded only. Amino acid residue numbering is based on the CVF1 sequence as shown in FIG. 14. The percent sequence identity and similarity with the cobra sequence is shown on the right; and FIG. 22, shows the partial cDNA sequence (SEQ ID NO:75) of CVF2.

DETAILED DESCRIPTION OF THE PREFERRED EMBODIMENTS

Figure 1:
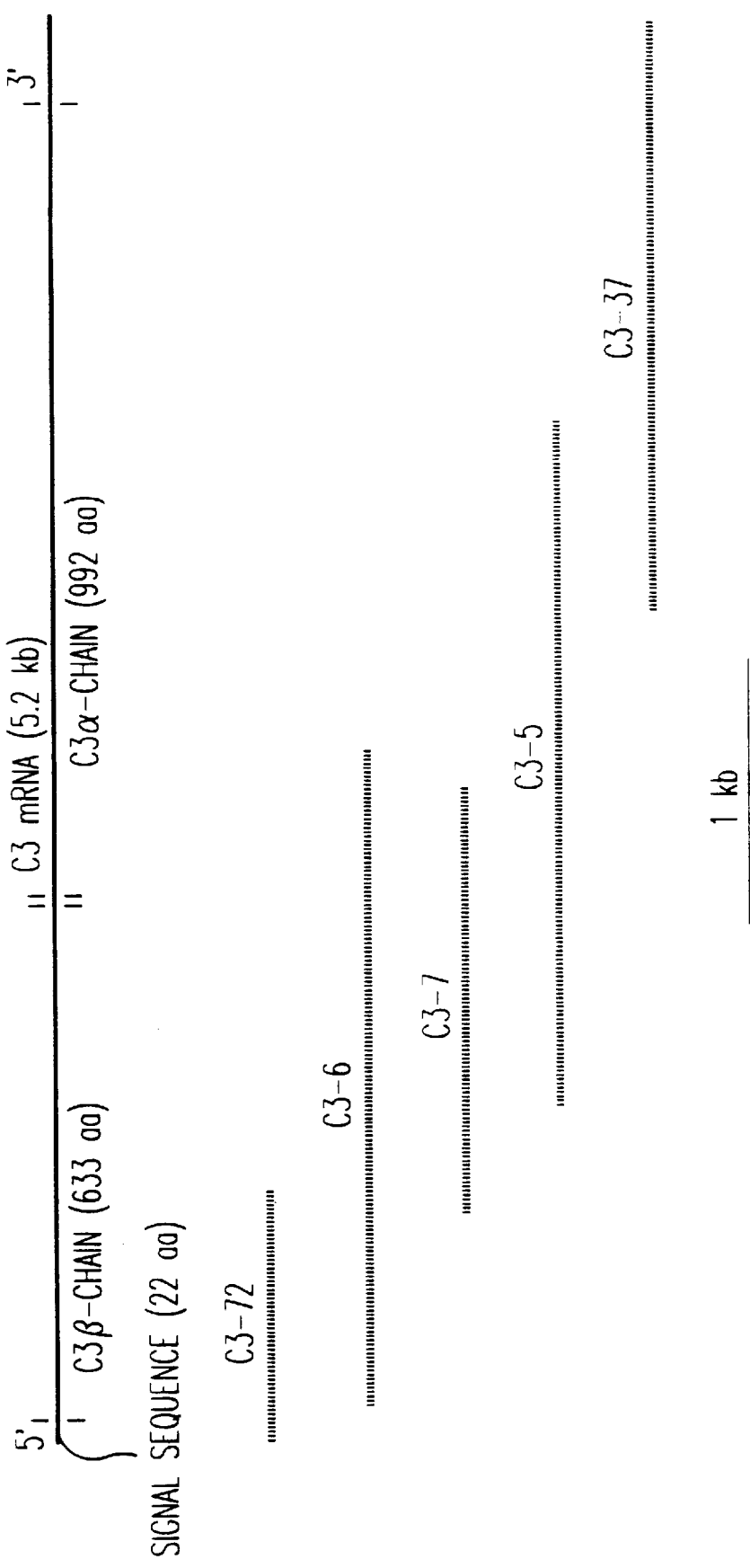
FIG. 1 depicts a map of clones used for the sequencing of cobra C3. The upper portion shows a schematic drawing of cobra C3 mRNA in which the positions and numbers of amino acid residues of the α- and β-chains are indicated. The lower portion shows the relative positions of the five cDNA clones that were used to sequence the molecule.

Thus, in a first embodiment, the present invention relates to DNA encoding cobra C3. Due to the occurrence of CVF in cobra venom, the complement system of cobra has received special attention. The existence of a complement system in cobra resembling the mammalian complement system in its molecular organization has been described (Vogel, C.-W.., and H. J. Muller-Eberhard, 1985. The cobra complement system: I. The alternative pathway of activation, *Dev. Comp. Immunol.* 9:311; Vogel, C. W., and H. J. Müller-Eberhard. 1985. The cobra complement system: II. The membrane attack complex. *Dev. Comp. Immunol.* 9:327). Cobra C3 was first purified from cobra plasma by affinity chromatography on an anti-CVF column, taking advantage of the cross-reaction of some antisera to CVF with cobra C3 (Eggertsen, G. A., U. Hellman, and J. Sjöquist. 1983. Antigenic relationships between human and cobra complement factors C3 and cobra venom factor (CVF) from Indian cobra (Naja naja). T. Immunol. 131:1920; Vogel, C.-W.., and H. J. Müller-Eberhard. 1984. Biochemical characterization of the third component of the cobra complement system. *Dev. Comp. Immunol.* 8:239). More recently, cobra C3 was purified by conventional chromatography (Alsenz, J., D. Avila, H. P. Huemer, I. Esparza, J. D. Becherer, T. Kinoshita, Y. Wang, S. Oppermann, and J. D. Lambris. 1992. Phylogeny of the third component of complement C3: analysis of the conservation of human CR1, CR2, H, and B binding sites, ConA binding sites, and thioester bond in the C3 from different species. *Dev. Comp. Immunol.* 16:63; Petrella, E. C., R. Bredehorst, and C.-W.. Vogel. 1989. Purification of cobra C3: initial characterization and comparison to cobra venom factor. *Complement Inflamm.* 6:386). The molecule has been shown to consist of an α- and β-chain with apparent molecular masses of 106 to 112 kDa (α-chain) and 60 to 68 kDa (β-chain) (Eggertsen, G. A., U. Hellman, and J. Sjöquist. 1983. Antigenic relationships between human and cobra complement factors C3 and cobra venom factor (CVF) from Indian cobra (Naja naja). *J. Immunol.* 131:1920; Alsenz, J., D. Avila, H. P. Huemer, I. Esparza, J. D. Becherer, T. Kinoshita, Y. Wang, S. Oppermann, and J. D. Lambris. 1992. Phylogeny of the third component of complement C3: analysis of the conservation of human CR1, CR2, H, and B binding sites, ConA binding sites, and thioester bond in the C3 from different species. *Dev. Comp. Immunol.* 16:63; Vogel, C.-W.., and H. J. Müller-Eberhard. 1984. Biochemical characterization of the third component of the cobra complement system. *Dev. Comp. Immunol.* 8:239; Petrella, E. C., R. Bredehorst, and C.-W.. Vogel. 1989. Purification of cobra C3: initial characterization and comparison to cobra venom factor. *Complement Inflamm.* 6:386). Cobra C3 has been shown to contain a thioester in its α-chain as is expected for C3 molecules (Alsenz, J., D. Avila, H. P. Huemer, I. Esparza, J. D. Becherer, T. Kinoshita, Y. Wang, S. Oppermann, and J. D. Lambris. 1992. Phylogeny of the third component of complement C3: analysis of the conservation of human CR1, CR2, H, and B binding sites, ConA binding sites, and thioester bond in the C3 from different species. *Dev. Comp. Immunol.* 16:63; Vogel, C.-W.., and H. J. M üller-Eberhard. 1984. Biochemical characterization of the third component of the cobra complement system. *Dev. Comp. Immunol.* 8:239). In contrast to all C3 molecules so far studied, cobra C3 is not glycosylated (Alsenz, J., D. Avila, H. P. Huemer, I. Esparza, J. D. Becherer, T. Kinoshita, Y. Wang, S. Oppermann, and J. D. Lambris. 1992. Phylogeny of the third component of complement C3: analysis of the conservation of human CR1, CR2, H, and B binding sites, ConA binding sites, and thioester bond in the C3 from different species. *Dev. Comp. Immunol.* 16:63; Petrella, E. C., R. Bredehorst, and C.-W.. Vogel. 1989. Purification of cobra C3: initial characterization and comparison to cobra venom factor. *Complement Inflamm.* 6:386).

The present inventors have cloned and sequenced the cDNA for complement component C3 from cobra plasma. There are several lines of evidence that the sequence obtained is the sequence of cobra C3: 1) the initial three cDNA clones were identified in an expression system using a mono-specific antiserum to cobra C3: 2) the derived $NH_2$-terminal sequences of both α- and β-chain match those of the amino acid sequences obtained by protein sequencing (Petrella, E. C., R. Bredehorst, and C.-W.. Vogel. 1989. Purification of cobra C3: initial characterization and comparison to cobra venom factor. *Complement Inflamm.* 6:386); 3) the derived amino acid compositions of cobra C3 and its two chains resemble those obtained by protein hydrolysis (Petrella, E. C., R. Bredehorst, and C.-W.. Vogel. 1989. Purification of cobra C3: initial characterization and comparison to cobra venom factor. *Complement Inflamm.* 6:386); and 4) the derived amino acid sequence shows a high degree of overall homology with that of C3 molecules from other species including highly conserved regions corresponding to known sites of functional importance.

There are several lines of evidence that the obtained sequence represents that of cobra C3 and not of CVF: 1) CVF is not expected to be expressed in cobra liver; 2) the derived amino acid sequence reported here does not match the known stretches of protein sequence of CVF (Eggertsen, G., P. Lind, J. Sjöquist. 1981. Molecular characterization of the complement activating protein in the venom of the Indian cobra (Naja n. siamensis). *Mol. Immunol.* 18:125); and 3) the cDNA sequence reported here differs from the cDNA sequence of CVF (Fritzinger, D. C., R. Bredehorst, and C. W. Vogel. 1992. Complete sequence of two different cobra venom factor cDNAs. *FASEB J.* 6:A2998).

The primary structure of cobra C3 as derived from the sequencing of its cDNA shows a high degree of homology with those of C3 molecules from other species of which human (DeBruijn, M. H. L., and G. H. Fey. 1985. Human complement component C3: cDNA coding sequence and derived primary structure. *Proc. Natl. Acad. Sci. USA* 82:708), mouse (Lundwall, A., R. A. Wetsel, H. Domdey, B. F. Tack, and G. H. Fey. 1984. Structure of murine complement component C3: I. Nucleotide sequence of cloned complementary and genomic DNA coding for the β-chain. *J. Biol. Chem.* 259:13851; Wetsel, R. A., A. Lundwall, F. Davidson, T. Gibson, B. F. Tack, and G. H. Fey. 1984. Structure of murine complement component C3: II. Nucleotide sequence of cloned complementary DNA coding for the α-chain. *J. Biol. Chem.* 259:13857), and rat (Misumi, Y., M. Sohda, and Y. Ikehara. 1990. Nucleotide and deduced amino acid sequence of rat complement C3. *Nucleic Acids Res.* 18:2178) are fully and those of rabbit (Kusano, M., N. H. Choi, M. Tomita, K. I. Mamamoto, S. Migita, T. Sekiya, and S. Nishimura. 1986. Nucleotide sequence of cDNA and derived amino acid sequence of rabbit complement component C3 α-chain. *Immunol. Inv.* 15:365) and *X. laevis* (Grossberger, D., A. Marcuz, L. Du Pasquier, and J. D. Lambris. 1989. Conservation of structural and functional domains in complement component C3 of Xenopus and mammals. *Proc. Natl. Acad. Sci. USA* 86:1323) partially known. One interesting difference is the absence of glycosylation sites consistent with a lack of detectable glycosylation of the protein. The overall structure of C3 molecules throughout the vertebrates seems to be highly conserved. As is the case for mammalian C3, cobra C3 is synthesized as a pre-pro molecule that is subsequently processed into the mature two-chain protein by removing the signal peptide and the four arginine residues between the β- and α-chain. As with human C3, cobra C3 has a 22-amino acid signal sequence and an α-chain of 992 amino acids. The β-chain of cobra C3 with 633 residues is 12 residues shorter than the β-chain of human C3. All 27 cysteine residues are conserved in both molecules indicating a very high degree of similarity in the tertiary structure of the two proteins. With this degree of overall homology between cobra and mammalian C3s, it is not surprising that several of the functional sites of C3 are highly conserved. These include the four arginine residues in the pre-pro-C3 molecule, probably required for proper maturation to yield the secreted C3 molecule, and the thioester site, the unique structure in the α-chain required for alternative pathway activation and covalent binding to target cells. As in other C3 molecules, the glutamic acid residue whose γ-carboxyl group is part of the intramolecular thioester with the cysteine residue is encoded as glutamine that must be converted into the thioester structure by a hitherto unknown process of post-translational modification.

In addition, the C3 convertase cleavage site and several binding sites for known ligands of C3 such as factor B, factor H, and properdin are highly conserved in cobra C3. The sequence homology at these four sites is significantly higher than the overall sequence homology throughout the molecule that strongly suggests that these sites are conserved sites with defined functions. The observation that conserved amino acid sequences are observed at functionally important sites where one or, in the case of the C3 convertase cleavage site, two protein ligands must interact with the molecule is not surprising: because ligands must evolve to match each other changes in these binding sites are less likely to occur.

The overall similarity of cobra C3 to C3s from other species is not surprising, given that the functional and molecular organization of the complement system has remained generally the same throughout the vertebrates. However, not all functions of the mammalian complement system may be present in lower vertebrates, because the system may have undergone a functional diversification throughout phylogeny. Whereas the overall sequence homology of the C3a domain does not exceed the overall homology throughout the molecule, the last five amino acid residues at the C-terminus of the C3a domain may suggest, that an active C3a anaphylatoxin is derived from cobra C3. However, in the case of the CR2 and CR3 binding sites, no sequence homology exceeding that of the overall homology was found. Accordingly, the existence of CR2 and CR3 binding sites on cobra C3 and, therefore, the existence of these two cell surface ligands for C3 activation products on cobra WBC cannot be deduced. However, indirect evidence for the existence of CR2 in reptiles may be derived from the observation, that human CR2 can bind to iC3 from Xenopus, a phylogenetically lower species (Alsenz, J., D. Avila, H. P. Huemer, I. Esparza, J. D. Becherer, T. Kinoshita, Y. Wang, S. Oppermann, and J. D. Lambris. 1992. Phylogeny of the third component of complement C3: analysis of the conservation of human CR1, CR2, H, and B binding sites, ConA binding sites, and thioester bond in the C3 from different species. *Dev. Comp. Immunol.* 16:63). With regard to the CR3 binding site, recent work strongly suggests that the proposed region in the C-terminal portion of the C3 α-chain may not represent the CR3 binding site altogether (Taniguchi-Sidle, A., and D. E. Isenman. 1992. Mutagenesis of the Arg-Gly-Asp (RGD) triplet of human complement component C3 does not abolish binding of iC3b to the leukocyte integrin complement receptor type III (CR3, CD11B/CD18). *J. Biol. Chem.* 267:635). The observed substitutions in cobra C3 in the otherwise highly conserved R(L)GD and DATMSI stretches may actually lend further support to that contention.

In addition to being the first complement protein cloned from a reptile, cobra C3 also represents the first plasma protein cloned from cobra and the third protein from cobra for which cDNA sequence is available. An interesting difference of cobra C3 to mammalian C3s is the codon usage (see Table 1). Whereas the G+C percentage of all known mammalian C3 mRNA is more than 53% (DeBruijn, M. H. L., and G. H. Fey. 1985. Human complement component C3: cDNA coding sequence and derived primary structure. *Proc. Natl. Acad. Sci. USA* 82:708; Lundwall, A., R. A. Wetsel, H. Domdey, B. F. Tack, and G. H. Fey. 1984. Structure of murine complement component C3: I. Nucleotide sequence of cloned complementary and genomic DNA coding for the β-chain. *J. Biol. Chem.* 2591:3851; Wetsel, R. A., A. Lundwall, F. Davidson, T. Gibson, B. F. Tack, and G. H. Fey. 1984. Structure of murine complement component C3: II. Nucleotide sequence of cloned complementary DNA coding for the α-chain. *J. Biol. Chem.* 2591:3857), the G+C percentage of cobra C3 mRNA is significantly lower at 43%. At this point, the significance of this difference is not known. However, it may reflect a different preference for codon usage in the species cobra because the G+C percentage of cobra nerve growth factor (43.6%) and of the cobra acetylcholine receptor (44.2%) resembles that of cobra C3 (Selby, M. J., R. H. Edwards, and W. J. Rutter. 1987. Cobra nerve growth factor; structure and evolutionary comparison. *J. Neurosci. Res.* 18:293; Neumann, D., D. Barchen, M. Horowitz, E. Kochva, and S. Fuchs. 1989. Snake acetylcholine receptor: cloning of the domain containing the four extracellular cysteins of the alpha-subunit. *Proc. Natl. Acad. Sci. USA* 86:7755).

The DNA sequence of the present invention for cobra C3 comprises any DNA sequence that encodes the amino acid sequence of: a) pre-pro-cobra C3, which corresponds to the amino acid sequence of from position about −22 to position about 1629 in FIG. 2; (b) pro-cobra C3, which corresponds to the amino acid sequence of from position about 1 to position about 1629 in FIG. 2; (c) the α-chain of cobra C3, which corresponds to the amino acid sequence of from position about 638 to position about 1629 of FIG. 2; (d) the β-chain of cobra C3, which corresponds to the amino acid sequence of from position about 1 to position about 633 of FIG. 2; (e) the α'-chain of cobra C3, which corresponds to the amino acid sequence of from position about 717 to position about 1629 in FIG. 2; or (f) cobra C3a, which corresponds to the amino acid sequence of from position about 638 to position about 716 in FIG. 2. More preferably, the DNA sequence of the present invention for cobra C3 comprises: (a') the DNA sequence of from position about 1 to position about 5211 shown in FIG. 2; (b') the DNA sequence of from position about 9 to position about 4961 in FIG. 2; (c') the DNA sequence of from position about 75 to position about 4961 in FIG. 2; (d') the DNA sequence of from position about 1986 to position about 4961 in FIG. 2; (e') the DNA sequence of from about 75 to position about 1973 in FIG. 2; (f') the DNA sequence of from position about 2223 to position about 4961 in FIG. 2, or (g') the DNA sequence of from position about 1986 to position about 2222 in FIG. 2. Thus, the DNA of the present invention for cobra C3 comprises a sequence which may encode pre-pro-cobra C3, pro-cobra C3, cobra C3, the α-chain of cobra C3, the β-chain of cobra C3, the α'-chain of cobra C3, or cobra C3a.

Of course, it is to be understood that the present DNA sequences for cobra C3 encompass those which are derived from the DNA sequence shown in FIG. 2 by making any number of additions, deletions, and/or substitutions, so long as the polypeptide encoded possesses substantially the same properties as cobra C3.

In another embodiment, the present invention provides the DNA encoding CVF1. The cDNA sequence for CVF1 is 5924 nucleotides long, containing a single open reading frame of 4926 nucleotides, coding for a single pre-pro protein of 1642 amino acid residues. The reported sequence has a 5' untranslated region of 3 nucleotides and a 3' untranslated sequence of 994 nucleotides.

There are several lines of evidence that support the conclusion that the cDNA is indeed the cDNA for CVF1. First of all, the derived protein sequences at the N-termini of α-, β-, and γ-chains match those of the N-termini of the protein, with a single mismatch in each sequence (data not shown). Secondly, the location of glycosylation sites is similar to that found in the protein, with 2 or 3 sites found in the α-chain, a single site in the β-chain, and no sites found in the γ-chain. Finally, the similarity to the sequence of cobra C3 implies that we have sequenced a C3 related protein. Since the mRNA used for this sequence was isolated from the venom gland of cobras, and the sequence is different from that of cobra C3, it is likely that the sequence is that of CVF1.

From the cDNA sequence, it is clear that CVF1, like cobra and other C3 proteins, is transcribed and translated as a single pre-pro-protein, which is then processed to form the mature protein. In the case of CVF1, this processing includes the removal of the signal sequence from the N-terminus of the α-chain, the removal of the 4 arginines and the "C3a" region that lie between the α- and γ-chains, the removal of the "C3d.g" region that lies between the C-terminus of the γ-chain and the N-terminus of the β-chain, and the glycosylation that occurs on the 2 (or 3) sites in the α-chain and the single site that occurs in the β-chain. While it is not known if all 3 sites in the α-chain are glycosylated, it seems likely that the close proximity of the two sites at positions 131 and 136 would not allow the glycosylation of one if the other is already glycosylated.

As stated above, CVF1 shows a great deal of homology to cobra C3, both at the protein and at the nucleic acid level. One of the goals in sequencing both cobra C3 and CVF1 was to determine if the two proteins are derived from the same gene (through differential processing at either the RNA or protein level) or from different genes. Comparing the CVF cDNA sequence to that of cobra C3 shows that the two proteins are derived from different, though closely related genes. The main reason for this conclusion is that the comparison of the two nucleic acid sequences shows that the similarity is spread throughout the molecule, with differences not localized to discreet regions. If CVF1 were a product of differential processing at the protein level, it would be expected that the cDNA sequences would be identical throughout. If the differential processing takes place at the RNA level, then one would expect to see portions of the sequence that are identical, interspersed with regions that have little or no similarity to one another. Since the two cDNAs are highly similar throughout their lengths, it is most likely that they are derived from two different genes that are closely related to one another.

The Thioester site and Factor H binding site of CVF1 and cobra C3 are remarkably similar, even though neither is present in the mature CVF1 protein. The degree of similarity found in this region, where there is no selective pressure to maintain the homology, is further proof that the CVF1 gene arose quite recently. The similarity between the two genes is also evident in the "C3a" region, that also is not present in the mature protein, and in the first 200 nucleotides of the 3' untranslated region, again implying that CVF1 and C3 only recently diverged from one another.

Recently, protease activities have been characterized in cobra venom that are able to cleave human C3 into a form that resembles C3b functionally, but has a similar subunit structure to CVF1 (O'Keefe, M. C., L. H. Caporale, and C. W. Vogel. 1988. A novel cleavage product of human complement component C3 with structural and functional properties of cobra venom factor. *J. Biol. Chem.* 263:12690). Since this activity appears to be specific, and not just a random protease, it is possible that this protease serves in the maturation pathway of CVF1. Comparing the venom protease cleavage sites in human C3 to the processing sites in CVF1 shows that the enzyme cleaves human C3 at a position 11 amino acid residues downstream from the actual CVF1 processing site at the N-terminus of the γ-chain, though the venom protease site appears to be in the middle of one of the proposed Factor B binding sites. The second venom protease cleavage site is in a position similar to the C-terminus of the γ-chain, though this position has not been mapped in CVF1. The third venom protease cleavage site is in position 71 amino acids downstream from the N-terminus of the β-chain.

Given the complete structure of CVF1, and knowing the binding sites for certain regulatory proteins on C3, it should be possible to account for some of the unique properties of CVF1 in activating complement. For example, it is known that, while Factors H and I are able to regulate the activation of complement by dissociating C3b,Bb (the C3 convertase), and by cleaving C3b, CVF1 is resistant to this regulation. Mapping the Factor H binding site on CVF1 shows that the binding site is in the "C3d.g" domain that is removed during the maturation of the protein. Therefore, Factor H is unable to bind to the CVF1 containing C3/C5 convertase, preventing Factor I from cleaving the CVF moiety of the convertase. It is also interesting to speculate on the intrinsic stability of the CVF1 containing C3/C5 convertase compared to the enzyme that contains C3. Comparing the Factor B binding sites to the two proteins should provide some insight into the increased stability of the CVF1,Bb complex. One difference between the factor B binding site is the replacement of the serine at position 721 of CVF1 with an acidic amino acid in C3s.

The DNA sequence of the present invention for CVF1 comprises any DNA sequence encoding a polypeptide having the amino acid sequence of: (g) pre-pro-CVF1, which corresponds to the amino acid sequence of from position about −22 to position about 1620 in FIG. 14; (h) pro-CVF1, which corresponds to the amino acid sequence of from position about 1 to position about 1620 in FIG. 14; (i) the amino acid sequence of from position about 1 to position about 1010 in FIG. 14; (j) the amino acid sequence of from position about 711 to position about 1620 in FIG. 14; (k) the α-chain of CVF1, which corresponds to the amino acid sequence of from position about 1 to position about 627 in FIG. 14; (l) the γ-chain of CVF1, which corresponds to the amino acid sequence of from position about 711 to position about 1010 in FIG. 14; or (m) the β-chain of CVF1, which corresponds to the amino acid sequence of from position about 1242 to position about 1620 in FIG. 2. More preferably, the DNA sequence of the present invention for CVF1 comprises: (h') the DNA sequence of from position about 1 to position about 5929 in FIG. 14; (i') the DNA sequence of from position about 4 to position about 4929 in FIG. 14; (j') the DNA sequence of from position about 70 to position about 4929 in FIG. 14; (k') the DNA sequence of from position about 70 to position about 3299 in FIG. 14; (l') the DNA sequence of from position about 2200 to position about 4929 in FIG. 14; (m') the DNA sequence from position about 70 to position about 951 in FIG. 14; (n') the DNA sequence of from position about 2200 to position about 3299 in FIG. 14; or (o') the DNA sequence of from position about 3793 to position about 4929 in FIG. 14.

Thus, the DNA of the present invention for CVF1 may comprise a DNA sequence which encodes pre-pro-CVF1, pro-CVF1, the α-chain of CVF1, the β-chain of CVF1, the portion of pro-CVF1 which contains from the amino-terminus of the α-chain to the carboxy-terminus of the γ-chain; or the portion of pro-CVF1 which contains from the amino-terminus of the γ-chain to the carboxy-terminus of the β-chain.

Figure 14C:
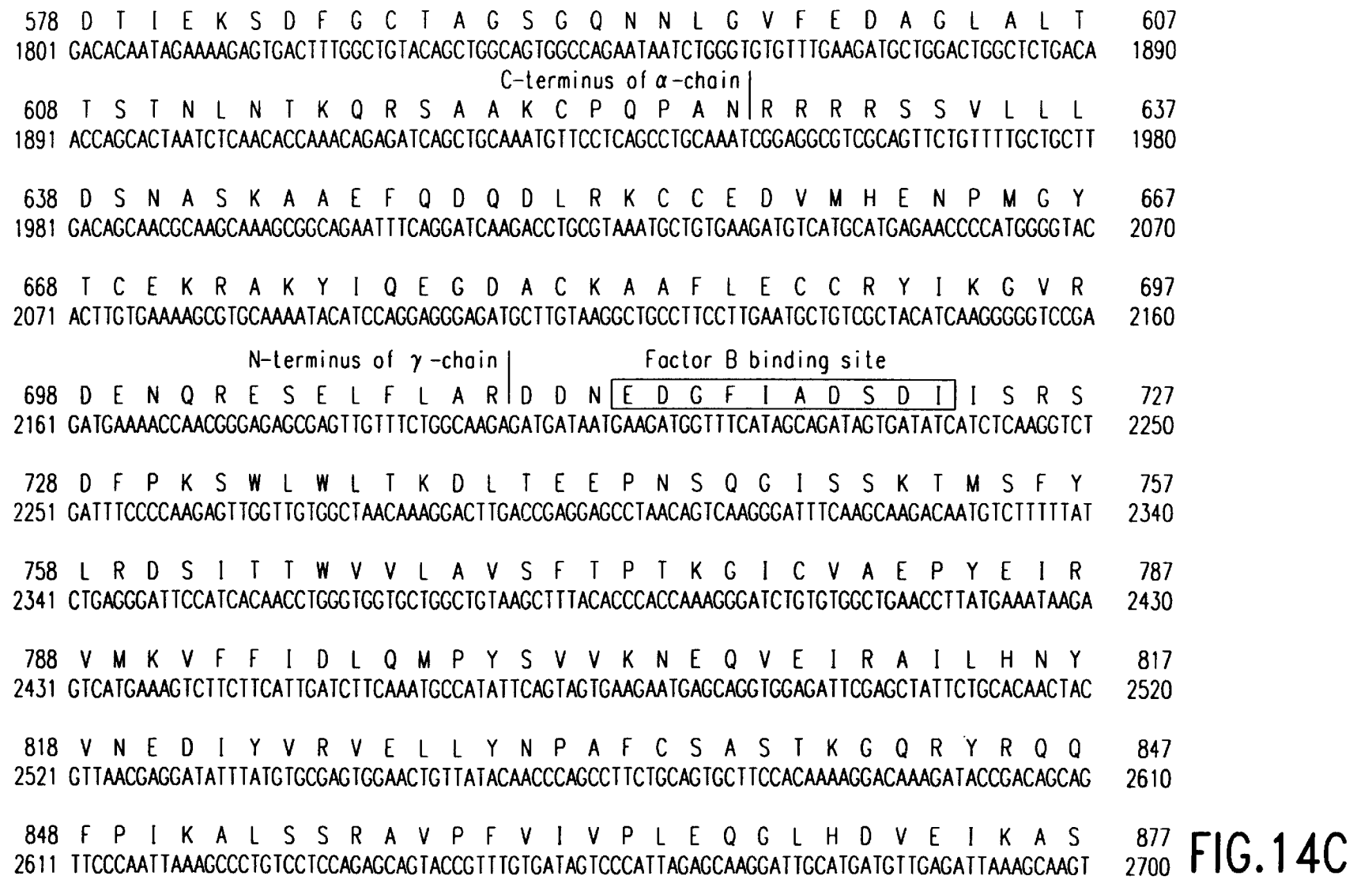

Of course, it should be understood that the present DNA sequence encoding CVF1 encompasses those derived from the sequence shown in FIG. 14 by any number of additions, deletions and/or substitutions, so long as the encoded polypeptide possesses substantially the same properties as CVF1, such as resistance to Factor H and/or I control and the ability to form a convertase with b, which is stable and does not decay rapidly.

Figure 22C:
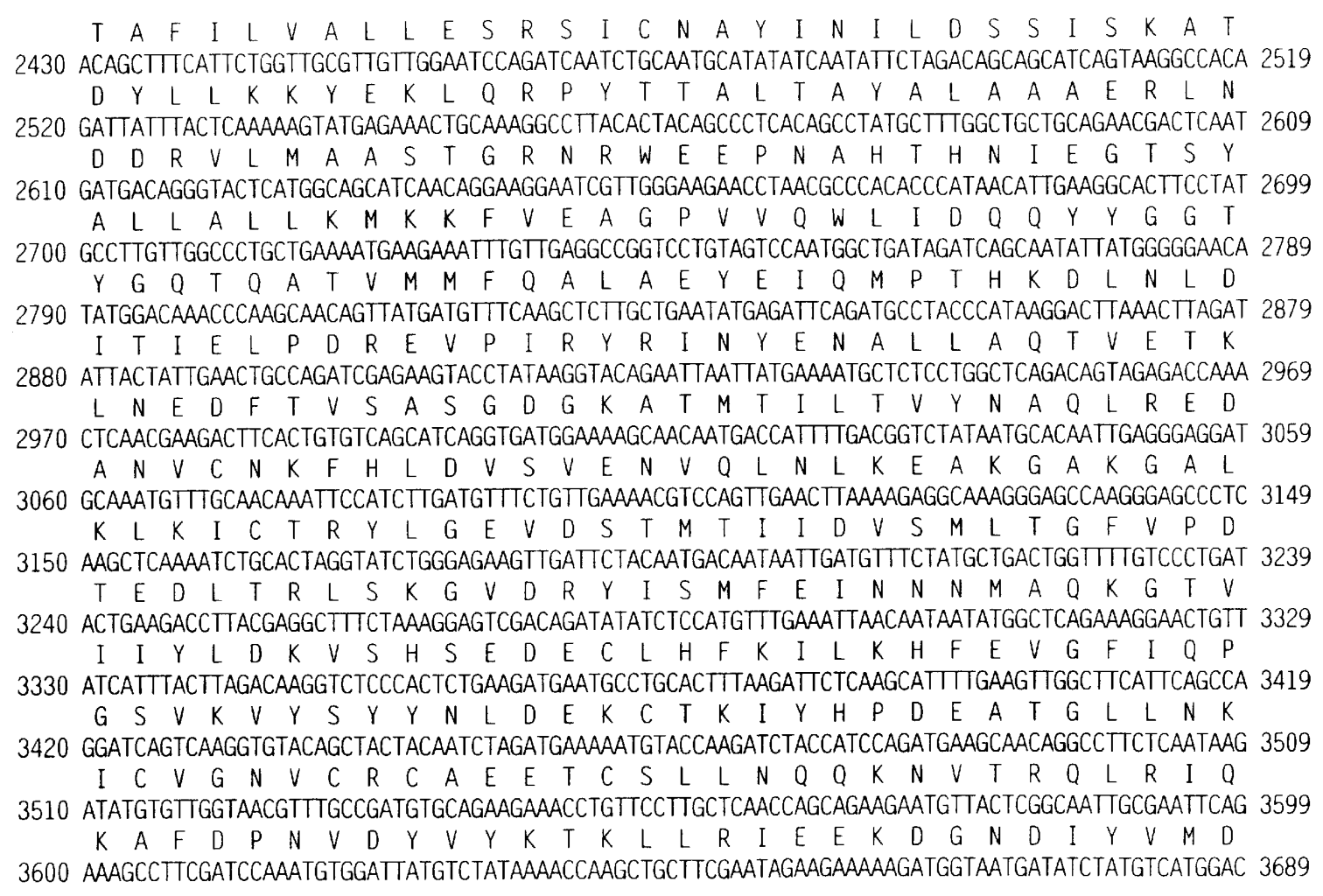

In another embodiment, the present invention provides DNA sequences for CVF2 and derivatives thereof. A partial sequence encoding of CVF2 is shown in FIG. 22. A full length sequence encoding pre-pro-CVF2 may be constructed by ligating the 3' end of any DNA sequence which encodes for a polypeptide having the amino acid sequence of from position about −22 to position about 299, as shown in FIG. 14 to the 5' end of any DNA sequence encoding a polypeptide having the amino acid sequence as shown in FIG. 22.

As in the case of CVF1, the DNA of the present invention for CVF2 may comprise any DNA sequence that encodes: (n) pre-pro-CVF2, corresponding to the amino acid sequence in which the carboxy-terminus of the amino acid sequence of from position about −22 to position about 299 in FIG. 14 is bonded to the amino-terminus of the amino acid sequence of from position about 1 to position about 1333 in FIG. 22; (o) pro-CVF2, corresponding to the amino acid sequence in which the carboxy-terminus of the amino acid sequence of from position about 1 to position about 299 in FIG. 14 is bonded to the amino-terminus of the amino acid sequence of from position about 1 to position about 1333 in FIG. 22; (p) the amino acid sequence in which the carboxy-terminus of the amino acid sequence of from position about 1 to position about 299 in FIG. 14 is bonded to the amino-terminus of the amino acid sequence of from position about 1 to position about 2147 in FIG. 22; (q) from position about 1248 to position about 4001 in FIG. 22; (r) the α-chain of CVF2, which corresponds to the amino acid sequence in which the carboxy terminus of the amino acid sequence from position about 1 to position about 299 in FIG. 14 is bonded to the amino acid sequence from position about 1 to position about 332 in FIG. 22; (s) the γ-chain of CVF2, which corresponds to the amino acid sequence from position about 416 to position about 715 in FIG. 22; or (t) the β-chain of CVF2, which corresponds to the amino acid sequence of from position about 947 to position about 1333 in FIG. 22.

More preferably, the DNA sequence for CVF2 comprises a DNA sequence corresponding to the sequence derived by ligating the 3' end of DNA sequence, X, from FIG. 14 to the 5' end of DNA sequence, Y, from FIG. 22, where X and Y are shown in the Table below:

|      | X          | Y         |
| ---- | ---------- | --------- |
| (p') | 1 to 964   | 1 to 4138 |
| (q') | 4 to 964   | 1 to 4001 |
| (r') | 70 to 964  | 1 to 4001 |
| (s') | 70 to 964  | 1 to 2147 |
| (t') | 70 to 964  | 1 to 998  |

(u') the DNA sequence from position about 1248 to position about 2147 in FIG. 22; (v') the DNA sequence from position about 2841 to position about 4001 in FIG. 22; or (w') the DNA sequence from position about 1248 to position about 4001 in FIG. 22.

Again, it is to be understood that the present sequence encoding CVF2 includes those derived from the sequences shown in Figure(s) 14 and/or 22 by any number of additions, deletions, and/or substitutions, so long as the encoded polypeptide possesses substantially the same properties as CVF1.

In another embodiment, the present invention provides plasmids which comprise a DNA sequence encoding pre-pro-cobra C3, pro-cobra C3, the α-chain of cobra C3, the β-chain of cobra C3, the α'-chain of cobra C3, Cobra C3a, pre-pro CVF1, pro-CVF1, the amino acid sequence of from position about 1 to position about 1010 in FIG. 14, the amino acid sequence of from position about 711 to position about 1620 in FIG. 14, the α-chain of CVF1, the γ-chain of CVF1, the β-chain of CVF1, pre-pro CVF2, pro-CVF2, the amino acid sequence in which the carboxy-terminus of the amino acid sequence of from position about 1 to position about 299 in FIG. 14 is bonded to the amino-terminus of the amino acid sequence of from position about 1 to position about 715 in FIG. 22, the amino acid sequence from position about 416 to position about 1333 in FIG. 22, the α-chain of CVF2, the γ-chain of CVF2, or the β-chain of CVF2. Any plasmid suitable for cloning or expression may be used and the DNA may be inserted in the plasmid by conventional techniques. Suitable plasmids and the techniques used to insert the DNA of the present invention into such plasmids are well known to those skilled in the art. For expression purposes, the DNA should be inserted downstream from a promoter and in the proper reading frame.

In another embodiment, the present invention provides transformed hosts which contain a DNA sequence encoding pre-pro-cobra C3, pro-cobra C3, the α-chain of cobra C3, the β-chain of cobra C3, the α'-chain of cobra C3, cobra C3a, pre-pro CVF1, pro-CVF1, the amino acid sequence of from position about 1 to position about 1010 in FIG. 14, the amino acid sequence of from position about 711 to position about 1620 in FIG. 14, the α-chain of CVF1, the γ-chain of CVF1, the β-chain of CVF1, pre-pro CVF2, pro-CVF2, the amino acid sequence in which the carboxy-terminus of the amino acid sequence of from position about 1 to position about 299 in FIG. 14 is bonded to the amino-terminus of the amino acid sequence of from position about 1 to position about 715 in FIG. 22, the amino acid sequence from position about 416 to position about 1333 in FIG. 22, the α-chain of CVF2, the γ-chain of CVF2, or the β-chain of CVF2. Again, suitable hosts and the means for transforming them are well know to those skilled in the art. Examples of suitable prokaryotic hosts include: *E coli, B. subtilis*, etc. In the present case, it may be desirable to express the present genes in eukaryotic hosts such as CHO or NIH 3T3 cells.

In yet another embodiment, the present invention provides a method for preparing a polypeptide by culturing a transformed host comprising a DNA sequence encoding pre-pro-cobra C3, pro-cobra C3, the α-chain of cobra C3, the β-chain of cobra C3, the α'-chain of cobra 3, cobra C3a, pre-pro CVF1, pro-CVF1, the amino acid sequence of from position about 1 to position about 1010 in FIG. 14, the amino acid sequence of from position about 711 to position about 1620 in FIG. 14, the α-chain of CVF1, the γ-chain of CVF1, the β-chain of CVF1, pre-pro CVF2, pro-CVF2, the amino acid sequence in which the carboxy-terminus of the amino acid sequence of from position about 1 to position about 299 in FIG. 14 is bonded to the amino-terminus of the amino acid sequence of from position about 1 to position about 715 in FIG. 22, the amino acid sequence of from position about 416 to position about 1333 in FIG. 22, the α-chain of CVF2, the γ-chain of CVF2, or the β-chain of CVF2. The exact conditions required for the culturing will depend of course on the identity of the transformed host. However, selection of culture conditions is well within the abilities of the skilled artisan.

It should be noted that although CVF1 and CVF2 are glycosylated as naturally occurring, it has been discovered that these polypeptides retain their activity even in the unglycosylated state. Thus, an active product may be obtained even if produced by a host incapable of effecting the proper glycosylation.

Further, C3, CVF1, and CVF2 may be processed from the pre-pro-form by treatment with either whole cobra venom or the purified proteases from cobra venom, as described in the Doctoral thesis of M. Clare O'Keefe, Georgetown University, 1991. Thus, active C3, CVF1, and CVF2 may be obtained even when produced by a host incapable of the proper post-translational processing.

The CVF1 and CVF2 produced by the present process may be useful for the treatment of cancer. Thus, CVF1 or CVF2 may be bound to an antibody which recognizes a tumor cell. In this way, the CVF1 or CVF2 will be directed to the target cancer cells. Since, CVF1 and CVF2 are insensitive to factor H control, this method will lead to the selective destruction of the cancer cells. Likewise, cobra C3 may not be inactivated by human factor H and, thus, may be useful in the same method. Other features of the invention will become apparent in the course of the following descriptions of exemplary embodiments which are given for illustration of the invention and are not intended to be limiting thereof.

EXAMPLES

I. Cobra C3

Materials and Methods

Materials

Solutions for RNA isolation, cDNA preparation, λgt11 cloning, and hybridization probe labeling were obtained from Amersham (Skokie, Ill.). Restriction enzymes were from either Pharmacia Fine Chemicals (Piscataway, N.J.) or from New England Biolabs (Beverley, Mass.). Plasmid pUC 18 was purchased from Boehringer Mannheim (Indianapolis, Ind.), and M13 mp 18 and mp 19 were purchased from New England Biolabs (Yanisch-Perron, C.,J. Vieira, and J. Messing. 1985. Improved M13 phage cloning vectors and host strains: nucleotide sequences of the M13 mp18 and pUC19 vectors. *Gene* 33:103). DNA modification enzymes were obtained from Pharmacia or New England Biolabs, and DNA sequencing reagents were obtained from United States Biochemicals (Cleveland, Ohio). Anti-mouse IgG+IgM (alkaline phosphatase conjugated) was purchased from Tago (Burlingame, Calif.). [$\alpha$-$^{32}$P]dATP, [$\alpha$-$^{32}$P]dCTP, and [$\alpha$-$^{35}$S]dATP were obtained from Amersham.

RNA isolation from cobra liver

Adult cobras (Naja naja kaouthia, 1.5–2 meters in length) were premedicated with ketamine (~70 mg/kg i.m.) and anesthetized with halothane/oxygen after tracheal intubation essentially as described (Vogel, C.-W.., and H. J. Muller-Eberhard, 1985. The cobra complement system: I. The alternative pathway of activation, *Dev. Comp. Immunol.* 9:311). The livers were removed and immediately frozen in liquid nitrogen. For RNA preparation, approximately one gram of tissue was suspended (while frozen) in 20 ml of a solution of 4M guanidinium thiocyanate and 1.14M β-mercaptoethanol, and the RNA extracted according to the instructions supplied with the Amersham RNA Extraction Kit. This procedure is based on a published procedure (Han, J. H., C. Stratowa, and W. J. Rutter, 1987. Isolation of full-length putative rat lysophospholipase cDNA using improved methods for mRNA isolation and cDNA cloning. *Biochemistry* 26:1617). Poly-A containing RNA was then isolated by chromatography over oligo-dT cellulose (Jacobson, A. Purification and fractionation of poly(A)$^{+RNA}$. 1987. In *Methods in Enzymology*, Vol. 152. S. L. Berger and A. R. Kimmel, eds. Academic Press, Orlando, Fla., p. 254).

cDNA synthesis and cloning

First strand (Krug, M. S., and S. L. Berger. 1987. First-strand cDNA synthesis primed with oligo(dT). In *Methods Enzymology*. Vol. 152. S. L. Berger and A. R. Kimmel, eds. Academic Press. Orlando, Fla., p. 316) and second strand (Gubler, U. 1987. Second-strand cDNA synthesis: mRNA fragments as a primer. In *Methods in Enzymology*, vol. 152. S. L. Berger and A. R. Kimmel. eds. Academic Press, Orlando. Fla. p. 330) synthesis of cobra liver cDNA was performed using the cDNA synthesis kit from Amersham. cDNA was synthesized using both oligo-dT and random hexamers as the primers. cDNA was then prepared for cloning into λgt11 (Wu. R., T. Wu. and A. Ray. 1987. Adaptors, linkers, and methylation. In *Methods in Enzymology*. vol. 152. S. L. Berger and A. R. Kimmel, eds. Academic Press, Orlando, Fla. p. 343), ligated with λgt11 arms, and the recombinant λ clones were packaged (Hohn, B., and K. Murray. 1977. Packaging recombinant DNA molecules into bacteriophage particles in vitro. *Proc. Natl. Acad. Sci. USA* 74:3259). *Escherichia coli* Y1090(r$^-$, m$^+$) was used as the host for recombinant λgt11.

Purification of cobra C3 and raising of mouse antisera to cobra C3

Cobra C3 was purified (Petrella, E. C., R. Bredehorst, and C.-W.. Vogel. 1989. Purification of cobra C3: initial characterization and comparison to cobra venom factor. *Complement Inflamm.* 6:386) and polyclonal antisera were raised in mice as described (Grier, A. H., M. Schultz, and C.-W.. Vogel. 1987. Cobra venom factor and human C3 share carbohydrate antigenic determinants. *J. Immunol.* 139:1245).

Screening of λgt 11 libraries

Libraries were screened with antibody probes after transferring recombinant proteins to nitrocellulose filters (Young, R. A., and R. W. Davis. 1983. Yeast RNA polymerase II genes: isolation with antibody probes. *Science* 222:778; Huynh, T. V., R. A. Young, and R. W. Davis. 1985, Construction and screening cDNA libraries in λgt10 and λgt11. In *DNA Cloning* vol. 1. A Practical Approach. D. M. Glover. ed. IRL Press, Oxford, p 49). Mouse anti-cobra C3 was used as the primary antibody for screening the liver library. Further plaque purification was done with successively lower plaque densities. Later screening, using cDNA clones derived by the antibody screening procedure as probes, was done by hybridization (Wahl, G. M., and S. L. Berger. 1987. Screening colonies of plaques with radioactive nucleic acid probes. In *Methods in Enzymology*, vol. 152. S. L. Berger and A. R. Kimmel, eds. Academic Press, Orlando, Fla., p. 415). These probes were labeled with [$\alpha$-$^{32}$P]dATP or [$\alpha$-$^{32}$P]dCTP (Feinberg, A. P., and B. Vogelstein. 1983. A technique for radio-labeling DNA restriction endonuclease fragments to high specific activity. *Anal. Biochem.* 132:6).

Subcloning and DNA sequence analysis

Clones containing C3 inserts were grown up on agarose plates and their DNA prepared as described (Maniatis, T., E. F. Fritsch, and J. Sambrook. 1982. *Molecular Cloning—A Laboratory Manual*. Cold Spring Harbor Laboratory, Cold Spring Harbor, N.Y.). Inserts were isolated by EcoR1 digestion, followed by agarose gel electrophoresis. Fragments were eluted from the gel using an electroelution device (IBI, New Haven. Conn.). The DNA inserts were then ligated into pUC 18 so that large quantities of the insert could be prepared for restriction analysis and DNA sequencing. Subfragments of the C3 inserts for sequencing were generated by digestion with restriction enzymes that cut at a 4 bp recognition sequence (HaeIII, HinfI, and RsaI). These subfragments were then cloned into SmaI cut M 13 mp18 or mp19 to generate sequencing templates. Sequencing was performed using the dideoxy-chain termination technique (Sanger, F. S. Nicklen, and A. R. Coulson. 1977. DNA sequencing with chain terminating inhibitors, *Proc. Natl. Acad. Sci. USA* 74:5463). The Sequenase Version 2.0 sequencing kit from U.S. Biochemicals was used as the source of enzymes, chemicals, and primers for sequencing (Tabor, S., and C. C. Richardson. 1989. Effect of manganese ions on the incorporation of dideoxynucleotides by bacteriophage T7 DNA polymerase and *Escherichia coli* DNA Polymerase I. *Proc. Natl. Acad. Sci. USA* 86:4076). Sequences were analyzed using the Genetics Computer Group of the Wisconsin Biotechnology Center package of sequence analysis programs (Devereux, J. R., P. Haeberli, and O. A. Smithies. 1984. Comprehensive set of sequence analysis programs for the VAX. *Nucleic Acids Res.* 12:387). Both strands were sequenced for approximately 85% of the reported sequence. For those regions where only one strand was sequenced, several nonambiguous gels were used to generate the consensus sequence. Sequence alignments were done with the gap program (Needleman, S. B., and C. D. Wunsch. 1970. A general method applicable to the search for similarities in the amino acid sequences of two proteins. *J. Mol. Biol.* 48:443). Dot plot comparisons (Maizel, Jr., J. V., and R. P. Lenk. 1981. Enhanced graphic matrix analysis of nucleic acid and protein sequences. *Proc. Natl. Acad. Sci. USA* 78:7665) and the determination of conservative replacements of amino acids (Dayhoff, M. O., ed. 1978, *Atlas of Protein Sequence and Structure*, vol. 5, National Biomedical Research Foundation, Washington, D.C.) were performed as described. Hydrophilicity/hydrophobicity plots were generated as described (Hop, T. P., and K. R. Woods. 1981. Prediction of protein antigenic determinants from amino acid sequences. *Proc. Natl. Acad. Sci., USA* 78:3824). Sequence analyses were performed with the reported sequences for C3 from human (DeBruijn, M. H. L., and G. H. Fey. 1985. Human complement component C3: cDNA coding sequence and derived primary structure. *Proc. Natl. Acad. Sci. USA* 82:708), mouse (Lundwall, A., R. A. Wetsel, H. Domdey, B. F. Tack, and G. H. Fey. 1984. Structure of murine complement component C3: I. Nucleotide sequence of cloned complementary and genomic DNA coding for the β-chain *J. Biol. Chem.* 259:13851; Wetsel, R. A., A. Lundwall, F. Davidson, T. Gibson, B. F. Tack, and G. H. Fey. 1984. Structure of murine complement component C3: II. Nucleotide sequence of cloned complementary DNA coding for the α-chain. *J. Biol. Chem.* 259:13857), rat (Misumi, Y., M. Sohda, and Y. Ikehara. 1990. Nucleotide and deduced amino acid sequence of rat complement C3. *Nucleic Acids Res.* 18:2178), rabbit (Kusano, M., N. H. Choi, M. Tomita, K. I. Mamamoto, S. Migita, T. Sekiya, and S. Nishimura. 1986. Nucleotide sequence of cDNA and derived amino acid sequence of rabbit complement component C3 α-chain. *Immunol. Inv.* 15:365), and Xenopus (Grossberger, D., A. Marcuz, L. Du Pasquier, and J. D. Lambris. 1989. Conservation of structural and functional domains in complement component C3 of Xenopus and mammals. *Proc. Natl. Acad. Sci. USA* 86:1323). The numbering of amino acid positions throughout the paper is based on the cobra pro-C3 molecule, starting with number one at the NH$_2$-terminus of the β-chain (comp. FIG. 2).

RESULTS

Screening of the cobra liver library

Poly-A$^+$ RNA from cobra liver was used for the preparation of cDNA, which was cloned into the EcoR1 site of λgt11. Two libraries were prepared, one from cDNA that was primed by oligo-dT, and one that was primed from a random mixture of oligonucleotides. Each library contained more than 5×10$^6$ clones. Initially, 5×10$^5$ plaques from the random primed library were screened for clones expressing cobra C3 by detection with the mouse anti-cobra C3 antisera. In our original screening, three cobra C3 clones (called C3-5, C3-6, and C3-7; 2.5, 2.4, and 1.6 kb, respectively; FIG. 1) were isolated. Sequence analysis of the three C3 clones revealed that they all overlapped one another, containing a single open reading frame of 3709 bp. When the derived amino acid sequence of this protein was compared to that of human C3, it was found that the portion of cobra C3 that had been sequenced contained almost the entire β-chain and the NH$_2$-terminal two-thirds of the α-chain, representing approximately 75% of the mature protein.

To isolate clones representing the rest of the C3 mRNA, the liver library was rescreened by hybridization, using fragments of the original three clones as hybridization probes. Ten clones representing the 3' end of the mRNA were isolated from the oligo-dT primed λgt11 library, varying in size from 2.1 kb to almost 4 kb in length. The smallest of these, C3-37, was chosen for sequence analysis. Clones presumably representing the 5' end of the C3 message were isolated from the random oligo primed library. Of these, one clone (C3-72: 0.9 kb) was sequenced. FIG. 1 shows the placement of the five clones used for sequencing the cobra C3 message.

Structure of cobra C3 mRNA

The cobra C3 mRNA is 5211 bp in length. It contains a single open reading frame of 4953 bp (FIG. 2). The cDNA has a 3' untranslated region of 250 bp, including a poly-A tail of seven residues. The translated message codes for a single pre-pro-C3 molecule of 1651 amino acids starting at position 9 of the mRNA. The pre-pro-protein has a 22 amino acid residue signal sequence with a core rich in hydrophobic amino acids. The signal sequence is followed by the β-chain of 633 amino acid residues. The C-terminus of the β-chain is separated from the NH$_2$-terminus of the α-chain by four arginine residues. The α-chain is 992 amino acids in length. There are no N-glycosylation sites in either the α-chain or the β-chain of cobra C3. Cobra C3 contains one N-glycosylation recognition sequence Asn-X-Ser at position 157–159. However, the residue at position 158 is proline, which has been shown to prevent glycosylation (Bause, E. 1983. Structural requirements of N-glycosylation of proteins: studies with proline peptides as conformational probes. *Biochem. J.* 209:331).

The G+C percentage of the cobra C3 mRNA i-S 43%, compared to a G+C percentage of greater than 53% for mammalian C3 mRNA (DeBruijn, M. H. L., and G. H. Fey. 1985. Human complement component C3: cDNA coding sequence and derived primary structure. *Proc. Natl. Acad. Sci. USA* 82:708; Lundwall, A., R. A. Wetsel, H. Domdey, B. F. Tack, and G. H. Fey. 1984. Structure of murine complement component C3: I. Nucleotide sequence of cloned complementary and genomic DNA coding for the β-chain *J. Biol. Chem.* 259:13851; Wetsel, R. A., A. Lundwall, F. Davidson, T. Gibson, B. F. Tack, and G. H. Fey. 1984. Structure of murine complement component C3: II. Nucleotide sequence of cloned complementary DNA coding for the α-chain. *J. Biol. Chem.* 259:13857). The lower G+C content of cobra C3 is reflected in the codon usage, shown in Table I, where G+C-rich codons are underrepresented as compared to mammalian C3 genes. Table II gives the amino acid composition of the α-chain, the β-chain, and the mature protein. The mature protein is made up of 1625 amino acid residues and has a molecular mass of 182 kDa consisting of an α-chain of 112 kDa and a β-chain of 70 kDa.

Homology of cobra C3 with C3 from other species

Figure 3A:
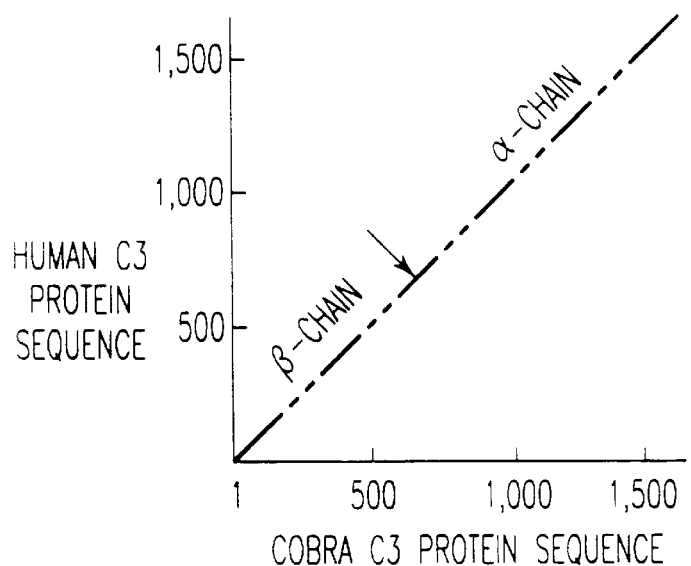
FIG. 3 illustrates dot plot comparisons of the cobra C3 protein sequence to those of human C3 (A), rat C3 (B), and murine C3 (C). The dot plots were generated using a sequence analysis program (Devereux, J. R., P. Haeberli, and O. A. Smithies. 1984. Comprehensive set of sequence analysis programs for the VAX. Nucleic Acids Res. 12:387). In that program, a moving window of 30 amino acid residues is compared, and where 21 or more residues are similar a dot is drawn on the graph. The arrow indicates the position of the α-chain/β-chain junction.
Figure 3C:
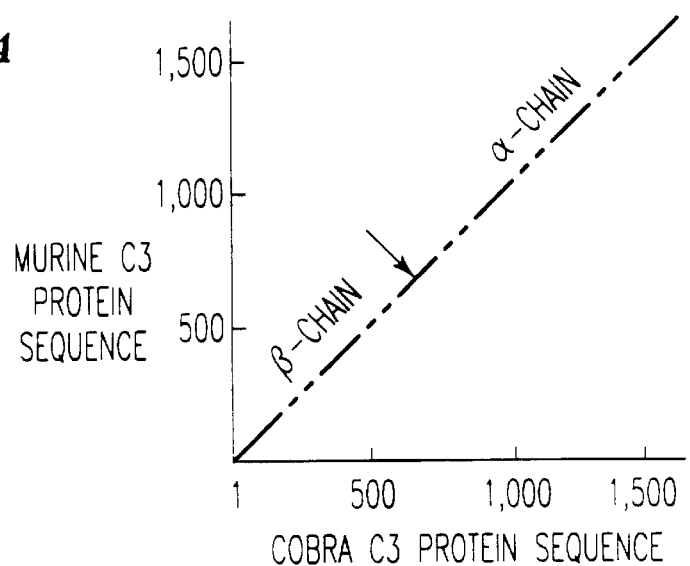
Figure 3B:
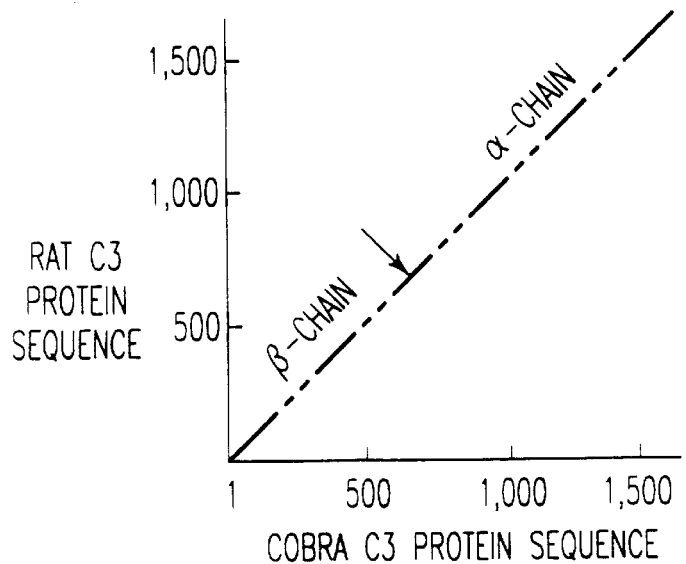
Figure 4:
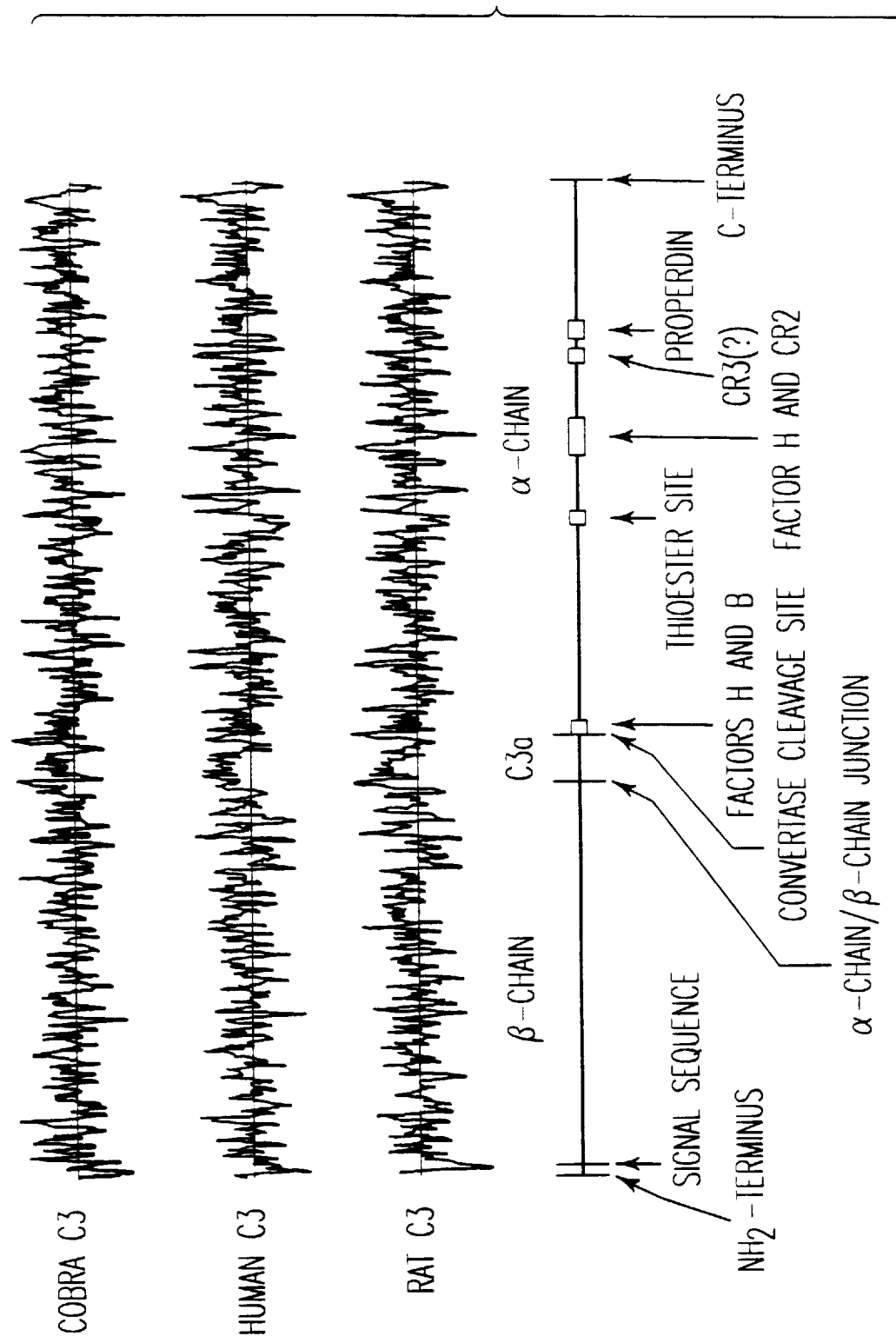
FIG. 4 shows hydophilicity/hydrophobicity plots of cobra, human, and rat C3 proteins. The plots were generated using a sequence analysis program (Devereux, J. R., P. Haeberli, and O. A. Smithies. 1984. Comprehensive set of sequence analysis programs for the VAX. Nucleic Acids Res. 12:387). Hydrophilic regions are shown above, hydrophobic regions below the line. The locations of functionally important sites are indicated.

The cDNA sequence and the derived protein sequence of cobra C3 were compared with the corresponding sequences of C3 from other species for which the full (human, mouse, rat) or partial (rabbit, *Xenopus laevis*) sequences have been reported. As is evident from Table III, the cDNA sequence of cobra C3 shows approximately 58% identity to the cDNA sequences of all five species. At the protein level, cobra C3 and the three fully sequenced mammalian C3s exhibit a sequence identity of approximately 52% and a sequence similarity of approximately 71% if one allows for conservative substitutions. Protein sequence identity and similarity are 2 to 3% lower for the partially sequenced portions of C3 from rabbit and Xenopus. Dot plot comparisons of the protein sequence of cobra C3 with those of three mammalian C3s indicate that there are large stretches of homology between the C3 proteins, with the homology extending throughout the molecule (FIG. 3). Similar results were obtained with dot plot comparisons of the nucleotide sequences (not shown). The homology of cobra C3 with mammalian C3s is further evident by comparing the hydrophilicity/hydrophobicity plots as calculated from the amino acid sequences (FIG. 4). A careful analysis of the plots indicates that the pattern of hydrophobic and hydrophilic regions is very similar throughout all three C3 proteins. In particular, all three plots show the hydrophobic signal sequence, the predominantly hydrophilic C3a region, a short hydrophilic peak at the $NH_2$-terminus of the α'-chain containing the factor H and B binding sites, a hydrophobic twin peak containing the thioester site, a relatively wide hydrophilic peak leading into a shorter hydrophobic peak at the factor H and CR2 binding site, and a wide hydrophilic peak followed by a small hydrophobic peak at the C-terminus. Proper assignment of the properdin binding site and the disputed CR3 binding site is difficult although the general pattern of the plots in that region is also similar.

Cobra C3 contains 27 cysteine residues, of which 24 are in the α-chain and only three in the β-chain. The total number and the distribution of the cysteines are identical to those in other C3 species, indicating that they are highly conserved. Other highly conserved sites include the polypeptide stretch in the pre-pro-C3 molecule linking the C-terminus of the β-chain with the $NH_2$-terminus of the α-chain including the four arginine residues that are being removed in the maturation process (FIG. 5), the C3 convertase cleavage site (FIG. 6), the thioester site (FIG. 7), and the factor B binding site (FIG. 8).

Cobra C3 also seems to have homologous binding sites for factor H (FIG. 9) and properdin (FIG. 10) as well as a conserved sequence in the functionally important region of the C3a anaphylatoxin (FIG. 11). For human C3, the binding of factor H has been proposed to occur at an "orientation site" between residues 727 and 767 and a "discontinuous binding site" between residues 1187 and 1249 (human C3 numbering), both in the α-chain (Ganu, V. S., and H. J. M üller-Eberhard. 1985. Inhibition of factor B and Factor H binding to C3b by synthetic peptide corresponding to residues 749–789 of human C3. *Complement* 2:27). At the orientation site the homology certainly exceeds the overall homology between cobra C3 and mammalian C3. At the discontinuous binding site, however, the homology does not exceed that of the overall homology of the two proteins. However, there are at least four highly conserved stretches within the factor H binding site. Collectively, these data strongly suggest that homologous binding sites exist for factor H in cobra C3.

The homology at the properdin binding site in the C-terminal portion of the α-chain is also significantly above the overall homology, similarly suggesting a conserved binding site for properdin.

The 21 C-terminal amino acid residues of C3a, known to be able to elicit nearly 100% of C3a activity, show a degree of homology that does not exceed the overall homology between cobra and mammalian C3s. However, four of the last five amino acid residues including the C-terminal arginine, are identical and similarly suggest conservation of this region of the C3 molecule.

Figure 9A:
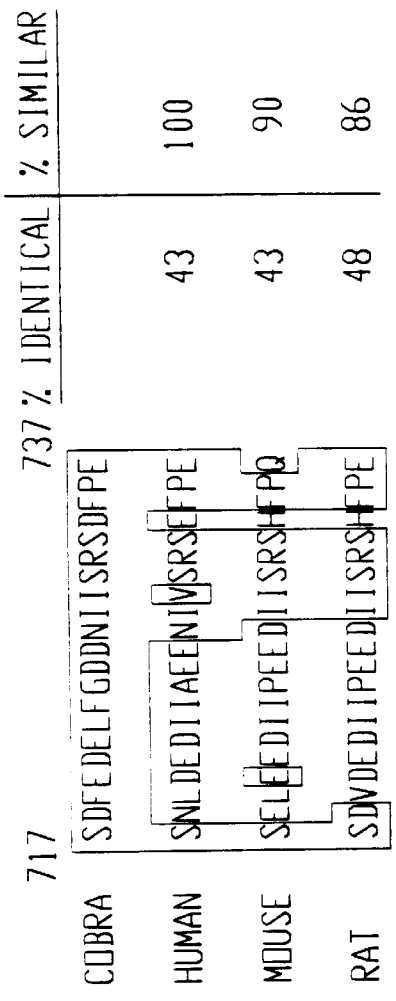
FIG. 9 provides a comparison of C3 sequences at the factor H and CR2 binding sites. The upper panel shows the factor H orientation site (SEQ ID NOS:19–22). The lower panel shows the discontinuous factor H binding site that includes the CR2 binding site (residues 1186–1197(SEQ ID NOS:23–27)) with the highly conserved LYNVEA sequence (SEQ ID NO:81) in all mammalian C3 proteins. Comparisons were made with a sequence analysis program (Devereux, J. R., P. Haeberli, and O. A. Smithies. 1984. Comprehensive set of sequence analysis programs for the VAX. Nucleic Acids Res. 12:387). Identical amino acid residues are boxed and shaded whereas conservative replacements are shaded only. Amino acid residue numbering is based on the cobra C3 sequence as shown in FIG. 2. The percent sequence identity and similarity with the cobra sequence is shown on the right.
Figure 9B:
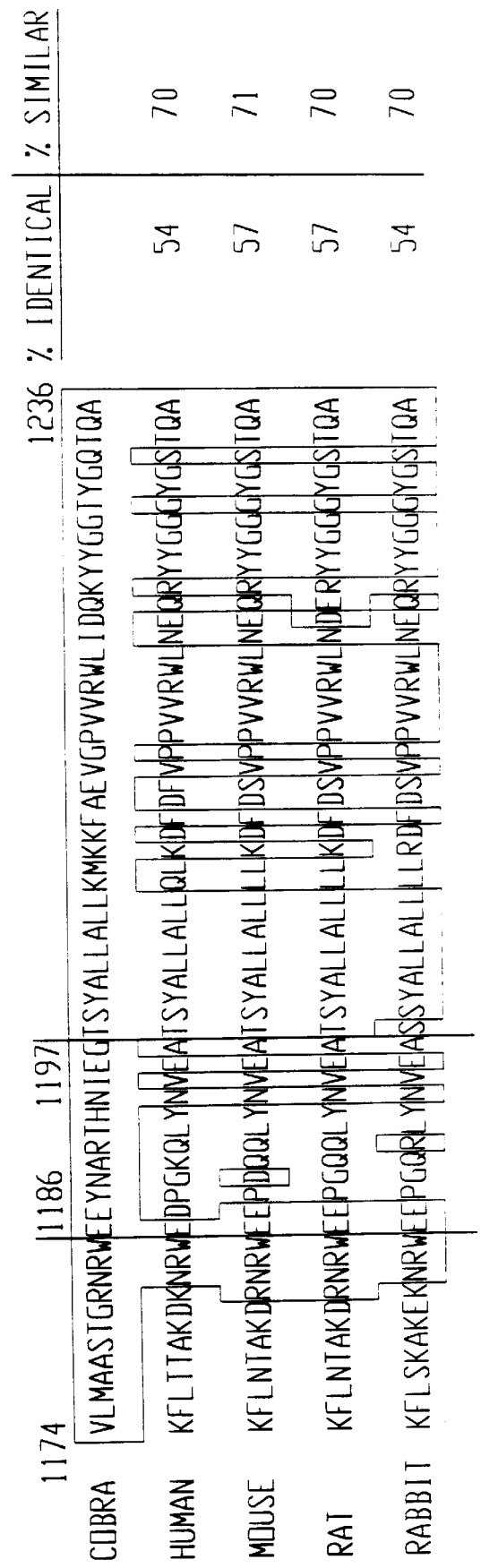

More ambiguous is the homology of the CR2 binding site (FIG. 9). Whereas all mammalian C3s show the highly conserved LYNVEA sequence within the CR2 binding site, cobra C3 only shares three of these six residues and shows an overall homology to mammalian C3s at the CR2 binding site that does not exceed the overall homology of the molecules. Accordingly, although cobra C3 may have a binding site for CR2, its existence cannot be deduced from sequence conservation by comparison with C3 from other species.

FIG. 12 shows the sequence comparison at the disputed CR3 binding site. Cobra C3 does not contain the RGD or LGD triplet but a still similar LGE triplet. However, the neighboring DATMSI sequence, which is highly conserved in other C3s, shows two substitutions in cobra C3. In addition, the overall homology in this region between cobra C3 and the C3s from other species does not exceed the overall homology of the molecules. The existence of a CR3 binding site in cobra C3 in this region cannot be deduced from these data; and the difference in the RGD and DATMSI sequences may actually support the hypothesis that this particular region of C3 does not represent the CR3 binding site in any species (Taniguchi-Sidle, A., and D. E. Isenman. 1992. Mutagenesis of the Arg-Gly-Asp (RGD) triplet of human complement component C3 does not abolish binding of iC3b to the leukocyte integrin complement receptor type III (CR3, CD11B/CD18). *J. Biol. Chem.* 267:635).

TABLE I

Codon frequency for cobra C3 and human C3 coding sequences[a]

| Amino Acid | Codon | Cobra C3 | Human C3 | Amino Acid | Codon | Cobra C3 | Human C3 |
|---|---|---|---|---|---|---|---|
| Gly | GGG | 0.20 | 0.27 | Trp | UGG | 1.00 | 1.00 |
| Gly | GGA | 0.37 | 0.17 | End | UGA | 0.00 | 0.00 |
| Gly | GGU | 0.21 | 0.12 | Cys | UGU | 0.56 | 0.31 |
| Gly | GGC | 0.23 | 0.44 | Cys | UGC | 0.44 | 0.69 |
| Glu | GAG | 0.33 | 0.69 | End | UAG | 0.00 | 0.00 |
| Glu | GAA | 0.67 | 0.31 | End | UAA | 0.00 | 0.00 |
| Asp | GAU | 0.69 | 0.28 | Tyr | UAU | 0.57 | 0.16 |
| Asp | GAC | 0.31 | 0.72 | Tyr | UAC | 0.43 | 0.82 |

TABLE I-continued

Codon frequency for cobra C3 and human C3 coding sequences[a]

| Amino Acid | Codon | Cobra C3 | Human C3 | Amino Acid | Codon | Cobra C3 | Human C3 |
|---|---|---|---|---|---|---|---|
| Val | GUG | 0.42 | 0.50 | Leu | UUG | 0.20 | 0.10 |
| Val | GUA | 0.14 | 0.05 | Leu | UUA | 0.11 | 0.01 |
| Val | GUU | 0.22 | 0.12 | Phe | UUU | 0.59 | 0.22 |
| Val | GUC | 0.22 | 0.33 | Phe | UUC | 0.41 | 0.78 |
| Ala | GCG | 0.03 | 0.08 | Ser | UCG | 0.03 | 0.10 |
| Ala | GCA | 0.37 | 0.14 | Ser | UCA | 0.18 | 0.08 |
| Ala | GCU | 0.38 | 0.19 | Ser | UCU | 0.25 | 0.17 |
| Ala | GCC | 0.23 | 0.59 | Ser | UCC | 0.19 | 0.29 |
| Arg | AGG | 0.28 | 0.20 | Arg | CGG | 0.12 | 0.24 |
| Arg | AGA | 0.23 | 0.10 | Arg | CGA | 0.19 | 0.15 |
| Ser | AGU | 0.18 | 0.10 | Arg | CGU | 0.12 | 0.10 |
| Ser | AGC | 0.16 | 0.27 | Arg | CGC | 0.07 | 0.22 |
| Lys | AAG | 0.40 | 0.73 | Gln | CAG | 0.55 | 0.08 |
| Lys | AAA | 0.60 | 0.27 | Gln | CAA | 0.45 | 0.20 |
| Asn | AAU | 0.65 | 0.21 | His | CAU | 0.73 | 0.22 |
| Asn | AAC | 0.35 | 0.79 | His | CAC | 0.27 | 0.78 |
| Met | AUG | 1.00 | 1.00 | Leu | CUG | 0.29 | 0.49 |
| Ile | AUA | 0.16 | 0.10 | Leu | CUA | 0.07 | 0.08 |
| Ile | AUU | 0.56 | 0.15 | Leu | CUU | 0.14 | 0.05 |
| Ile | AUC | 0.28 | 0.75 | Leu | CUC | 0.19 | 0.27 |
| Thr | ACG | 0.05 | 0.15 | Pro | CCG | 0.04 | 0.14 |
| Thr | ACA | 0.40 | 0.15 | Pro | CCA | 0.52 | 0.22 |
| Thr | ACU | 0.31 | 0.12 | Pro | CCU | 0.32 | 0.19 |
| Thr | ACC | 0.25 | 0.58 | Pro | CCC | 0.12 | 0.45 |

[a]Given as fraction of codons for a given amino acid. Data for human C3 are derived from DeBruijn, M.H.L., and G.H. Fey. 1985. Human complement component C3: cDNA coding sequence and derived primary structure. Proc. Natl. Acad. Sci. USA 82:708.

TABLE II

Amino acid composition of cobra C3 and its α- and β-chains

| Residue | α-Chain | β-Chain | Whole Protein |
|---|---|---|---|
| Ala | 71 | 37 | 108 |
| Cys | 24 | 3 | 27 |
| Asp | 66 | 37 | 103 |
| Glu | 76 | 27 | 103 |
| Phe | 30 | 25 | 55 |
| Glu | 55 | 43 | 98 |
| His | 16 | 13 | 29 |
| Ile | 68 | 38 | 106 |
| Lys | 67 | 44 | 111 |
| Leu | 91 | 45 | 136 |
| Met | 20 | 10 | 30 |
| Asn | 49 | 31 | 80 |
| Pro | 31 | 37 | 68 |
| Gln | 46 | 28 | 74 |
| Arg | 45 | 26 | 71 |
| Ser | 58 | 44 | 102 |
| Thr | 58 | 50 | 108 |
| Val | 67 | 65 | 132 |
| Trp | 12 | 3 | 15 |
| Tyr | 42 | 27 | 69 |
| Total | 992 | 633 | 1625 |
| $M_r$ | 112,067 | 70,034 | 182,101 |

TABLE III

Sequence homology of cobra C3 with C3 from other species

| Species | % Identity (Similarity) of Protein Sequence | % Identity of DNA Sequence |
|---|---|---|
| Completely sequenced C3 mRNA | | |
| Human | 52.0 (70.7) | 56.8 |
| Mouse | 52.8 (71.6) | 58.1 |
| Rat | 52.8 (71.0) | 57.9 |
| Partially sequenced C3 mRNA | | |
| Rabbit | 49.8 (68.2) | 58.3 |
| Xenopus laevis | 49.2 (69.0) | 56.9 |

II. CVF1 and CVF2

Materials and Methods

Materials

Solutions for RNA isolation, λgt11 cloning, and hybridization probe labeling were obtained from Amersham (Skokie, Ill.). In addition, an RNA isolation kit was purchased from Stratagene (La Jolla, Calif.). Reagents for cDNA preparation were obtained either from Gibco-BRL (Gaithersburg, Md.), or from Amersham. Oligo dT-cellulose was from Boehringer Mannheim (Indianapolis, Ind.), or from Invitrogen (San Diego, Calif.). Restriction enzymes were from either Pharmacia, from New England Biolabs (Beverley, Mass.), or from Gibco-BRL. Plasmids pUC18 and pUC19 were purchased from Boehringer Mannheim (Indianapolis, Ind.), while M13mp18 and M13mp19 were purchased from New England Biolabs. DNA modification enzymes were obtained from Pharmacia, New England Biolabs, or Gibco-BRL, and DNA sequencing reagents were obtained from United States Biochemicals (Cleveland, Ohio). Reagents required for PCR amplification of venom gland library ensens were obtained from Perkin-Elmer Cetus. Oligonucleotides for screening the libraries were obtained from Clontech (Palo Alto, Calif.), or were synthesized, using an Applied Biosystems #380 DNA synthesizer. A GeneCleanII kit, containing reagents used for isolation of DNA from agarose gels, and for the purification of PCR products, was obtained from Bio101 (La Jolla, Calif.). Nitrocellulose and nylon membranes for plaque lifts were obtained from Schliecher and Scheull (Keene, N.H.). Rabbit anti-goat IgG (Alkaline Phosphatase conjugated) was obtained from Sigma (St. Louis, Mo.). [$\alpha$-$^{32}$P]dATP, [$\alpha$-$^{32}$P] dCTP, and [$\alpha$-$^{35}$S]dATP were obtained from Amersham.

Methods

RNA Isolation from Cobra Venom Glands

Adult cobras (Naja naja, 1.5–2 meters in length) were anesthetized with katamine (70 $\mu$g/kg i.m.) and with halothane/oxygen by intubation, essentially as described (Vogel, C.-W.., and H. J. Muller-Eberhard. 1985. The cobra complement system: I. The alternative pathway of activation, *Dev. Comp. Immunol.* 9:311). Venom glands were removed and immediately frozen in liquid nitrogen. For RNA preparation, approximately 1 gram of tissue was suspended (while frozen) in 20 ml of a solution of 4M guanidinium thiocyanate and 1.14M $\beta$-mercaptoethanol, and the RNA extracted according to the instructions supplied with the Amersham RNA Extraction Kit. This procedure was based on a published procedure (Han, J. H., C. Stratowa, and W. J. Rutter, 1987. Isolation of full-length putative rat lysophospholipase cDNA using improved methods for mRNA isolation and cDNA cloning. *Biochemistry* 26:1617). Poly-A containing RNA was then isolated by chromatography over oligo-dT cellulose, (Jacobson, A. Purification and fractionation of poly(A)$^{+\ RNA.}$ 1987. In Methods in *Enzymology*, Vol. 152. S. L. Berger and A. R. Kimmel, eds. Academic Press, Orlando, Fla., p. 254). Whole RNA was also prepared using the Stratagene RNA isolation kit, in which the organs were homogenized in the presence of guanidinium isothiocyanate and $\beta$- mercaptoethanol, followed by phenol extraction and isopropanol precipitation (Chomczynski and Sacchi, 1987). Following extraction, poly A+ RNA was prepared by chromatography over oligo-dT cellulose, as described above.

cDNA Synthesis and Cloning

Cobra venom gland cDNA was synthesized (Krug, M. S., and S. L. Berger. 1987. First-strand cDNA synthesis primed with oligo(dT). In *Methods Enzymology*. Vol. 152. S. L. Berger and A. R. Kimmel, eds. Academic Press. Orlando, Fla., p. 316; Gubler, U. 1987. Second-strand cDNA synthesis: mRNA fragments as a primer. In *Methods in Enzymology*, vol. 152. S. L. Berger and A. R. Kimmel. eds. Academic Press, Orlando. Fla. p. 330) using the cDNA synthesis kit from Amersham. cDNA was synthesized using both oligo-dT and random hexamers as the primers. cDNA was then prepared for cloning into $\lambda$gt11 (Wu. R., T. Wu. and A. Ray. 1987. Adaptors, linkers, and methylation. In *Methods in Enzymology*. vol. 152. S. L. Berger and A. R. Kimmel, eds. Academic Press, Orlando, Fla. p. 343), and the recombinant $\lambda$ clones were packaged (Hohn, B., and K. Murray. 1977. Packaging recombinant DNA molecules into bacteriophage particles in vitro. *Proc. Natl. Acad. Sci. USA* 74:3259). *E. coli* Y1090 (r, m+) was used as the host for recombinant $\lambda$gt11.

In addition, cDNA was prepared using Superscript (RNase H$^-$) MMLV Reverse Transcriptase (Gerard et al, 1989). In this case, double stranded cDNA was sized on a 1% Agarose gel in TAE buffer. cDNA greater than 4.5 kb was excised from the gel, and the DNA extracted from the agarose using the GeneCleanII kit from Bio101. This cDNA was then cloned into the plasmid pSPORT (Chen and Segburg, 1985), and the recombinant plasmids transformed into *E. coli* DH5$\alpha$ competent cells.

Screening of $\lambda$gt11 Libraries

Libraries were screened (Young, R. A., and R. W. Davis. 1983. Yeast RNA polymerase II genes: isolation with antibody probes. *Science* 222:778; Huynh, T. V., R. A. Young, and R. W. Davis. 1985, Construction and screening cDNA libraries in $\lambda$gt10 and $\lambda$gt11. In *DNA Cloning* vol. 1. A Practical Approach. D. M. Glover. ed. IRL Press, Oxford, p 49). The primary antibody for screening the venom gland library was goat anti-CVF antiserum. Further plaque purification was done as described above, using successively lower plaque densities. Later screening was done by the hybridization protocol (Wahl, G. M., and S. L. Berger. 1987. Screening colonies of plaques with radioactive nucleic acid probes. In *Methods in Enzymology*, vol. 152. S. L. Berger and A. R. Kimmel, eds. Academic Press, Orlando, Fla., p. 415), using the clones derived from the antibody screening as probes. These probes were labeled with [$\alpha$-$^{32}$P]dATP or [$\alpha$-$^{32}$P]dCTP (Feinberg, A. P., and B. Vogelstein. 1983. A technique for radio-labeling DNA restriction endonuclease fragments to high specific activity. *Anal. Biochem.* 132:6). pSPORT libraries were screened using other cDNA clones as a probe.

Subcloning and DNA Sequence Analysis

Clones containing CVF inserts were grown up on agarose plates and their DNA prepared as described (Maniatis, T., E. F. Fritsch, and J. Sambrook. 1982. *Molecular Cloning—A Laboratory Manual*. Cold Spring Harbor Laboratory, Cold Spring Harbor, N.Y.). Inserts were prepared by EcoR1 digestion, followed by agarose gel electrophoresis. In some cases, $\lambda$gt11 inserts were isolated using the polymerase chain reaction (PCR) on a Savant Model TC49 thermal cycler. In this case, $\lambda$gt11 amplimers from Clontech were used as primers, and the inserts were amplified using the protocol supplied with the amplimers. This consisted of 30 cycles with a 15 sec. denaturing stop at 94° C., 15 sec. of annealing at 58° C. and a 1 minute extension at 72° C. in a 50 $\mu$l reaction mixture containing 10 mM Tris-HCl (pH 8.3), 50 mM KCl, 2 mM MgCl$_2$, 1 mM in each deoxynucleoside triphosphate, 1 $\mu$M in each primer, 1.25 U of Amplitaq® polymerase, and approximately 100 ng DNA to be amplified. Following amplification, the inserts were purified with the Bio101 GeneCleanil kit, the DNA digested with EcoRI, and electrophoresed through an agarose gel. In all cases, fragments were eluted from the gel using the IBI Electroeluter (Model UEA) or by using the GeneCleanII kit from Bio101. The DNA inserts were then ligated into pUC18 (Yanisch-Perron, C.,J. Vieira, and J. Messing, 1985. Improved M13 phage cloning vectors and host strains: nucleotide sequences of the M13 mp18 and pUC19 vectors. *Gene* 33:103) and transformed into *E. coli* JM105 to facilitate the production of large quantities of the insert. Subfragments of the CVF inserts were subcloned into M13mp18 or mp19 (Yanisch-Perron, C.,J. Vieira, and J. Messing, 1985. Improved M13 phage cloning vectors and host strains: nucleotide sequences of the M13 mp18 and pUC19 vectors. *Gene* 33:103) for sequence analysis. Sequencing was performed using the dideoxy-chain termination technique (Sanger, F.,S. Nicklen, and A. R. Coulson. 1977. DNA sequencing with chain terminating inhibitors. *Proc. Natl. Acad. Sci. USA* 74:5463). The Sequenase Version 2.0 sequencing kit from U.S. Biochemicals (Tabor, S., and C. C. Richardson. 1989. Effect of manganese ions on the incorporation of dideoxynucleotides by bacteriophage T7 DNA polymerase and *Escherichia coil* DNA Polymerase 1. *Proc. Natl. Acad. Sci. USA* 86:4076) was used as the source of enzymes, chemicals and primers for sequencing. The DNA sequence was assembled and analyzed using the group of sequence analysis programs written by the Genetics Computer Group of the Wisconsin Biotechnology Center (Devereux, J. R., P. Haeberli, and O. A. Smithies. 1984, Comprehensive set of sequence analysis programs for the VAX. *Nucleic Acids Res.* 12:387).

Results

Screening of the cobra venom gland library Poly-A+ RNA from cobra venom glands was used for the preparation of cDNA that was cloned into the EcoRI site of λgt11. Libraries were prepared from cDNA that had been primed with oligo-dT and with random hexamers. Each library contained at least $5\times10^6$ clones. Initially, $5\times10^5$ clones from the random primed library were screened using CVF specific antisera to detect clones producing CVF containing fusion proteins. In the first round of screening, a single positive clone (CVF5, 1.1 kb, FIG. 13) was isolated. Sequence analysis of this clone revealed that it contained a single open reading frame of 639 nucleotides comprising the C-terminal 213 amino acid residues of the β-chain, and an 3'-untranslated region of 502 nucleotides. This represented approximately 12% of the mature protein.

Figure 13:
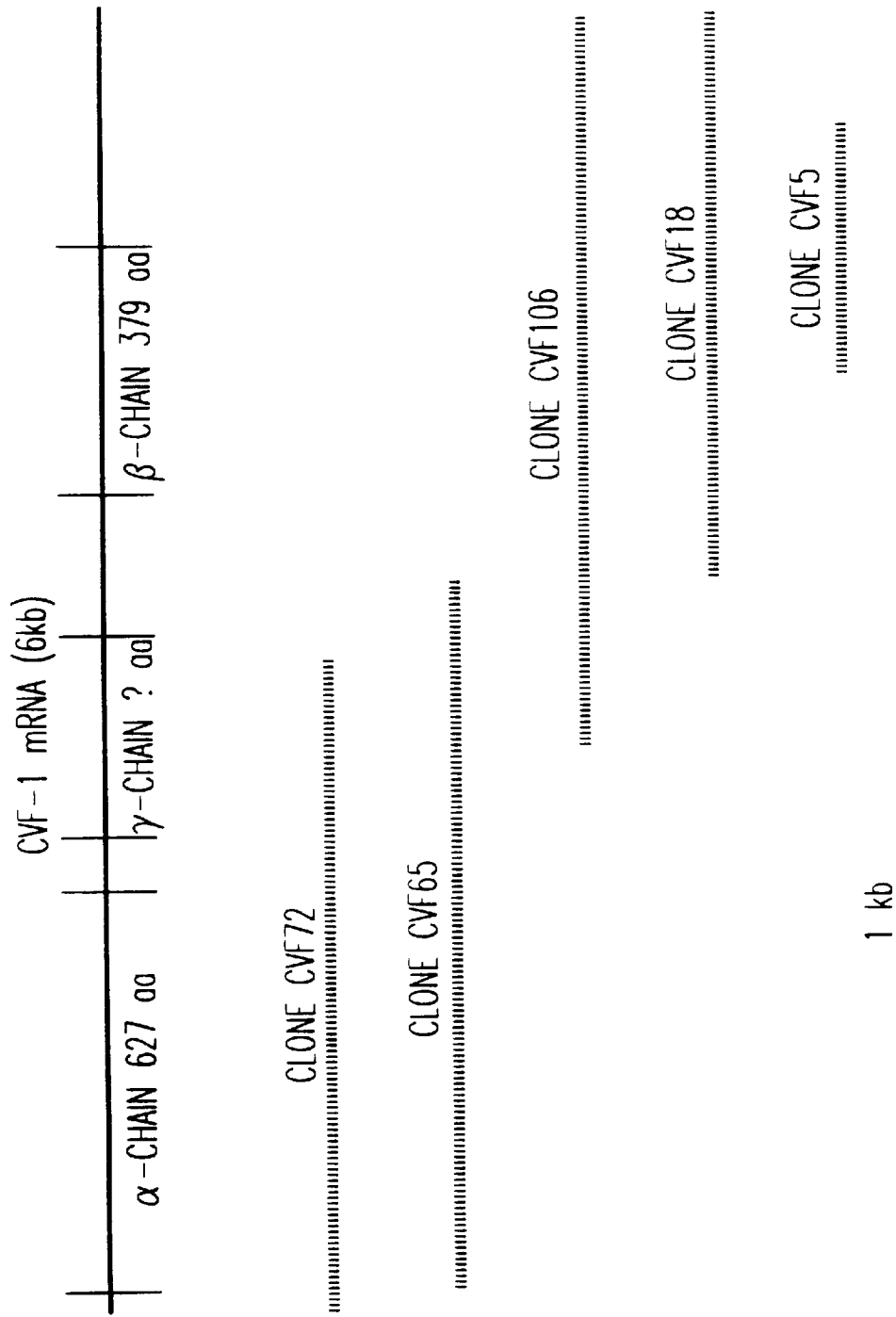
FIG. 13 depicts a map of clones used for the sequencing of CVF1. The upper portion shows a schematic drawing of CVF1 cDNA in which the positions and numbers of amino acid residues of the α-, γ-, and β-chains are indicated. The lower portion shows the relative positions of the five cDNA clones that were used to sequence the molecule.
Figures 19A, 19B:
FIG. 19 provides a comparison of CVF1 and C3 sequences at the factor H and CR2 binding sites. The upper panel shows the factor H orientation site (SEQ ID NOS:58–60). The lower panel shows the discontinuous factor H binding site that includes the CR2 binding site (residues 1180–1191) (SEQ ID NOS:61–63) with the highly conserved LYNVEA sequence in all mammalian C3 proteins. Comparisons were made with a sequence analysis program (Devereux, J. R., P. Haeberli, and O. A. Smithies. 1984. Comprehensive set of sequence analysis programs for the VAX. *Nucleic Acids Res.* 12:387). Identical amino acid residues are boxed and shaded whereas conservative replacements are shaded only. Amino acid residue numbering is based on the CVF1 sequence as shown in FIG. 14. The percent sequence identity and similarity with the cobra sequence is shown on the right.
Figure 20:
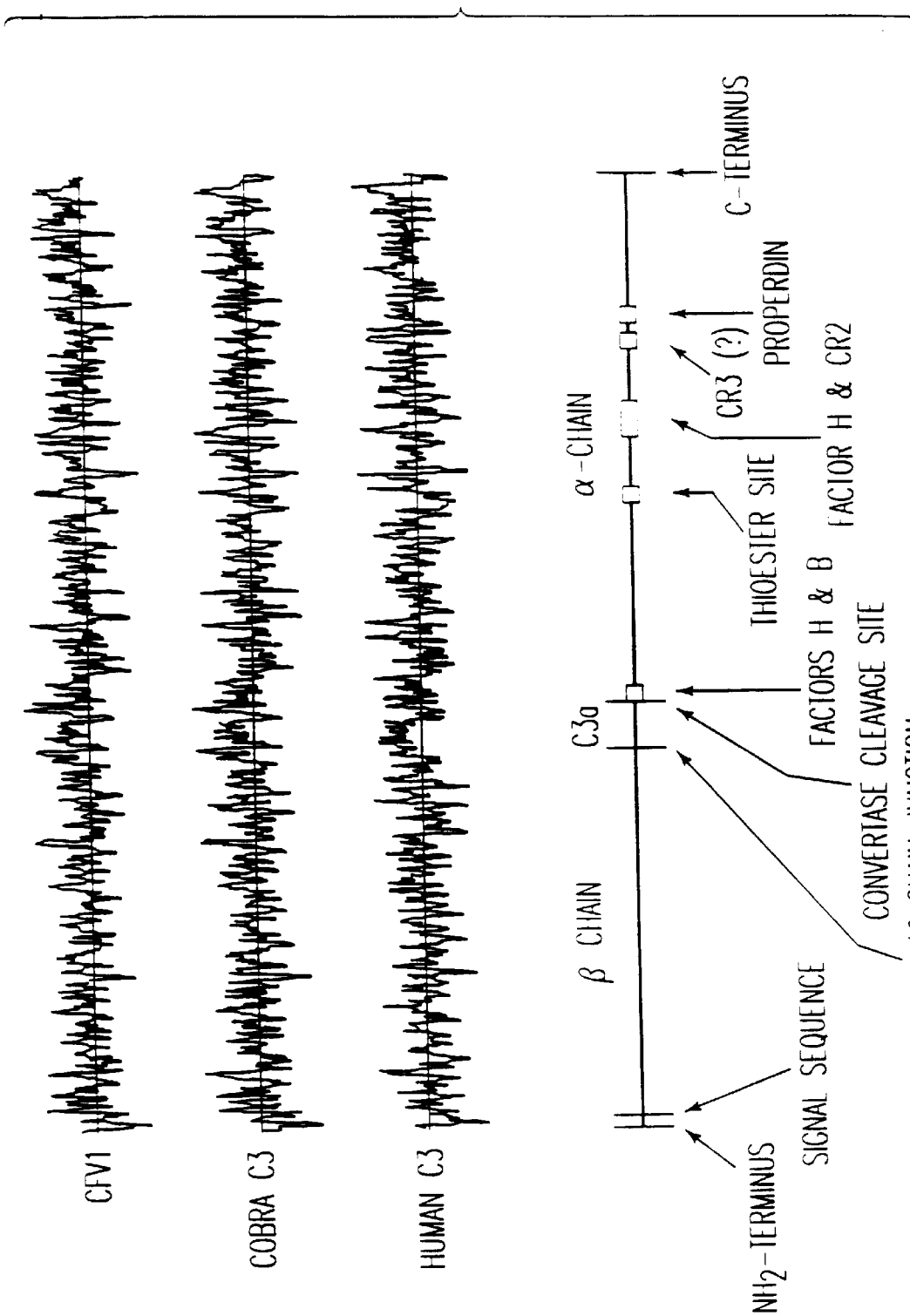
FIG. 20 shows hydophilicity/hydrophobicity plots of CVF1 and cobra and human C3 proteins. The plots were generated using a sequence analysis program (Devereux, J.R., P. Haeberli, and O. A. Smithies. 1984. Comprehensive set of sequence analysis programs for the VAX. *Nucleic Acids Res.* 12:387). Hydrophilic regions are shown above, hydrophobic regions below the line. The locations of functionally important sites are indicated.

To obtain clones representing the rest of the CVF message, several strategies were used. First, the oligo-dT primed library was screened by using hybridization, using CVF5 as a probe. This resulted in the isolation of several clones, one of which (CVF18, 2.6 kb) was used for further sequence analysis. CVF18 contains the 3'-end of the CVF message, with an open reading frame of 1002 nucleotides, and 3' untranslated region of 994 nucleotides. Hybridization screening of an oligo-dT primed venom gland library yielded the clone CVF106 (3.5 kb). Clones containing the 5' end of the CVF cDNA were isolated by screening the random primed λgt11 venom gland library by hybridization, using upstream restriction fragments of sequenced DNA as probes. By this means, two additional clones, CVF65 (3.4 kb) and CVF72 (2.0 kb) were isolated for sequencing. FIG. 13 shows the placement of the clones used for sequencing on the CVF1 mRNA.

Structure of the Cobra Venom Factor cDNA

The CVF1 cDNA is 5924 nucleotides in length. It contains a single open reading frame of 4926 nucleotides, coding for a pre-pro-protein of 1642 amino acid residues (FIG. 14). The cDNA has a 5' untranslated region of 3 nucleotides, and a 3' untranslated region of 994 nucleotides. The start of the poly-A tail has not been found. The coded pre-pro-protein has a signal sequence of 22 residues with a core rich in hydrophobic amino acids. The signal sequence is followed by the 627 amino acid α-chain. The α-chain has three glycosylation sites at residues 131, 136, and 187. Immediately following the C-terminus of the α-chain, there are 4 arginine residues, and a 68 amino acid peptide resembling the C3a anaphylatoxin. There is a single glycosylation site at position 640, though this site is not present in the mature protein. The γ-chain begins at position 710, and extends for approximately 300 amino acid residues. The position of the C-terminus of the γ-chain is unknown, and is apparently heterogeneous. The γ-chain contains no glycosylation sites. The β-chain of CVF begins at position 1242, and extends for 378 residues to the end of the open reading frame. The β-chain contains a single glycosylation site at position 1324.

The G+C composition of the open reading frame for CVF1 is 43.5% (for the whole cDNA: 42.4%). This is approximately the same as cobra C3, though lower than that for sequenced mammalian C3s.

Homology to cobra and other C3 proteins

The CVF1 sequence was compared to C3 sequences from cobra, human, and mouse. CVF1 shows a high degree of homology to cobra C3 at both the nucleic acid and protein level. At the protein level, CVF1 is nearly 85% identical to cobra C3 (greater than 91% similar if conservative replacements are allowed), while the nucleic acid sequences of the two messages are greater than 93% identical. CVF1 also shows a high, though lesser degree of homology to human and mouse C3 sequences. For example, the protein sequence of CVF is nearly 50% identical to that of human C3 (more than 69% similar if conservative replacements are allowed), while the nucleic acid sequence is nearly 57% identical. Comparing the CVF sequence to that of mouse C3, we find that the protein sequences are more than 51% identical (70% similar), and the nucleic acid sequences are nearly 58% identical. Dotplot comparisons of the CVF1 protein sequence with that of cobra and human C3 show that the homologies are spread throughout the molecule.

The homology between CVF1 and mammalian C3s is markedly higher than the average at certain ligand binding sites. For example, at the Factor B binding site, near the Nterminus of the γ-chain, CVF is 90% similar (though it is only 30–40% identical) to the homologous regions of other sequenced C3s (FIG. 15). The homology is also quite high at the properdin binding site (FIG. 16), where greater than 53% of the amino acid residues are identical, and about 80% of the amino acids are similar.

Interestingly, some sites are well conserved, even though they are not present in the mature protein. The best example of this is the sequence around the internal thioester site, where approximately 70% of the sequence is identical, and 80% is similar (FIG. 17). At the Factor H binding site, which is also not present in the mature protein, the homology is not noticeably greater than in the rest of the protein (FIG. 18). However, there is a stretch of 9 amino acid residues in the second portion of the discontinuous Factor H binding site (1192–1200 in CVF1) that is strictly maintained in all of the sequences examined, including rat and rabbit (data not shown), implying conservation of at least part of the Factor H binding site.

Additional clones encoding a distinct CVF were also isolated. The protein encoded by this gene is referred to as CVF2, and a partial sequence for CVF2 is shown in FIG. 22. The clones containing the DNA of CVF2 were obtained in the same series of experiments which gave the DNA for CVF1.

Full length clones of C3 or CVF1 or CVF2 may be obtained by preparing another library containing full length clones or preparing the clones by ligating together the present clones used to sequence C3, CVF1, or CVF2. The method chosen for this is to use PCR to amplify sections of cDNA, and to ligate the fragments together to give a full length clone. Specifically, the CVF1 cDNA sequence has been searched for unique restriction sites at positions approximately one-third and two-thirds of the way through the molecule, and the sites surrounding these sites used as primers for the PCR reaction. In addition, a 3' primer has been designed, containing a string of T residues and sequences with a unique NotI site. A 5' primer also has been designed that contains unique SalI and MluI sites. After amplification of the 3 fragments, each fragment will be cut with the unique enzyme, and the fragments ligated together to form the 6 kb ligation product. This product may be cut with SalI and NotI, ligated into the vector pSport (Gibco/

BRL) and transformed into the *E. coli* strain DH5α. pSport allows transcription of the inserted gene (in either orientation), using either T3 or T7 RNA polymerase. In addition, by cutting with NotI and SAlI, the full length CVF clone may be removed from pSport as a cassette that may be clonable into other expression vectors for expression in bacterial or eukaryotic hosts.

a) Preparation of full length clones of CVF. To prepare full length clones of CVF, approximately 2 kb fragments of CVF are prepared using PCR amplification. Specifically, a 2 kb 5' fragment is prepared using a 5'oligo (SEQ ID NO:77) (GCGTCGACCCACGCGTCCGCCATGGAGAGGATGGC) that represents the 5' 17 nucleotides of the sequenced CVF1 cDNA, along with 18 nucleotides containing unique SalI and MluI sites. The other oligo (SEQ ID NO:78) (CTGCGACGCCTCCGATTTGCAGGC) is complementary to a portion of the sequence 1945 nucleotides from the 5' end, that contains a unique HgaI site. The template is the λ clone, CVF72. The amplification takes place in a Savant TC49 thermal cycler, in a 100 µl reaction that is 10 mM Tris -HCl (pH 8.3), 2 mM $MgCl_2$, 50 mM KCl, 200 µM in each dNTP, 1 µM in each oligonucleotide, 0.1 µg template DNA, and containing 2.5 units of Amplitaq® polymerase. Amplification consists of one cycle of; 94° C. for 120 sec., 45° C. for 45 sec., and 72° C. for 90 sec., followed by 34 cycles of: 94° C. for 45 sec., 45° C. for 45 sec., and 72° C. for 90 sec. After the final cycle the reactions are incubated for a further 10 min at 72° C., and stored at 4° C. until ready for analysis. The other fragments are prepared as above, but with different templates and oligonucleotides. For the central fragment, the 5' oligo is complementary to the 3' oligo for the 5' fragment, while the 3' oligo (SEQ ID NO:79) (GCATTTTCATAATTAATTCTGTACC) is complementary to the CVF1 sequence at position 3878, covering a unique AseI site. The template for the central fragment is a ligation of a 2.5 kb EcoRI fragment from CVF65, and a 1.5 kb EcoRI fragment from pCVF106. The 3' fragment is prepared using, as a 5' oligo, an oligonucleotide complementary to the 3' oligo used for synthesizing the central fragment, while the 3' oligo (SEQ ID NO:80) (GACTAGTTCTAGATCGCGA-GCGGCCGCCCTTTTTTTTTTTT) consists of a unique NotI site followed by a string of 12 T residues. The template for the 3' fragment is pCVF106.

Following preparation of the three fragments, they are purified using the GeneClean kit (Bio101). The 3' and central fragments are both cut with AseI, and ligated together in a 20 µl reaction containing 50 mM Tris-HCl (pH 7.8), 10 mM $MgCl_2$, 10 mM 2-mercaptoethanol, and 1 mM ATP, with each fragment at a concentration of approximately 25 µg/ml. The ligations are performed for 16 hrs at 16° C., and the ligase is heat inactivated by incubation at 65° C. for 15 min., followed by digestion of the ligation mixture with HgaI for 3 hrs at 37° C. The products are separated on a 0.8% agarose gel, and the 4 kb product is isolated from the gel (using the GeneClean kit), and ligated to the 5' fragment (that had been HgaI digested and purified with the GeneClean kit) as described above. The ligation product is cut with SalI and NotI, ligated into NotI and SalI cut pSPORT (Gibco/BRL), and transformed into competent DH5α cells. Proper recombinant clones are identified by restriction mapping and Southern blotting.

To examine the translation products of the putative fully length CVF clones, RNA is prepared in vitro, using transcription by T7 RNA polymerase, followed by translation of the RNA products in a Rabbit Reticulocyte translation system. First, the insert is transcribed in a 20 µl reaction containing 50 mM Tris-HCl (pH 7.5), 10 mM NaCl, 6 mM $MgCl_2$, 2 mM Spermidine, 10 mM DTT, 0.5 mM in each ribonucleotide triphosphate, 0.5 µg CVF containing plasmid, and 10 units of T7 polymerase. The reaction is incubated for 1 hour at 37° C., and the reaction ended by phenol extraction and EtOH precipitation of the RNA. The RNA is resuspended in 20 µl of RNase-free $H_2O$, AND 10 µl will be translated in a 100 µl reaction containing 21 mM Hepes (pH 7.4), 0.5 nM spermidine, 8.5 mM Creatine phosphate, 30 µM in each of 20 amino acids, 2 mM DTT, 80 mM KCl, and 75 µl rabbit reticulocyte lysate (Promega, Madison Wis.). The reaction are incubated for 2 hr at 30° C., and loaded on a 7.5% polyacrylamide gel run in the presence of SDS. The products are analyzed by WEstern blotting, followed by detection with goat anti-CVF antisera. Any clones producing immunoreactive full length protein products are partially sequenced, using the dideoxy-chain termination technique, and any clones without major alterations in sequence are used for in vitro mutagenesis experiments.

b) Expression of CVF clones in eukaryotic cells. Transient expression studies of CVF are done by transfecting CHO of NIH 3T3 cells with CVF sequences cloned into the mammalian expression vector pMT2, containing the SV40 origin of replication and early gene enhancer, the adenovirus major late promoter fused to the adenovirus tripartite leader, a hybrid intron splice site, and the SV40 polyadenylation signal. The CVF cDNA is ligated into the unique EcoRI site that is between the intron and the polyA addition site, and recombinant plasmids are transformed into *E. coli* DH5α. Recombinant clones are checked for the orientation of the insert by restriction analysis. Plasmids containing the CVF insert in the proper orientation are isolated and purified by two rounds of isopycnic $CsCl_2$ gradient centrifugation, and transformed into COS cells by calcium phosphate mediated transfection as described above. The transformed cells are then grown for 24 hrs, and both the cells and the media are assayed for the CVF production by Western analysis as described above.

For production of larger quantities of CVF, the baculovirus expression system is used. In this system, a plasmid containing the gene to be expressed is co-transfected into *Spodopera frugiperda* (Sf9) cells, along with the wild type *Autographica californica* nuclear polyhedrosis virus (AcNPV). Following transfection, a 0.1 to 5% of the wild type viruses acquire the gene to be expressed by homologous recombination. To clone CVF cDNA into baculovirus, the CVF cassette is removed from the original CVF clone by cleavage with SalI and notI, and cloned into the NheI site of the baculovirus cloning vector pJV(NheI). This vector, in addition to having the polyhedron promoter and poly-A addition site, also contains a copy of the β-galactosidase gene attached to the P10 promoter (another very late promoter). Recombinants are screened by restriction analysis and DNA sequencing to find clones with the CVF cDNA in the right orientation. The recombinant pJV(NheI) is then co-transfected with wild type AcNPV into Sf9 cells, using the calcium phosphate precipitation technique. After transfection, the cells are overlayed with 10 ml of 1% agarose (for a 100×15 mm culture plate) diluted with Graces media (Life Technologies, Inc., Gaithersburg, Md.), and are incubated at 27° C. After 3 days, the plates are overlaid with the same agar, containing 150 µg/ml Bluo-gal (Life Technologies, Inc., Gaithersburg, Md.). After a further 6 hr incubation, cells infected with recombinant viruses produce blue plaques from the digestion of the Bluo-gal by β-galactosidase. These plaques are picked, and the phage allowed to elute into Graces medium overnight. This plaque purification technique is repeated until all plaques are blue, indicating that the virus stock is pure.

To express CVF in ACNPV infected Sf9 cells, cells are seeded into 25 cm² flasks at a density of 3×10⁵ cells/flask, and allowed to attach for one hour. The 1 ml of a suspension of recombinant virus is added so that the multiplicity of infection is between 5 and 10, and the infection is allowed to proceed for 1 hr. Then, the virus suspension is replaced with fresh medium, and the cells allowed to grow for 2 to 4 days. The cells are then harvested, and the cells and medium checked for the presence of CVF by SDS acrylamide gel electrophoresis, followed by Western blotting. Once produced, the recombinant CVF is purified by standard methods, using reaction with anti-CVF antisera as an assay for the presence of the protein. Larger quantities of CVF are produced by scaling up the growth of infected cells.

It should be understood that cobra C3, CVF1, or CVF2 may be prepared by expressing a single DNA sequence which encodes, e.g., pre-pro-cobra C3, pro-cobra C3, pre-pro-CVF1, pro-CVF1, pre-pro-CVF2, or pro-CVF2, with any post translational processing being carried out as described above. Alternatively, cobra C3, CVF1 and CVF2 may be prepared by expressing a plurality of DNA sequences which each encodes a fragment of the whole molecule. For example C3 may be prepared by separately preparing the α-chain of C3 and the β-chain of C3, and then incubating the α- and β-chains together. The DNA sequences encoding the fragments may be contained the same or different plasmids and in the same or different transformed hosts.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. An isolated polypeptide having the amino acid sequence from position about 1 to position about 1620 in SEQ ID NO: 45.

2. A method for producing a polypeptide having the amino acid sequence from position about 1 to position about 1620 in SEQ ID NO: 45, comprising:
   culturing a transformed host cell which comprises a heterologous segment of DNA containing a sequence of DNA which encodes said polypeptide; and
   collecting said polypeptide.

3. A method for producing a polypeptide having the amino acid sequence from position about 1 to position about 1620 in SEQ ID NO: 45, comprising:
   culturing a transformed host cell which comprises a heterologous segment of DNA containing the DNA sequence from position about 70 to position about 4929 in SEQ ID NO: 44; and
   collecting said polypeptide.

\* \* \* \* \*

SEQUENCE LISTING ( 1 ) GENERAL INFORMATION:

( i i i ) NUMBER OF SEQUENCES: 81

( 2 ) INFORMATION FOR SEQ ID NO:1:

( i ) SEQUENCE CHARACTERISTICS:
( A ) LENGTH: 5211 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS
( B ) LOCATION: 9..4961

( x i ) SEQUENCE DESCRIPTION: SEQ ID NO:1:

```
GGACTACC ATG GAG GGG ATG GCT CTC TAT CTG GTG GCT GCT CTA TTG ATT      50
         Met Glu Gly Met Ala Leu Tyr Leu Val Ala Ala Leu Leu Ile
          1               5                       10

GGT TTT CCA GGG TCT TCC CAC GGG GCT CTC TAT ACC CTC ATC ACC CCT      98
Gly Phe Pro Gly Ser Ser His Gly Ala Leu Tyr Thr Leu Ile Thr Pro
 15              20                      25                  30

GCT GTT TTG CGA ACA GAC ACA GAA GAG CAA ATT TTG GTG GAG GCC CAT     146
Ala Val Leu Arg Thr Asp Thr Glu Glu Gln Ile Leu Val Glu Ala His
                  35              40                      45

GGA GAC AGT ACT CCA AAA TCG CTT GAC ATC TTT GTT CAT GAT TTT CCA     194
Gly Asp Ser Thr Pro Lys Ser Leu Asp Ile Phe Val His Asp Phe Pro
             50                     55                  60

CGG AAG CAG AAA ACC TTG TTC CAA AGC AGA GTA GAT ATG AAT CAG GCA     242
Arg Lys Gln Lys Thr Leu Phe Gln Ser Arg Val Asp Met Asn Gln Ala
              65                     70                  75

GGA AGC ATG TTT GTC ACT CCA ACT ATA AAG GTT CCT GCA AAA GAA CTG     290
Gly Ser Met Phe Val Thr Pro Thr Ile Lys Val Pro Ala Lys Glu Leu
         80                      85                  90

AAT AAG GAC TCC AAG CAA AAT CAG TAT GTG GTT GTG AAA GTA ACT GGT     338
Asn Lys Asp Ser Lys Gln Asn Gln Tyr Val Val Val Lys Val Thr Gly
 95                     100                     105            110

CCT CAA GTG GCA TTG GAA AAG GTG GTT CTC CTT TCT TAC CAG AGT GGC     386
Pro Gln Val Ala Leu Glu Lys Val Val Leu Leu Ser Tyr Gln Ser Gly
                     115                     120            125

TTT GTG TTC ATC CAG ACA GAT AAA GGC ATC TAT ACA CCA GGC TCT CCA     434
Phe Val Phe Ile Gln Thr Asp Lys Gly Ile Tyr Thr Pro Gly Ser Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
|     |     | 130 |     |     |     |     |     | 135 |     |     |     |     |     | 140 |     |      |
| GTG | CGT | TAT | CGT | GTC | TTT | TCT | GTG | GAT | CAC | AAC | ATG | CAC | AGG | ATG | GAC | 482  |
| Val | Arg | Tyr | Arg | Val | Phe | Ser | Val | Asp | His | Asn | Met | His | Arg | Met | Asp |      |
|     |     | 145 |     |     |     |     |     | 150 |     |     |     |     |     | 155 |     |      |
| AAA | ACT | GTG | ATT | GTC | GAG | TTT | CAG | ACT | CCA | GAA | GGC | ATT | GTT | GTC | AGT | 530  |
| Lys | Thr | Val | Ile | Val | Glu | Phe | Gln | Thr | Pro | Glu | Gly | Ile | Val | Val | Ser |      |
|     |     | 160 |     |     |     |     |     | 165 |     |     |     |     |     | 170 |     |      |
| TCT | AAA | CCA | GTC | AAT | CCA | TCA | GGC | TCG | ATC | CGG | CCT | TAC | AAT | TTA | CCA | 578  |
| Ser | Lys | Pro | Val | Asn | Pro | Ser | Gly | Ser | Ile | Arg | Pro | Tyr | Asn | Leu | Pro |      |
| 175 |     |     |     |     |     | 180 |     |     |     |     |     | 185 |     |     | 190 |      |
| GAG | CTT | GTC | AGT | TTT | GGG | ACA | TGG | AAG | GCT | GTG | GCC | AAA | TAT | GAA | CAT | 626  |
| Glu | Leu | Val | Ser | Phe | Gly | Thr | Trp | Lys | Ala | Val | Ala | Lys | Tyr | Glu | His |      |
|     |     |     |     | 195 |     |     |     |     |     | 200 |     |     |     |     | 205 |      |
| TCA | CCA | GAA | GAG | AGC | TAC | ACT | GCA | TAT | TTT | GAT | GTC | AGA | GAA | TAT | GTG | 674  |
| Ser | Pro | Glu | Glu | Ser | Tyr | Thr | Ala | Tyr | Phe | Asp | Val | Arg | Glu | Tyr | Val |      |
|     |     |     |     | 210 |     |     |     |     |     | 215 |     |     |     |     | 220 |      |
| TTA | CCA | AGC | TTT | GAA | GTC | CGT | CTG | CAA | CCA | TCA | GAT | AAG | TTT | CTT | TAC | 722  |
| Leu | Pro | Ser | Phe | Glu | Val | Arg | Leu | Gln | Pro | Ser | Asp | Lys | Phe | Leu | Tyr |      |
|     |     | 225 |     |     |     |     |     | 230 |     |     |     |     |     | 235 |     |      |
| ATT | GAT | GGG | AAT | AAA | AAT | TTC | CAC | GTG | TCT | ATC | ACT | GCA | AGG | TAC | TTA | 770  |
| Ile | Asp | Gly | Asn | Lys | Asn | Phe | His | Val | Ser | Ile | Thr | Ala | Arg | Tyr | Leu |      |
|     |     | 240 |     |     |     |     |     | 245 |     |     |     |     |     | 250 |     |      |
| TAT | GGA | AAG | AAA | GTG | GAA | GGT | GTG | GCC | TTT | GTC | GTC | TTT | GGA | GTC | AAA | 818  |
| Tyr | Gly | Lys | Lys | Val | Glu | Gly | Val | Ala | Phe | Val | Val | Phe | Gly | Val | Lys |      |
| 255 |     |     |     |     |     | 260 |     |     |     |     |     | 265 |     |     | 270 |      |
| ATA | GAT | GAT | GCT | AAA | AAG | AGT | ATT | CCA | GAC | TCA | CTC | ACG | AGA | ATT | CCG | 866  |
| Ile | Asp | Asp | Ala | Lys | Lys | Ser | Ile | Pro | Asp | Ser | Leu | Thr | Arg | Ile | Pro |      |
|     |     |     |     | 275 |     |     |     |     |     | 280 |     |     |     |     | 285 |      |
| ATT | ATT | GAT | GGA | GAT | GGG | GAA | GCA | ACA | CTA | AAA | AGA | GAT | ACA | CTA | CGT | 914  |
| Ile | Ile | Asp | Gly | Asp | Gly | Glu | Ala | Thr | Leu | Lys | Arg | Asp | Thr | Leu | Arg |      |
|     |     |     |     | 290 |     |     |     |     |     | 295 |     |     |     |     | 300 |      |
| TCC | CGA | TTT | CAA | GAT | CTC | AAT | CAG | CTT | GTT | GGT | CAT | ACT | CTG | TAT | GTA | 962  |
| Ser | Arg | Phe | Gln | Asp | Leu | Asn | Gln | Leu | Val | Gly | His | Thr | Leu | Tyr | Val |      |
|     |     | 305 |     |     |     |     |     | 310 |     |     |     |     |     | 315 |     |      |
| TCT | GTA | ACA | GTG | ATA | ACA | GAA | TCA | GGC | AGT | GAT | ATG | GTA | GTG | ACT | GAG | 1010 |
| Ser | Val | Thr | Val | Ile | Thr | Glu | Ser | Gly | Ser | Asp | Met | Val | Val | Thr | Glu |      |
|     |     | 320 |     |     |     |     |     | 325 |     |     |     |     |     | 330 |     |      |
| CAA | GGC | GGC | ATT | CAT | ATT | GTG | ACA | TCT | CCC | TAT | CAG | ATC | TAC | TTC | ACA | 1058 |
| Gln | Gly | Gly | Ile | His | Ile | Val | Thr | Ser | Pro | Tyr | Gln | Ile | Tyr | Phe | Thr |      |
| 335 |     |     |     |     |     | 340 |     |     |     |     |     | 345 |     |     | 350 |      |
| AAA | ACC | CCC | AAA | TAT | TTC | AAG | CCA | GGA | ATG | CCA | TAT | GAA | CTG | ACG | GTG | 1106 |
| Lys | Thr | Pro | Lys | Tyr | Phe | Lys | Pro | Gly | Met | Pro | Tyr | Glu | Leu | Thr | Val |      |
|     |     |     |     | 355 |     |     |     |     |     | 360 |     |     |     |     | 365 |      |
| TAT | GTT | ACC | AAC | CCT | GAT | GGC | TCA | CCA | GCT | GCC | CAT | GTG | CCA | GTG | GTA | 1154 |
| Tyr | Val | Thr | Asn | Pro | Asp | Gly | Ser | Pro | Ala | Ala | His | Val | Pro | Val | Val |      |
|     |     |     |     | 370 |     |     |     |     |     | 375 |     |     |     |     | 380 |      |
| TCA | GAG | GCC | ATT | CAT | TCT | GAG | GGA | ACC | ACT | TTG | AGT | GAT | GGG | ACT | GCT | 1202 |
| Ser | Glu | Ala | Ile | His | Ser | Glu | Gly | Thr | Thr | Leu | Ser | Asp | Gly | Thr | Ala |      |
|     |     | 385 |     |     |     |     |     | 390 |     |     |     |     |     | 395 |     |      |
| AAG | CTC | ATT | CTG | AAC | ACA | CCA | CTG | AAC | ATT | CAA | AGC | CTA | CCG | ATC | ACT | 1250 |
| Lys | Leu | Ile | Leu | Asn | Thr | Pro | Leu | Asn | Ile | Gln | Ser | Leu | Pro | Ile | Thr |      |
|     |     | 400 |     |     |     |     |     | 405 |     |     |     |     |     | 410 |     |      |
| GTT | AGA | ACT | AAC | CAT | GGA | GAC | CTC | CCA | AGA | GAA | CGC | CAG | GCA | ATA | AAG | 1298 |
| Val | Arg | Thr | Asn | His | Gly | Asp | Leu | Pro | Arg | Glu | Arg | Gln | Ala | Ile | Lys |      |
| 415 |     |     |     |     |     | 420 |     |     |     |     |     | 425 |     |     | 430 |      |
| TCC | ATG | ACA | GCC | ACA | GCC | TAC | CAA | ACC | CAG | GGA | GGG | TCT | GAA | AAC | TAT | 1346 |
| Ser | Met | Thr | Ala | Thr | Ala | Tyr | Gln | Thr | Gln | Gly | Gly | Ser | Glu | Asn | Tyr |      |
|     |     |     |     | 435 |     |     |     |     |     | 440 |     |     |     |     | 445 |      |
| CTT | CAT | GTA | GCC | ATT | ACA | TCT | ACA | GAG | ATT | AAG | CCC | GGA | GAT | AAC | TTA | 1394 |
| Leu | His | Val | Ala | Ile | Thr | Ser | Thr | Glu | Ile | Lys | Pro | Gly | Asp | Asn | Leu |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 450 |     |     |     |     | 455 |     |     |     |     | 460 |     |      |
| CCT | GTC | AAT | TTC | AAT | GTG | AGG | GGC | AAT | GCA | AAT | TCA | CTG | AAC | CAG | ATC | 1442 |
| Pro | Val | Asn | Phe | Asn | Val | Arg | Gly | Asn | Ala | Asn | Ser | Leu | Asn | Gln | Ile |      |
|     |     | 465 |     |     |     |     | 470 |     |     |     |     | 475 |     |     |     |      |
| AAA | TAT | TTC | ACA | TAC | CTC | ATA | TTG | AAT | AAA | GGG | AAG | ATT | TTC | AAG | GTT | 1490 |
| Lys | Tyr | Phe | Thr | Tyr | Leu | Ile | Leu | Asn | Lys | Gly | Lys | Ile | Phe | Lys | Val |      |
|     |     | 480 |     |     |     |     | 485 |     |     |     |     | 490 |     |     |     |      |
| GGC | AGG | CAA | CCC | AGG | AGA | GAT | GGG | CAG | AAT | CTG | GTG | ACC | ATG | AAT | CTG | 1538 |
| Gly | Arg | Gln | Pro | Arg | Arg | Asp | Gly | Gln | Asn | Leu | Val | Thr | Met | Asn | Leu |      |
| 495 |     |     |     |     | 500 |     |     |     |     | 505 |     |     |     |     | 510 |      |
| CAT | ATC | ACT | CCA | GAT | CTC | ATC | CCT | TCC | TTC | CGG | TTT | GTG | GCT | TAC | TAC | 1586 |
| His | Ile | Thr | Pro | Asp | Leu | Ile | Pro | Ser | Phe | Arg | Phe | Val | Ala | Tyr | Tyr |      |
|     |     |     |     | 515 |     |     |     |     | 520 |     |     |     |     | 525 |     |      |
| CAA | GTG | GGA | AAT | AAC | GAA | ATT | GTG | GCT | GAT | TCT | GTC | TGG | GTG | GAT | GTG | 1634 |
| Gln | Val | Gly | Asn | Asn | Glu | Ile | Val | Ala | Asp | Ser | Val | Trp | Val | Asp | Val |      |
|     |     |     |     | 530 |     |     |     |     | 535 |     |     |     |     | 540 |     |      |
| AAG | GAT | ACC | TGC | ATG | GGA | ACG | TTG | GTT | GTG | AAA | GGA | GCG | TCT | TCC | AGA | 1682 |
| Lys | Asp | Thr | Cys | Met | Gly | Thr | Leu | Val | Val | Lys | Gly | Ala | Ser | Ser | Arg |      |
|     |     | 545 |     |     |     |     | 550 |     |     |     |     | 555 |     |     |     |      |
| GAC | GAT | CGA | ATA | CAA | AAG | CCA | GGA | GCT | GCA | ATG | AAA | ATC | AAA | TTG | GAA | 1730 |
| Asp | Asp | Arg | Ile | Gln | Lys | Pro | Gly | Ala | Ala | Met | Lys | Ile | Lys | Leu | Glu |      |
|     |     | 560 |     |     |     |     | 565 |     |     |     |     | 570 |     |     |     |      |
| GGG | GAT | CCA | GGT | GCT | CGG | GTT | GGT | CTT | GTG | GCT | GTG | GAC | AAA | GCA | GTA | 1778 |
| Gly | Asp | Pro | Gly | Ala | Arg | Val | Gly | Leu | Val | Ala | Val | Asp | Lys | Ala | Val |      |
| 575 |     |     |     |     | 580 |     |     |     |     | 585 |     |     |     |     | 590 |      |
| TAT | GTT | CTC | AAT | GAT | AAA | TAT | AAG | ATT | AGC | CAA | GCT | AAG | ATA | TGG | GAC | 1826 |
| Tyr | Val | Leu | Asn | Asp | Lys | Tyr | Lys | Ile | Ser | Gln | Ala | Lys | Ile | Trp | Asp |      |
|     |     |     |     | 595 |     |     |     |     | 600 |     |     |     |     | 605 |     |      |
| ACA | ATA | GAA | AAG | AGT | GAC | TTT | GGC | TGT | ACA | GCT | GGC | AGT | GGC | CAG | AAT | 1874 |
| Thr | Ile | Glu | Lys | Ser | Asp | Phe | Gly | Cys | Thr | Ala | Gly | Ser | Gly | Gln | Asn |      |
|     |     |     | 610 |     |     |     |     | 615 |     |     |     |     | 620 |     |     |      |
| AAT | CTG | GGT | GTG | TTT | GAA | GAT | GCT | GGA | CTG | GCT | CTG | ACA | ACC | AGC | ACT | 1922 |
| Asn | Leu | Gly | Val | Phe | Glu | Asp | Ala | Gly | Leu | Ala | Leu | Thr | Thr | Ser | Thr |      |
|     |     | 625 |     |     |     |     | 630 |     |     |     |     | 635 |     |     |     |      |
| AAT | CTC | AAC | ACC | AAA | CAG | AGA | TCA | GCT | GCA | AAG | TGT | CCT | CAG | CCT | GCA | 1970 |
| Asn | Leu | Asn | Thr | Lys | Gln | Arg | Ser | Ala | Ala | Lys | Cys | Pro | Gln | Pro | Ala |      |
| 640 |     |     |     |     | 645 |     |     |     |     | 650 |     |     |     |     |     |      |
| AAT | CGG | AGG | CGT | CGC | AGT | TCT | GTT | TTG | CTG | CTT | GAC | AGC | AAA | GCA | AGC | 2018 |
| Asn | Arg | Arg | Arg | Arg | Ser | Ser | Val | Leu | Leu | Leu | Asp | Ser | Lys | Ala | Ser |      |
| 655 |     |     |     |     | 660 |     |     |     |     | 665 |     |     |     |     | 670 |      |
| AAA | GCG | GCA | CAG | TTT | CAG | GAT | CAA | GGC | CTG | CGT | AAA | TGC | TGT | GAA | GAT | 2066 |
| Lys | Ala | Ala | Gln | Phe | Gln | Asp | Gln | Gly | Leu | Arg | Lys | Cys | Cys | Glu | Asp |      |
|     |     |     |     | 675 |     |     |     |     | 680 |     |     |     |     | 685 |     |      |
| GGC | ATG | CAT | GAG | AAC | CCC | ATG | GGG | TAC | ACT | TGT | GAA | AAG | CGT | GCA | AAA | 2114 |
| Gly | Met | His | Glu | Asn | Pro | Met | Gly | Tyr | Thr | Cys | Glu | Lys | Arg | Ala | Lys |      |
|     |     |     | 690 |     |     |     |     | 695 |     |     |     |     | 700 |     |     |      |
| TAC | ATC | CAG | GAG | GGA | GAT | GCT | TGT | AAG | GCT | GCC | TTC | CTT | GAA | TGT | TGT | 2162 |
| Tyr | Ile | Gln | Glu | Gly | Asp | Ala | Cys | Lys | Ala | Ala | Phe | Leu | Glu | Cys | Cys |      |
|     |     | 705 |     |     |     |     | 710 |     |     |     |     | 715 |     |     |     |      |
| CAC | TAC | ATC | AAA | GGG | ATC | CGA | GAT | GAA | AAC | CAA | CGG | GAG | AGC | GAG | TTG | 2210 |
| His | Tyr | Ile | Lys | Gly | Ile | Arg | Asp | Glu | Asn | Gln | Arg | Glu | Ser | Glu | Leu |      |
|     |     | 720 |     |     |     |     | 725 |     |     |     |     | 730 |     |     |     |      |
| TTT | CTG | GCA | AGA | AGT | GAT | TTT | GAA | GAT | GAA | CTC | TTT | GGA | GAT | GAC | AAC | 2258 |
| Phe | Leu | Ala | Arg | Ser | Asp | Phe | Glu | Asp | Glu | Leu | Phe | Gly | Asp | Asp | Asn |      |
| 735 |     |     |     |     | 740 |     |     |     |     | 745 |     |     |     |     | 750 |      |
| ATC | ATC | TCC | AGG | TCT | GAT | TTT | CCC | GAG | AGT | TGG | TTG | TGG | CTA | ACA | GAG | 2306 |
| Ile | Ile | Ser | Arg | Ser | Asp | Phe | Pro | Glu | Ser | Trp | Leu | Trp | Leu | Thr | Glu |      |
|     |     |     |     | 755 |     |     |     |     | 760 |     |     |     |     | 765 |     |      |
| GAA | TTG | ACC | GGG | GAG | CCT | AAC | AAT | CAA | GGG | ATT | TCA | AGC | AAG | ACA | GTA | 2354 |
| Glu | Leu | Thr | Gly | Glu | Pro | Asn | Asn | Gln | Gly | Ile | Ser | Ser | Lys | Thr | Val |      |

|   |   |   |   |   |   |   |   |   |   |   |   |   |   |   |   |      |
|---|---|---|---|---|---|---|---|---|---|---|---|---|---|---|---|------|
|   |   |   |   |   | 770 |   |   |   |   | 775 |   |   |   |   | 780 |      |
| CCT | TTT | TAT | CTG | AGG | GAT | TCC | ATC | ACA | ACC | TGG | GAG | TTG | CTG | GCT | GTG | 2402 |
| Pro | Phe | Tyr | Leu | Arg | Asp | Ser | Ile | Thr | Thr | Trp | Glu | Leu | Leu | Ala | Val |      |
|     | 785 |     |     |     |     |     | 790 |     |     |     |     |     | 795 |     |     |      |
| GGC | CTT | TCA | CCC | ACC | AAA | GGG | ATC | TGT | GTG | GCT | GAA | CCG | TAT | GAA | ATA | 2450 |
| Gly | Leu | Ser | Pro | Thr | Lys | Gly | Ile | Cys | Val | Ala | Glu | Pro | Tyr | Glu | Ile |      |
|     | 800 |     |     |     |     | 805 |     |     |     |     |     | 810 |     |     |     |      |
| ACA | GTC | ATG | AAA | GAC | TTC | TTC | ATT | GAT | CTT | CGA | CTG | CCA | TAT | TCA | GTA | 2498 |
| Thr | Val | Met | Lys | Asp | Phe | Phe | Ile | Asp | Leu | Arg | Leu | Pro | Tyr | Ser | Val |      |
| 815 |     |     |     |     | 820 |     |     |     |     | 825 |     |     |     |     | 830 |      |
| GTG | AAG | AAT | GAG | CAG | GTG | GAG | ATT | CGA | GCT | ATT | CTG | TAC | AAC | TAC | GCT | 2546 |
| Val | Lys | Asn | Glu | Gln | Val | Glu | Ile | Arg | Ala | Ile | Leu | Tyr | Asn | Tyr | Ala |      |
|     |     |     |     | 835 |     |     |     |     | 840 |     |     |     |     | 845 |     |      |
| GAC | GAG | GAT | ATT | TAT | GTG | CGA | GTG | GAA | CTG | ATA | TAC | AAC | CCA | GCC | TTC | 2594 |
| Asp | Glu | Asp | Ile | Tyr | Val | Arg | Val | Glu | Leu | Ile | Tyr | Asn | Pro | Ala | Phe |      |
|     |     |     | 850 |     |     |     |     | 855 |     |     |     |     | 860 |     |     |      |
| TGC | AGT | GCT | TCC | ACA | GAA | GGA | CAA | AGA | TAC | CGA | CAG | CAG | TTC | CCA | ATT | 2642 |
| Cys | Ser | Ala | Ser | Thr | Glu | Gly | Gln | Arg | Tyr | Arg | Gln | Gln | Phe | Pro | Ile |      |
|     |     | 865 |     |     |     |     | 870 |     |     |     |     | 875 |     |     |     |      |
| AAA | GCC | CTG | TCC | TCC | AGA | GCA | GTA | CCA | TTT | GTG | ATA | GTC | CCA | TTA | GAG | 2690 |
| Lys | Ala | Leu | Ser | Ser | Arg | Ala | Val | Pro | Phe | Val | Ile | Val | Pro | Leu | Glu |      |
|     | 880 |     |     |     |     | 885 |     |     |     |     |     | 890 |     |     |     |      |
| CAA | GGA | TTG | CAT | GAT | GTT | GAG | GTT | ATA | GCA | AGT | GTC | CGG | GGA | GAG | TTG | 2738 |
| Gln | Gly | Leu | His | Asp | Val | Glu | Val | Ile | Ala | Ser | Val | Arg | Gly | Glu | Leu |      |
| 895 |     |     |     |     | 900 |     |     |     |     | 905 |     |     |     |     | 910 |      |
| GCA | TCA | GAT | GGT | GTG | AGG | AAG | AAA | CTG | AAA | GTT | GTA | CCT | GAA | GGG | GAA | 2786 |
| Ala | Ser | Asp | Gly | Val | Arg | Lys | Lys | Leu | Lys | Val | Val | Pro | Glu | Gly | Glu |      |
|     |     |     |     | 915 |     |     |     |     | 920 |     |     |     |     | 925 |     |      |
| CGG | AAA | AAT | ATT | GTG | ACT | ATT | ATT | GAA | CTG | GAC | CCA | AGT | GTA | AAA | GGA | 2834 |
| Arg | Lys | Asn | Ile | Val | Thr | Ile | Ile | Glu | Leu | Asp | Pro | Ser | Val | Lys | Gly |      |
|     |     |     | 930 |     |     |     |     | 935 |     |     |     |     | 940 |     |     |      |
| GTT | GGT | GGA | ACC | CAG | GAA | CTA | ACG | GTC | ATA | GCC | AAT | AAA | TTA | GAT | GAC | 2882 |
| Val | Gly | Gly | Thr | Gln | Glu | Leu | Thr | Val | Ile | Ala | Asn | Lys | Leu | Asp | Asp |      |
|     |     | 945 |     |     |     |     | 950 |     |     |     |     | 955 |     |     |     |      |
| AAG | GTG | CCT | GAT | ACA | GAA | GTT | GAG | ACC | AGG | ATT | TCT | GTT | CTA | GGT | GAC | 2930 |
| Lys | Val | Pro | Asp | Thr | Glu | Val | Glu | Thr | Arg | Ile | Ser | Val | Leu | Gly | Asp |      |
| 960 |     |     |     |     | 965 |     |     |     |     | 970 |     |     |     |     |     |      |
| CCT | GTG | GCT | CAG | ATT | ATT | GAA | AAC | TCA | ATT | GAT | GGA | AGT | AAA | CTC | AAT | 2978 |
| Pro | Val | Ala | Gln | Ile | Ile | Glu | Asn | Ser | Ile | Asp | Gly | Ser | Lys | Leu | Asn |      |
| 975 |     |     |     |     | 980 |     |     |     |     | 985 |     |     |     |     | 990 |      |
| CAT | CTC | ATT | ATT | ACT | CCT | TCT | GGC | TGT | GGG | GAG | CAA | AAT | ATG | ATC | ACC | 3026 |
| His | Leu | Ile | Ile | Thr | Pro | Ser | Gly | Cys | Gly | Glu | Gln | Asn | Met | Ile | Thr |      |
|     |     |     |     | 995 |     |     |     |     | 1000 |     |     |     |     | 1005 |     |      |
| ATG | ACT | CCA | TCG | GTC | ATT | GCC | ACC | TAC | TAC | TTG | GAC | GCA | ACA | GGG | CAG | 3074 |
| Met | Thr | Pro | Ser | Val | Ile | Ala | Thr | Tyr | Tyr | Leu | Asp | Ala | Thr | Gly | Gln |      |
|     |     |     | 1010 |     |     |     |     | 1015 |     |     |     |     | 1020 |     |     |      |
| TGG | GAG | AAT | CTT | GGT | GTG | GAT | CGC | AGG | ACT | GAA | GCT | ATC | AAA | CAG | ATC | 3122 |
| Trp | Glu | Asn | Leu | Gly | Val | Asp | Arg | Arg | Thr | Glu | Ala | Ile | Lys | Gln | Ile |      |
|     |     |     | 1025 |     |     |     |     | 1030 |     |     |     |     | 1035 |     |     |      |
| ATG | ACT | GGT | TAT | GCC | CAG | CAG | ATG | GTG | TAC | AAG | AAA | GCA | GAT | CAT | TCC | 3170 |
| Met | Thr | Gly | Tyr | Ala | Gln | Gln | Met | Val | Tyr | Lys | Lys | Ala | Asp | His | Ser |      |
|     |     | 1040 |     |     |     |     | 1045 |     |     |     |     | 1050 |     |     |     |      |
| TAT | GCA | GCA | TTT | ACA | AAC | CGT | GCA | TCT | AGT | TCT | TGG | CTA | ACA | GCA | TAT | 3218 |
| Tyr | Ala | Ala | Phe | Thr | Asn | Arg | Ala | Ser | Ser | Ser | Trp | Leu | Thr | Ala | Tyr |      |
| 1055 |     |     |     |     | 1060 |     |     |     |     | 1065 |     |     |     |     | 1070 |      |
| GTG | GTG | AAA | GTC | TTA | GCC | ATG | GCT | TCC | AAC | ATG | GTA | AAA | GAC | ATT | AGC | 3266 |
| Val | Val | Lys | Val | Leu | Ala | Met | Ala | Ser | Asn | Met | Val | Lys | Asp | Ile | Ser |      |
|     |     |     |     | 1075 |     |     |     |     | 1080 |     |     |     |     | 1085 |     |      |
| CAT | GAA | ATT | ATT | TGT | GGA | GGT | GTG | AAA | TGG | CTC | ATT | CTG | AAC | AGG | CAA | 3314 |
| His | Glu | Ile | Ile | Cys | Gly | Gly | Val | Lys | Trp | Leu | Ile | Leu | Asn | Arg | Gln |      |

|  |  |
|---|---|
| CAA CCA GAT GGA GTG TTC AAA GAA AAT GCC CCT GTG ATC CAT GGA GAA<br>Gln Pro Asp Gly Val Phe Lys Glu Asn Ala Pro Val Ile His Gly Glu<br>1105                                1110                             1115 | 3362 |
| ATG CTG GGA GGA ACT AAA GGT GCT GAA CCA GAA GCA TCT TTA ACA GCA<br>Met Leu Gly Gly Thr Lys Gly Ala Glu Pro Glu Ala Ser Leu Thr Ala<br>            1120                              1125                             1130 | 3410 |
| TTC ATT GTG ACT GCA TTA TTG GAA TCC AGA TCA GTC TGC AAA GAA CAA<br>Phe Ile Val Thr Ala Leu Leu Glu Ser Arg Ser Val Cys Lys Glu Gln<br>1135                                1140                             1145                             1150 | 3458 |
| ATC AAT ATT CTA GAC AGC AGC ATC AAT AAG GCC ACA GAT TAT TTA CTC<br>Ile Asn Ile Leu Asp Ser Ser Ile Asn Lys Ala Thr Asp Tyr Leu Leu<br>                       1155                             1160                             1165 | 3506 |
| AAA AAG TAT GAG AAA CTG CAA AGG CCT TAC ACT ACA GCC CTC ACA GCC<br>Lys Lys Tyr Glu Lys Leu Gln Arg Pro Tyr Thr Thr Ala Leu Thr Ala<br>               1170                             1175                             1180 | 3554 |
| TAT GCT TTG GCT GCT GCA GAC CGA CTC AAT GAT GAC AGG GTA CTC ATG<br>Tyr Ala Leu Ala Ala Ala Asp Arg Leu Asn Asp Asp Arg Val Leu Met<br>                       1185                             1190                             1195 | 3602 |
| GCA GCA TCA ACA GGA AGG AAT CGT TGG GAA GAA TAT AAT GCT CGC ACC<br>Ala Ala Ser Thr Gly Arg Asn Arg Trp Glu Glu Tyr Asn Ala Arg Thr<br>1200                                1205                                1210 | 3650 |
| CAT AAT ATT GAA GGC ACT TCC TAT GCC TTG TTG GCC CTG CTG AAA ATG<br>His Asn Ile Glu Gly Thr Ser Tyr Ala Leu Leu Ala Leu Leu Lys Met<br>1215                                1220                             1225                             1230 | 3698 |
| AAG AAA TTT GCT GAG GTC GGT CCT GTA GTC AGA TGG CTG ATA GAT CAG<br>Lys Lys Phe Ala Glu Val Gly Pro Val Val Arg Trp Leu Ile Asp Gln<br>                       1235                             1240                             1245 | 3746 |
| AAA TAT TAT GGG GGA ACA TAT GGA CAA ACC CAA GCA ACA GTT ATG GTG<br>Lys Tyr Tyr Gly Gly Thr Tyr Gly Gln Thr Gln Ala Thr Val Met Val<br>                       1250                             1255                             1260 | 3794 |
| TTT CAA GCT CTT GCT GAA TAT GAG ATT CAG ATG CCT ACC CAT CAG GAC<br>Phe Gln Ala Leu Ala Glu Tyr Glu Ile Gln Met Pro Thr His Gln Asp<br>            1265                              1270                             1275 | 3842 |
| TTA AAT TTA GAT ATT TCT ATT AAA CTG CCA GAA CGA GAA GTA CCT GAA<br>Leu Asn Leu Asp Ile Ser Ile Lys Leu Pro Glu Arg Glu Val Pro Glu<br>1280                                1285                                1290 | 3890 |
| AGG TAC AGC ATT AAT GAT AGA AAT GCT GTC CAG GCC CGG ACA GTA GAG<br>Arg Tyr Ser Ile Asn Asp Arg Asn Ala Val Gln Ala Arg Thr Val Glu<br>1295                                1300                                1305                             1310 | 3938 |
| ACC AAA CTC AAC GAA GAC TTC ACT GTG TCA GCA TCA GGT GAT GGA AAA<br>Thr Lys Leu Asn Glu Asp Phe Thr Val Ser Ala Ser Gly Asp Gly Lys<br>                       1315                             1320                             1325 | 3986 |
| GCA ACA ATG ACC ATT TTG ACG TCT TAT AAT GCA CAA TTG AGG GAG GAT<br>Ala Thr Met Thr Ile Leu Thr Val Tyr Asn Ala Gln Leu Arg Glu Asp<br>                       1330                             1335                             1340 | 4034 |
| GCA AAT GTT TGC AAC AAA TTC CAT CTT GAT GTT TCT GTT GAA AAC GTC<br>Ala Asn Val Cys Asn Lys Phe His Leu Asp Val Ser Val Glu Asn Val<br>                       1345                             1350                             1355 | 4082 |
| GAA TTG AAC TTA AAA CAG GCA AAG GGA GGC AAG GCA GCC CTC AGG CTT<br>Glu Leu Asn Leu Lys Gln Ala Lys Gly Gly Lys Ala Ala Leu Arg Leu<br>1360                                1365                                1370 | 4130 |
| AAA ATC TGC ACT AGG TAT CTG GGA GAA GTT GAT TCT ACA ATG ACA ATA<br>Lys Ile Cys Thr Arg Tyr Leu Gly Glu Val Asp Ser Thr Met Thr Ile<br>1375                                1380                                1385                             1390 | 4178 |
| ATT GAT ATT TCT ATG CTG ACT GGT TTT TTC CCT GAT GCT GAA GAC CTT<br>Ile Asp Ile Ser Met Leu Thr Gly Phe Phe Pro Asp Ala Glu Asp Leu<br>                       1395                             1400                             1405 | 4226 |
| AAA AGG CTT TCT AAC GGA GTG GAC AGA TAC ATC TCC AAG TTT GAA ATT<br>Lys Arg Leu Ser Asn Gly Val Asp Arg Tyr Ile Ser Lys Phe Glu Ile | 4274 |

-continued

```
                  1410                      1415                        1420
GAC   AAT   AAT   ATG   GCT   CAG   AAA   GGA   ACT   GTT   GTC   ATT   TAC   TTA   GAC   AAG        4322
Asp   Asn   Asn   Met   Ala   Gln   Lys   Gly   Thr   Val   Val   Ile   Tyr   Leu   Asp   Lys
            1425                      1430                        1435

GTC   TCC   CAC   TCT   GAA   GAT   GAA   TGC   CTG   CAC   TTT   AAG   ATT   CAC   AAG   CAT        4370
Val   Ser   His   Ser   Glu   Asp   Glu   Cys   Leu   His   Phe   Lys   Ile   His   Lys   His
            1440                      1445                        1450

TTT   GAA   GTT   GGC   TTC   ATT   CAG   CCA   GGA   TCA   GTC   AAG   GTG   TAC   AGC   TAC        4418
Phe   Glu   Val   Gly   Phe   Ile   Gln   Pro   Gly   Ser   Val   Lys   Val   Tyr   Ser   Tyr
1455                      1460                      1465                        1470

TAC   AAT   CTA   GAT   GAA   CAA   TGT   ACC   AAG   TTC   TAC   CAT   CCA   GAT   AAA   GAA        4466
Tyr   Asn   Leu   Asp   Glu   Gln   Cys   Thr   Lys   Phe   Tyr   His   Pro   Asp   Lys   Glu
            1475                      1480                        1485

ACA   GGT   CTT   CTC   AAT   AAG   ATA   TGT   CAT   GGT   AAC   ATT   TGC   CGA   TGT   GCA        4514
Thr   Gly   Leu   Leu   Asn   Lys   Ile   Cys   His   Gly   Asn   Ile   Cys   Arg   Cys   Ala
            1490                      1495                        1500

GAA   GAA   ACC   TGT   TCC   TTG   CTC   AAC   CAG   CAG   AAA   AAG   ATT   GAT   CTT   CAA        4562
Glu   Glu   Thr   Cys   Ser   Leu   Leu   Asn   Gln   Gln   Lys   Lys   Ile   Asp   Leu   Gln
            1505                      1510                        1515

TTA   CGA   ATT   CAA   AAA   GCC   TGC   GCG   CAA   AAT   GTG   GAT   TAT   GTC   TAC   AAA        4610
Leu   Arg   Ile   Gln   Lys   Ala   Cys   Ala   Gln   Asn   Val   Asp   Tyr   Val   Tyr   Lys
1520                      1525                      1530

ACC   AAG   CTG   CTT   CGA   ATA   GAA   GAA   AAA   GAT   GGT   AAT   GAT   ATC   TAT   TTC        4658
Thr   Lys   Leu   Leu   Arg   Ile   Glu   Glu   Lys   Asp   Gly   Asn   Asp   Ile   Tyr   Phe
1535                      1540                      1545                        1550

ATG   GAT   GTT   TTA   GAA   GTT   ATT   AAA   GGA   GGC   ACT   GAC   CGA   AAT   GCA   CAA        4706
Met   Asp   Val   Leu   Glu   Val   Ile   Lys   Gly   Gly   Thr   Asp   Arg   Asn   Ala   Gln
            1555                      1560                        1565

GCA   AAA   GCC   CGC   CAG   TAT   GTA   AGT   CAA   AGG   AAA   TGC   CAG   GAG   GCT   TTG        4754
Ala   Lys   Ala   Arg   Gln   Tyr   Val   Ser   Gln   Arg   Lys   Cys   Gln   Glu   Ala   Leu
            1570                      1575                        1580

AAT   CTG   AAG   CTG   GAT   AAT   GAT   TAT   CTG   ATC   TGG   GGT   CTC   AGC   AGT   GAC        4802
Asn   Leu   Lys   Leu   Asp   Asn   Asp   Tyr   Leu   Ile   Trp   Gly   Leu   Ser   Ser   Asp
            1585                      1590                        1595

CTG   TGG   CCC   ATG   AAA   GAT   GAT   ATC   TCC   TAC   CTC   ATT   ACA   AAG   AAC   ACC        4850
Leu   Trp   Pro   Met   Lys   Asp   Asp   Ile   Ser   Tyr   Leu   Ile   Thr   Lys   Asn   Thr
1600                      1605                      1610

TGG   ATT   GAG   AGA   TGG   CCA   AAT   GAA   GAT   GAA   TGC   CAG   GAT   GAA   GAA   TTC        4898
Trp   Ile   Glu   Arg   Trp   Pro   Asn   Glu   Asp   Glu   Cys   Gln   Asp   Glu   Glu   Phe
1615                      1620                      1625                        1630

CAG   AAT   TTG   TGT   GAT   GAC   TTT   GCT   CAG   TTG   TCC   AAT   ACA   CTG   ACT   ATT        4946
Gln   Asn   Leu   Cys   Asp   Asp   Phe   Ala   Gln   Leu   Ser   Asn   Thr   Leu   Thr   Ile
                  1635                      1640                        1645

TTT   GGC   TGC   CCT   ACT   TAAAAGTTCA   GAAGAATCAA   TGATAGGAAG   AAAATTCTCA             5001
Phe   Gly   Cys   Pro   Thr
                  1650

GAAGACAGAT   TTTTGAGCCA   ATACATATAT   GTTACTTTGC   CTCTTGATTT   TTTTTAGTT                   5061

TTTTATCATT   TTGCTCTGCT   GTTTTCCTTC   ACAATTGTTT   ATACAGAAAA   TAAATAATTG                  5121

ATTTCTTACT   TTGAAAAAAT   GGAACTCTCT   GATTTGGGTT   TTCCAGATGT   GCCAAAATGA                  5181

CAACTCTAAT   AAATGACTTG   AGGAAAAAAA                                                         5211
```

( 2 ) INFORMATION FOR SEQ ID NO:2:

( i ) SEQUENCE CHARACTERISTICS:
        ( A ) LENGTH: 1651 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Gly Met Ala Leu Tyr Leu Val Ala Ala Leu Leu Ile Gly Phe
 1               5                  10                  15

Pro Gly Ser Ser His Gly Ala Leu Tyr Thr Leu Ile Thr Pro Ala Val
            20                  25                  30

Leu Arg Thr Asp Thr Glu Glu Gln Ile Leu Val Glu Ala His Gly Asp
        35                  40                  45

Ser Thr Pro Lys Ser Leu Asp Ile Phe Val His Asp Phe Pro Arg Lys
    50                  55                  60

Gln Lys Thr Leu Phe Gln Ser Arg Val Asp Met Asn Gln Ala Gly Ser
65                  70                  75                  80

Met Phe Val Thr Pro Thr Ile Lys Val Pro Ala Lys Glu Leu Asn Lys
                85                  90                  95

Asp Ser Lys Gln Asn Gln Tyr Val Val Lys Val Thr Gly Pro Gln
            100                 105                 110

Val Ala Leu Glu Lys Val Val Leu Leu Ser Tyr Gln Ser Gly Phe Val
            115                 120                 125

Phe Ile Gln Thr Asp Lys Gly Ile Tyr Thr Pro Gly Ser Pro Val Arg
130                 135                 140

Tyr Arg Val Phe Ser Val Asp His Asn Met His Arg Met Asp Lys Thr
145                 150                 155                 160

Val Ile Val Glu Phe Gln Thr Pro Glu Gly Ile Val Val Ser Lys
                165                 170                 175

Pro Val Asn Pro Ser Gly Ser Ile Arg Pro Tyr Asn Leu Pro Glu Leu
            180                 185                 190

Val Ser Phe Gly Thr Trp Lys Ala Val Ala Lys Tyr Glu His Ser Pro
            195                 200                 205

Glu Glu Ser Tyr Thr Ala Tyr Phe Asp Val Arg Glu Tyr Val Leu Pro
210                 215                 220

Ser Phe Glu Val Arg Leu Gln Pro Ser Asp Lys Phe Leu Tyr Ile Asp
225                 230                 235                 240

Gly Asn Lys Asn Phe His Val Ser Ile Thr Ala Arg Tyr Leu Tyr Gly
                245                 250                 255

Lys Lys Val Glu Gly Val Ala Phe Val Phe Gly Val Lys Ile Asp
            260                 265                 270

Asp Ala Lys Lys Ser Ile Pro Asp Ser Leu Thr Arg Ile Pro Ile Ile
        275                 280                 285

Asp Gly Asp Gly Glu Ala Thr Leu Lys Arg Asp Thr Leu Arg Ser Arg
    290                 295                 300

Phe Gln Asp Leu Asn Gln Leu Val Gly His Thr Leu Tyr Val Ser Val
305                 310                 315                 320

Thr Val Ile Thr Glu Ser Gly Ser Asp Met Val Val Thr Glu Gln Gly
                325                 330                 335

Gly Ile His Ile Val Thr Ser Pro Tyr Gln Ile Tyr Phe Thr Lys Thr
            340                 345                 350

Pro Lys Tyr Phe Lys Pro Gly Met Pro Tyr Glu Leu Thr Val Tyr Val
        355                 360                 365

Thr Asn Pro Asp Gly Ser Pro Ala Ala His Val Pro Val Val Ser Glu
    370                 375                 380

Ala Ile His Ser Glu Gly Thr Thr Leu Ser Asp Gly Thr Ala Lys Leu
385                 390                 395                 400

Ile Leu Asn Thr Pro Leu Asn Ile Gln Ser Leu Pro Ile Thr Val Arg
                405                 410                 415
```

-continued

| | | | | | | | | | | | | | | | |
|---|---|---|---|---|---|---|---|---|---|---|---|---|---|---|---|
|Thr|Asn|His|Gly|Asp|Leu|Pro|Arg|Glu|Arg|Gln|Ala|Ile|Lys|Ser|Met|
| | | |420| | | |425| | | |  |430| | | |
|Thr|Ala|Thr|Ala|Tyr|Gln|Thr|Gln|Gly|Gly|Ser|Glu|Asn|Tyr|Leu|His|
| | |435| | | |440| | | | |445| | | | |
|Val|Ala|Ile|Thr|Ser|Thr|Glu|Ile|Lys|Pro|Gly|Asp|Asn|Leu|Pro|Val|
|450| | | | |455| | | | |460| | | | | |
|Asn|Phe|Asn|Val|Arg|Gly|Asn|Ala|Asn|Ser|Leu|Asn|Gln|Ile|Lys|Tyr|
|465| | | |470| | | | |475| | | | | |480|
|Phe|Thr|Tyr|Leu|Ile|Leu|Asn|Lys|Gly|Lys|Ile|Phe|Lys|Val|Gly|Arg|
| | | | |485| | | |490| | | | | |495| |
|Gln|Pro|Arg|Arg|Asp|Gly|Gln|Asn|Leu|Val|Thr|Met|Asn|Leu|His|Ile|
| | | |500| | | | |505| | | | |510| | |
|Thr|Pro|Asp|Leu|Ile|Pro|Ser|Phe|Arg|Phe|Val|Ala|Tyr|Tyr|Gln|Val|
| | |515| | | | |520| | | | |525| | | |
|Gly|Asn|Asn|Glu|Ile|Val|Ala|Asp|Ser|Val|Trp|Val|Asp|Val|Lys|Asp|
| |530| | | | |535| | | | |540| | | | |
|Thr|Cys|Met|Gly|Thr|Leu|Val|Val|Lys|Gly|Ala|Ser|Ser|Arg|Asp|Asp|
|545| | | | |550| | | | |555| | | | |560|
|Arg|Ile|Gln|Lys|Pro|Gly|Ala|Ala|Met|Lys|Ile|Lys|Leu|Glu|Gly|Asp|
| | | | |565| | | | |570| | | | |575| |
|Pro|Gly|Ala|Arg|Val|Gly|Leu|Val|Ala|Val|Asp|Lys|Ala|Val|Tyr|Val|
| | | |580| | | | |585| | | | |590| | |
|Leu|Asn|Asp|Lys|Tyr|Lys|Ile|Ser|Gln|Ala|Lys|Ile|Trp|Asp|Thr|Ile|
| | |595| | | | |600| | | | |605| | | |
|Glu|Lys|Ser|Asp|Phe|Gly|Cys|Thr|Ala|Gly|Ser|Gly|Gln|Asn|Asn|Leu|
| |610| | | | |615| | | | |620| | | | |
|Gly|Val|Phe|Glu|Asp|Ala|Gly|Leu|Ala|Leu|Thr|Thr|Ser|Thr|Asn|Leu|
|625| | | | |630| | | | |635| | | | |640|
|Asn|Thr|Lys|Gln|Arg|Ser|Ala|Ala|Lys|Cys|Pro|Gln|Pro|Ala|Asn|Arg|
| | | | |645| | | | |650| | | | |655| |
|Arg|Arg|Arg|Ser|Ser|Val|Leu|Leu|Leu|Asp|Ser|Lys|Ala|Ser|Lys|Ala|
| | | |660| | | | |665| | | | |670| | |
|Ala|Gln|Phe|Gln|Asp|Gln|Gly|Leu|Arg|Lys|Cys|Cys|Glu|Asp|Gly|Met|
| | |675| | | | |680| | | | |685| | | |
|His|Glu|Asn|Pro|Met|Gly|Tyr|Thr|Cys|Glu|Lys|Arg|Ala|Lys|Tyr|Ile|
| |690| | | | |695| | | | |700| | | | |
|Gln|Glu|Gly|Asp|Ala|Cys|Lys|Ala|Ala|Phe|Leu|Glu|Cys|Cys|His|Tyr|
|705| | | | |710| | | | |715| | | | |720|
|Ile|Lys|Gly|Ile|Arg|Asp|Glu|Asn|Gln|Arg|Glu|Ser|Glu|Leu|Phe|Leu|
| | | | |725| | | | |730| | | | |735| |
|Ala|Arg|Ser|Asp|Phe|Glu|Asp|Glu|Leu|Phe|Gly|Asp|Asp|Asn|Ile|Ile|
| | | |740| | | | |745| | | | |750| | |
|Ser|Arg|Ser|Asp|Phe|Pro|Glu|Ser|Trp|Leu|Trp|Leu|Thr|Glu|Glu|Leu|
| | |755| | | | |760| | | | |765| | | |
|Thr|Gly|Glu|Pro|Asn|Asn|Gln|Gly|Ile|Ser|Ser|Lys|Thr|Val|Pro|Phe|
| |770| | | | |775| | | | |780| | | | |
|Tyr|Leu|Arg|Asp|Ser|Ile|Thr|Thr|Trp|Glu|Leu|Leu|Ala|Val|Gly|Leu|
|785| | | | |790| | | | |795| | | | |800|
|Ser|Pro|Thr|Lys|Gly|Ile|Cys|Val|Ala|Glu|Pro|Tyr|Glu|Ile|Thr|Val|
| | | | |805| | | | |810| | | | |815| |
|Met|Lys|Asp|Phe|Phe|Ile|Asp|Leu|Arg|Leu|Pro|Tyr|Ser|Val|Val|Lys|
| | | |820| | | | |825| | | | |830| | |
|Asn|Glu|Gln|Val|Glu|Ile|Arg|Ala|Ile|Leu|Tyr|Asn|Tyr|Ala|Asp|Glu|
| | |835| | | | |840| | | | |845| | | |

```
Asp Ile Tyr Val Arg Val Glu Leu Ile Tyr Asn Pro Ala Phe Cys Ser
    850                 855                 860

Ala Ser Thr Glu Gly Gln Arg Tyr Arg Gln Phe Pro Ile Lys Ala
865                 870                 875                 880

Leu Ser Ser Arg Ala Val Pro Phe Val Ile Val Pro Leu Glu Gln Gly
                885                 890                 895

Leu His Asp Val Glu Val Ile Ala Ser Val Arg Gly Glu Leu Ala Ser
                900                 905                 910

Asp Gly Val Arg Lys Lys Leu Lys Val Val Pro Glu Gly Glu Arg Lys
                915                 920                 925

Asn Ile Val Thr Ile Ile Glu Leu Asp Pro Ser Val Lys Gly Val Gly
                930                 935                 940

Gly Thr Gln Glu Leu Thr Val Ile Ala Asn Lys Leu Asp Asp Lys Val
945                 950                 955                 960

Pro Asp Thr Glu Val Glu Thr Arg Ile Ser Val Leu Gly Asp Pro Val
                965                 970                 975

Ala Gln Ile Ile Glu Asn Ser Ile Asp Gly Ser Lys Leu Asn His Leu
                980                 985                 990

Ile Ile Thr Pro Ser Gly Cys Gly Glu Gln Asn Met Ile Thr Met Thr
                995                 1000                1005

Pro Ser Val Ile Ala Thr Tyr Tyr Leu Asp Ala Thr Gly Gln Trp Glu
                1010                1015                1020

Asn Leu Gly Val Asp Arg Arg Thr Glu Ala Ile Lys Gln Ile Met Thr
1025                1030                1035                1040

Gly Tyr Ala Gln Gln Met Val Tyr Lys Lys Ala Asp His Ser Tyr Ala
                1045                1050                1055

Ala Phe Thr Asn Arg Ala Ser Ser Ser Trp Leu Thr Ala Tyr Val Val
                1060                1065                1070

Lys Val Leu Ala Met Ala Ser Asn Met Val Lys Asp Ile Ser His Glu
                1075                1080                1085

Ile Ile Cys Gly Gly Val Lys Trp Leu Ile Leu Asn Arg Gln Gln Pro
                1090                1095                1100

Asp Gly Val Phe Lys Glu Asn Ala Pro Val Ile His Gly Glu Met Leu
1105                1110                1115                1120

Gly Gly Thr Lys Gly Ala Glu Pro Glu Ala Ser Leu Thr Ala Phe Ile
                1125                1130                1135

Val Thr Ala Leu Leu Glu Ser Arg Ser Val Cys Lys Glu Gln Ile Asn
                1140                1145                1150

Ile Leu Asp Ser Ser Ile Asn Lys Ala Thr Asp Tyr Leu Leu Lys Lys
                1155                1160                1165

Tyr Glu Lys Leu Gln Arg Pro Tyr Thr Thr Ala Leu Thr Ala Tyr Ala
1170                1175                1180

Leu Ala Ala Ala Asp Arg Leu Asn Asp Asp Arg Val Leu Met Ala Ala
1185                1190                1195                1200

Ser Thr Gly Arg Asn Arg Trp Glu Glu Tyr Asn Ala Arg Thr His Asn
                1205                1210                1215

Ile Glu Gly Thr Ser Tyr Ala Leu Leu Ala Leu Leu Lys Met Lys Lys
                1220                1225                1230

Phe Ala Glu Val Gly Pro Val Val Arg Trp Leu Ile Asp Gln Lys Tyr
                1235                1240                1245

Tyr Gly Gly Thr Tyr Gly Gln Thr Gln Ala Thr Val Met Val Phe Gln
1250                1255                1260

Ala Leu Ala Glu Tyr Glu Ile Gln Met Pro Thr His Gln Asp Leu Asn
```

-continued

```
1265                1270                1275                1280
Leu  Asp  Ile  Ser  Ile  Lys  Leu  Pro  Glu  Arg  Glu  Val  Pro  Glu  Arg  Tyr
               1285                     1290                     1295
Ser  Ile  Asn  Asp  Arg  Asn  Ala  Val  Gln  Ala  Arg  Thr  Val  Glu  Thr  Lys
               1300                     1305                     1310
Leu  Asn  Glu  Asp  Phe  Thr  Val  Ser  Ala  Ser  Gly  Asp  Gly  Lys  Ala  Thr
               1315                     1320                     1325
Met  Thr  Ile  Leu  Thr  Val  Tyr  Asn  Ala  Gln  Leu  Arg  Glu  Asp  Ala  Asn
               1330                     1335                     1340
Val  Cys  Asn  Lys  Phe  His  Leu  Asp  Val  Ser  Val  Glu  Asn  Val  Glu  Leu
1345                     1350                     1355                     1360
Asn  Leu  Lys  Gln  Ala  Lys  Gly  Gly  Lys  Ala  Ala  Leu  Arg  Leu  Lys  Ile
               1365                     1370                     1375
Cys  Thr  Arg  Tyr  Leu  Gly  Glu  Val  Asp  Ser  Thr  Met  Thr  Ile  Ile  Asp
               1380                     1385                     1390
Ile  Ser  Met  Leu  Thr  Gly  Phe  Phe  Pro  Asp  Ala  Glu  Asp  Leu  Lys  Arg
               1395                     1400                     1405
Leu  Ser  Asn  Gly  Val  Asp  Arg  Tyr  Ile  Ser  Lys  Phe  Glu  Ile  Asp  Asn
1410                     1415                     1420
Asn  Met  Ala  Gln  Lys  Gly  Thr  Val  Val  Ile  Tyr  Leu  Asp  Lys  Val  Ser
1425                     1430                     1435                     1440
His  Ser  Glu  Asp  Glu  Cys  Leu  His  Phe  Lys  Ile  His  Lys  His  Phe  Glu
               1445                     1450                     1455
Val  Gly  Phe  Ile  Gln  Pro  Gly  Ser  Val  Lys  Val  Tyr  Ser  Tyr  Tyr  Asn
               1460                     1465                     1470
Leu  Asp  Glu  Gln  Cys  Thr  Lys  Phe  Tyr  His  Pro  Asp  Lys  Glu  Thr  Gly
               1475                     1480                     1485
Leu  Leu  Asn  Lys  Ile  Cys  His  Gly  Asn  Ile  Cys  Arg  Cys  Ala  Glu  Glu
               1490                     1495                     1500
Thr  Cys  Ser  Leu  Leu  Asn  Gln  Gln  Lys  Lys  Ile  Asp  Leu  Gln  Leu  Arg
1505                     1510                     1515                     1520
Ile  Gln  Lys  Ala  Cys  Ala  Gln  Asn  Val  Asp  Tyr  Val  Tyr  Lys  Thr  Lys
               1525                     1530                     1535
Leu  Leu  Arg  Ile  Glu  Glu  Lys  Asp  Gly  Asn  Asp  Ile  Tyr  Phe  Met  Asp
               1540                     1545                     1550
Val  Leu  Glu  Val  Ile  Lys  Gly  Gly  Thr  Asp  Arg  Asn  Ala  Gln  Ala  Lys
               1555                     1560                     1565
Ala  Arg  Gln  Tyr  Val  Ser  Gln  Arg  Lys  Cys  Gln  Glu  Ala  Leu  Asn  Leu
               1570                     1575                     1580
Lys  Leu  Asp  Asn  Asp  Tyr  Leu  Ile  Trp  Gly  Leu  Ser  Ser  Asp  Leu  Trp
1585                     1590                     1595                     1600
Pro  Met  Lys  Asp  Asp  Ile  Ser  Tyr  Leu  Ile  Thr  Lys  Asn  Thr  Trp  Ile
               1605                     1610                     1615
Glu  Arg  Trp  Pro  Asn  Glu  Asp  Glu  Cys  Gln  Asp  Glu  Glu  Phe  Gln  Asn
               1620                     1625                     1630
Leu  Cys  Asp  Asp  Phe  Ala  Gln  Leu  Ser  Asn  Thr  Leu  Thr  Ile  Phe  Gly
               1635                     1640                     1645
Cys  Pro  Thr
1650
```

( 2 ) INFORMATION FOR SEQ ID NO:3:

( i ) SEQUENCE CHARACTERISTICS:
        ( A ) LENGTH: 15 amino acids
        ( B ) TYPE: amino acid (D) TOPOLOGY: linear (ii) MOLECULE TYPE: peptide (vi) ORIGINAL SOURCE:
 (A) ORGANISM: Naja naja (xi) SEQUENCE DESCRIPTION: SEQ ID NO:3:

Cys Pro Gln Pro Ala Asn Arg Arg Arg Ser Ser Val Leu Leu
1               5               10                      15

(2) INFORMATION FOR SEQ ID NO:4:

(i) SEQUENCE CHARACTERISTICS:
  (A) LENGTH: 14 amino acids
  (B) TYPE: amino acid
  (D) TOPOLOGY: linear (ii) MOLECULE TYPE: peptide (vi) ORIGINAL SOURCE:
  (A) ORGANISM: Homo sapiens (xi) SEQUENCE DESCRIPTION: SEQ ID NO:4:

Cys Pro Gln Pro Ala Ala Arg Arg Arg Arg Ser Val Gln Leu
1               5               10

(2) INFORMATION FOR SEQ ID NO:5:

(i) SEQUENCE CHARACTERISTICS:
  (A) LENGTH: 14 amino acids
  (B) TYPE: amino acid
  (D) TOPOLOGY: linear (ii) MOLECULE TYPE: peptide (xi) SEQUENCE DESCRIPTION: SEQ ID NO:5:

Cys Pro Gln Pro Ala Ala Arg Arg Arg Arg Ser Val Gln Leu
1               5               10

(2) INFORMATION FOR SEQ ID NO:6:

(i) SEQUENCE CHARACTERISTICS:
  (A) LENGTH: 14 amino acids
  (B) TYPE: amino acid
  (D) TOPOLOGY: linear (ii) MOLECULE TYPE: peptide (xi) SEQUENCE DESCRIPTION: SEQ ID NO:6:

Cys Thr Lys Pro Ala Ala Arg Arg Arg Arg Ser Val Gln Leu
1               5               10

(2) INFORMATION FOR SEQ ID NO:7:

(i) SEQUENCE CHARACTERISTICS:
  (A) LENGTH: 14 amino acids
  (B) TYPE: amino acid
  (D) TOPOLOGY: linear (ii) MOLECULE TYPE: peptide (vi) ORIGINAL SOURCE:
  (A) ORGANISM: Naja naja (xi) SEQUENCE DESCRIPTION: SEQ ID NO:7:

Leu Ala Arg Ser Asp Phe Glu Asp Glu Leu Phe Gly Asp Asp
1               5               10

(2) INFORMATION FOR SEQ ID NO:8:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( v i ) ORIGINAL SOURCE:
  ( A ) ORGANISM: Homo sapiens ( x i ) SEQUENCE DESCRIPTION: SEQ ID NO:8:

Leu Ala Arg Ser Asn Leu Glu Asp Glu Ile Ile Ala Glu Glu
 1               5                  10

( 2 ) INFORMATION FOR SEQ ID NO:9:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:9:

Leu Ala Arg Ser Glu Leu Glu Glu Asp Ile Ile Pro Gly Gly
 1               5                  10

( 2 ) INFORMATION FOR SEQ ID NO:10:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:10:

Leu Ala Arg Ser Asp Val Asp Glu Asp Ile Ile Pro Glu Glu
 1               5                  10

( 2 ) INFORMATION FOR SEQ ID NO:11:

( i ) SEQUENCE CHARACTERISTICS:
    ( A ) LENGTH: 26 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Naja naja ( x i ) SEQUENCE DESCRIPTION: SEQ ID NO:11:

Leu Ile Ile Thr Pro Ser Gly Cys Gly Glu Gln Asn Met Ile Thr Met
 1               5                  10                      15

Thr Pro Ser Val Ile Ala Thr Tyr Tyr Leu
             20              25

( 2 ) INFORMATION FOR SEQ ID NO:12:

( i ) SEQUENCE CHARACTERISTICS:
    ( A ) LENGTH: 26 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Homo sapiens (x i) SEQUENCE DESCRIPTION: SEQ ID NO:12:

Leu Ile Val Thr Pro Ser Gly Cys Gly Glu Gln Asn Met Ile Gly Met
1               5                   10                      15

Thr Pro Thr Val Ile Ala Tyr His Tyr Leu
                20              25

(2) INFORMATION FOR SEQ ID NO:13:

(i) SEQUENCE CHARACTERISTICS:
  (A) LENGTH: 26 amino acids
  (B) TYPE: amino acid
  (D) TOPOLOGY: linear (i i) MOLECULE TYPE: peptide (x i) SEQUENCE DESCRIPTION: SEQ ID NO:13:

Leu Ile Val Thr Pro Ser Gly Cys Gly Glu Gln Asn Met Ile Gly Met
1               5                   10                      15

Thr Pro Thr Val Ile Ala Val His Tyr Leu
                20              25

(2) INFORMATION FOR SEQ ID NO:14:

(i) SEQUENCE CHARACTERISTICS:
  (A) LENGTH: 26 amino acids
  (B) TYPE: amino acid
  (D) TOPOLOGY: linear (i i) MOLECULE TYPE: peptide (x i) SEQUENCE DESCRIPTION: SEQ ID NO:14:

Leu Ile Val Thr Gly Ser Gly Cys Gly Glu Gln Asn Met Ile Ala Met
1               5                   10                      15

Thr His Thr Val Ile Ala Val His Tyr Leu
                20              25

(2) INFORMATION FOR SEQ ID NO:15:

(i) SEQUENCE CHARACTERISTICS:
  (A) LENGTH: 10 amino acids
  (B) TYPE: amino acid
  (D) TOPOLOGY: linear (i i) MOLECULE TYPE: peptide (v i) ORIGINAL SOURCE:
  (A) ORGANISM: Naja naja (x i) SEQUENCE DESCRIPTION: SEQ ID NO:15:

Glu Asp Glu Leu Phe Gly Asp Asp Asn Ile
1               5                   10

(2) INFORMATION FOR SEQ ID NO:16:

(i) SEQUENCE CHARACTERISTICS:
  (A) LENGTH: 10 amino acids
  (B) TYPE: amino acid
  (D) TOPOLOGY: linear (i i) MOLECULE TYPE: peptide (v i) ORIGINAL SOURCE:
  (A) ORGANISM: Homo sapiens (x i) SEQUENCE DESCRIPTION: SEQ ID NO:16:

Asp Glu Asp Ile Ile Ala Glu Glu Asn Ile
1               5                   10

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Glu  Glu  Asp  Ile  Ile  Pro  Glu  Glu  Asp  Ile
1                  5                       10
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Asp  Glu  Asp  Ile  Ile  Pro  Glu  Glu  Asp  Ile
1                  5                       10
```

( 2 ) INFORMATION FOR SEQ ID NO:19:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Naja naja ( x i ) SEQUENCE DESCRIPTION: SEQ ID NO:19:

```
Ser  Asp  Phe  Glu  Asp  Glu  Leu  Phe  Gly  Asp  Asp  Asn  Ile  Ile  Ser  Arg
1                  5                            10                           15
Ser  Asp  Phe  Pro  Glu
                   20
```

( 2 ) INFORMATION FOR SEQ ID NO:20:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:20:

```
Ser  Asn  Leu  Asp  Glu  Asp  Ile  Ile  Ala  Glu  Glu  Asn  Ile  Val  Ser  Arg
1                  5                            10                           15
Ser  Glu  Phe  Pro  Glu
                   20
```

( 2 ) INFORMATION FOR SEQ ID NO:21:

( i ) SEQUENCE CHARACTERISTICS:
        ( A ) LENGTH: 21 amino acids
        ( B ) TYPE: amino acid
        ( D ) TOPOLOGY: linear (ii) MOLECULE TYPE: peptide (xi) SEQUENCE DESCRIPTION: SEQ ID NO:21:

Ser Glu Leu Glu Glu Asp Ile Ile Pro Glu Asp Ile Ile Ser Arg
1               5                       10                      15

Ser His Phe Pro Gln
            20

(2) INFORMATION FOR SEQ ID NO:22:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO:22:

Ser Asp Val Asp Glu Asp Ile Ile Pro Glu Asp Ile Ile Ser Arg
1               5                       10                      15

Ser His Phe Pro Glu
            20

(2) INFORMATION FOR SEQ ID NO:23:

(i) SEQUENCE CHARACTERISTICS:
    (A) LENGTH: 63 amino acids
    (B) TYPE: amino acid
    (D) TOPOLOGY: linear (ii) MOLECULE TYPE: peptide (vi) ORIGINAL SOURCE:
    (A) ORGANISM: Naja naja (xi) SEQUENCE DESCRIPTION: SEQ ID NO:23:

Val Leu Met Ala Ala Ser Thr Gly Arg Asn Arg Trp Glu Glu Tyr Asn
1               5                       10                      15

Ala Arg Thr His Asn Ile Glu Gly Thr Ser Tyr Ala Leu Leu Ala Leu
                20                      25                      30

Leu Lys Met Lys Lys Phe Ala Glu Val Gly Pro Val Val Arg Trp Leu
            35                      40                      45

Ile Asp Gln Lys Tyr Tyr Gly Gly Thr Tyr Gly Gln Thr Gln Ala
        50                      55                      60

(2) INFORMATION FOR SEQ ID NO:24:

(i) SEQUENCE CHARACTERISTICS:
    (A) LENGTH: 63 amino acids
    (B) TYPE: amino acid
    (D) TOPOLOGY: linear (ii) MOLECULE TYPE: peptide (vi) ORIGINAL SOURCE:
    (A) ORGANISM: Homo sapiens (xi) SEQUENCE DESCRIPTION: SEQ ID NO:24:

Lys Phe Leu Thr Thr Ala Lys Asp Lys Asn Arg Trp Glu Asp Pro Gly
1               5                       10                      15

Lys Gln Leu Tyr Asn Val Glu Ala Thr Ser Tyr Ala Leu Leu Ala Leu
                20                      25                      30

Leu Gln Leu Lys Asp Phe Asp Phe Val Pro Pro Val Val Arg Trp Leu
            35                      40                      45

Asn Glu Gln Arg Tyr Tyr Gly Gly Gly Tyr Gly Ser Thr Gln Ala (2) INFORMATION FOR SEQ ID NO:25:

(i) SEQUENCE CHARACTERISTICS:
        (A) LENGTH: 63 amino acids
        (B) TYPE: amino acid
        (D) TOPOLOGY: linear (ii) MOLECULE TYPE: peptide (xi) SEQUENCE DESCRIPTION: SEQ ID NO:25:

```
Lys Phe Leu Asn Thr Ala Lys Asp Arg Asn Arg Trp Glu Glu Pro Asp
 1               5                  10                  15
Gln Gln Leu Tyr Asn Val Glu Ala Thr Ser Tyr Ala Leu Leu Ala Leu
                20                  25                  30
Leu Leu Leu Lys Asp Phe Asp Ser Val Pro Pro Val Val Arg Trp Leu
            35                  40                  45
Asn Glu Gln Arg Tyr Tyr Gly Gly Gly Tyr Gly Ser Thr Gln Ala
            50                  55                  60
```

(2) INFORMATION FOR SEQ ID NO:26:

(i) SEQUENCE CHARACTERISTICS:
        (A) LENGTH: 63 amino acids
        (B) TYPE: amino acid
        (D) TOPOLOGY: linear (ii) MOLECULE TYPE: peptide (xi) SEQUENCE DESCRIPTION: SEQ ID NO:26:

```
Lys Phe Leu Asn Thr Ala Lys Asp Arg Asn Arg Trp Glu Glu Pro Gly
 1               5                  10                  15
Gln Gln Leu Tyr Asn Val Glu Ala Thr Ser Tyr Ala Leu Leu Ala Leu
                20                  25                  30
Leu Leu Leu Lys Asp Phe Asp Ser Val Pro Pro Val Val Arg Trp Leu
            35                  40                  45
Asn Asp Glu Arg Tyr Tyr Gly Gly Gly Tyr Gly Ser Thr Gln Ala
            50                  55                  60
```

(2) INFORMATION FOR SEQ ID NO:27:

(i) SEQUENCE CHARACTERISTICS:
        (A) LENGTH: 63 amino acids
        (B) TYPE: amino acid
        (D) TOPOLOGY: linear (ii) MOLECULE TYPE: peptide (vi) ORIGINAL SOURCE:
        (A) ORGANISM: Oryctolagus cuniculus (xi) SEQUENCE DESCRIPTION: SEQ ID NO:27:

```
Lys Phe Leu Ser Lys Ala Lys Glu Lys Asn Arg Trp Glu Glu Pro Gly
 1               5                  10                  15
Gln Arg Leu Tyr Asn Val Glu Ala Ser Ser Tyr Ala Leu Leu Ala Leu
                20                  25                  30
Leu Leu Leu Arg Asp Phe Asp Ser Val Pro Pro Val Val Arg Trp Leu
            35                  40                  45
Asn Glu Gln Arg Tyr Tyr Gly Gly Gly Tyr Gly Ser Thr Gln Ala
            50                  55                  60
```

(2) INFORMATION FOR SEQ ID NO:28:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Naja naja ( x i ) SEQUENCE DESCRIPTION: SEQ ID NO:28:

```
Val Asp Arg Tyr Ile Ser Lys Phe Glu Ile Asp Asn Asn Met Ala Gln
1               5                   10                  15

Lys Gly Thr Val Val Ile Tyr Leu Asp Lys Val Ser His Ser
                20                  25                  30
```

( 2 ) INFORMATION FOR SEQ ID NO:29:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:29:

```
Val Asp Arg Tyr Ile Ser Lys Tyr Glu Leu Asp Lys Ala Phe Ser Asp
1               5                   10                  15

Arg Asn Thr Leu Ile Ile Tyr Leu Asp Lys Val Ser His Ser
                20                  25                  30
```

( 2 ) INFORMATION FOR SEQ ID NO:30:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

```
Val Asp Arg Tyr Ile Ser Lys Tyr Glu Met Asn Lys Ala Phe Ser Asn
1               5                   10                  15

Lys Asn Thr Leu Ile Ile Tyr Leu Glu Lys Ile Ser His Thr
                20                  25                  30
```

( 2 ) INFORMATION FOR SEQ ID NO:31:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

```
Val Asp Arg Tyr Ile Ser Lys Tyr Glu Met Asp Lys Ala Phe Ser Asn
1               5                   10                  15

Lys Asn Thr Leu Ile Ile Tyr Leu Glu Lys Ile Ser His Ser
                20                  25                  30
```

( 2 ) INFORMATION FOR SEQ ID NO:32:

( i ) SEQUENCE CHARACTERISTICS:
        ( A ) LENGTH: 30 amino acids (B) TYPE: amino acid
(D) TOPOLOGY: linear (ii) MOLECULE TYPE: peptide (vi) ORIGINAL SOURCE:
(A) ORGANISM: Oryctolagus cuniculus (xi) SEQUENCE DESCRIPTION: SEQ ID NO:32:

| Val | Asp | Arg | Tyr | Ile | Ser | Lys | Tyr | Glu | Leu | Asn | Lys | Ala | Phe | Ser | Asn |
|---|---|---|---|---|---|---|---|---|---|---|---|---|---|---|---|
| 1 | | | | 5 | | | | | 10 | | | | | 15 | |

| Lys | Asn | Thr | Leu | Ile | Ile | Tyr | Leu | Asp | Lys | Ile | Ser | His | Ser |
|---|---|---|---|---|---|---|---|---|---|---|---|---|---|
| | | | 20 | | | | | 25 | | | | | 30 |

(2) INFORMATION FOR SEQ ID NO:33:

(i) SEQUENCE CHARACTERISTICS:
(A) LENGTH: 30 amino acids
(B) TYPE: amino acid
(D) TOPOLOGY: linear (ii) MOLECULE TYPE: peptide (xi) SEQUENCE DESCRIPTION: SEQ ID NO:33:

| Val | Asp | Lys | Tyr | Ile | Ser | Lys | Tyr | Glu | Val | Asn | Lys | Gly | Ala | Asn | Asp |
|---|---|---|---|---|---|---|---|---|---|---|---|---|---|---|---|
| 1 | | | | 5 | | | | | 10 | | | | | 15 | |

| Lys | Gly | Thr | Leu | Ile | Leu | Tyr | Leu | Asp | Lys | Val | Ser | His | Ile |
|---|---|---|---|---|---|---|---|---|---|---|---|---|---|
| | | | 20 | | | | | 25 | | | | | 30 |

(2) INFORMATION FOR SEQ ID NO:34:

(i) SEQUENCE CHARACTERISTICS:
(A) LENGTH: 21 amino acids
(B) TYPE: amino acid
(D) TOPOLOGY: linear (ii) MOLECULE TYPE: peptide (vi) ORIGINAL SOURCE:
(A) ORGANISM: Naja naja (xi) SEQUENCE DESCRIPTION: SEQ ID NO:34:

| Cys | His | Tyr | Ile | Lys | Gly | Ile | Arg | Asp | Glu | Asn | Gln | Arg | Glu | Ser | Glu |
|---|---|---|---|---|---|---|---|---|---|---|---|---|---|---|---|
| 1 | | | | 5 | | | | | 10 | | | | | 15 | |

| Leu | Phe | Leu | Ala | Arg |
|---|---|---|---|---|
| | | | 20 | |

(2) INFORMATION FOR SEQ ID NO:35:

(i) SEQUENCE CHARACTERISTICS:
(A) LENGTH: 21 amino acids
(B) TYPE: amino acid
(D) TOPOLOGY: linear (ii) MOLECULE TYPE: peptide (vi) ORIGINAL SOURCE:
(A) ORGANISM: Homo sapiens (xi) SEQUENCE DESCRIPTION: SEQ ID NO:35:

| Cys | Asn | Tyr | Ile | Thr | Glu | Leu | Arg | Arg | Gln | His | Ala | Arg | Ala | Ser | His |
|---|---|---|---|---|---|---|---|---|---|---|---|---|---|---|---|
| 1 | | | | 5 | | | | | 10 | | | | | 15 | |

| Leu | Gly | Leu | Ala | Arg |
|---|---|---|---|---|
| | | | 20 | |

(2) INFORMATION FOR SEQ ID NO:36:

(i) SEQUENCE CHARACTERISTICS:

(A) LENGTH: 21 amino acids
(B) TYPE: amino acid
(D) TOPOLOGY: linear (ii) MOLECULE TYPE: peptide (xi) SEQUENCE DESCRIPTION: SEQ ID NO:36:

Cys Asn His Ile Thr Lys Leu Arg Glu Gln His Arg Arg Asp His Val
1               5                   10                  15

Leu Gly Leu Ala Arg
            20

(2) INFORMATION FOR SEQ ID NO:37:

(i) SEQUENCE CHARACTERISTICS:
(A) LENGTH: 21 amino acids
(B) TYPE: amino acid
(D) TOPOLOGY: linear (ii) MOLECULE TYPE: peptide (xi) SEQUENCE DESCRIPTION: SEQ ID NO:37:

Cys Asn Tyr Ile Thr Lys Leu Arg Glu Gln His Arg Arg Asp His Val
1               5                   10                  15

Leu Gly Leu Ala Arg
            20

(2) INFORMATION FOR SEQ ID NO:38:

(i) SEQUENCE CHARACTERISTICS:
(A) LENGTH: 21 amino acids
(B) TYPE: amino acid
(D) TOPOLOGY: linear (ii) MOLECULE TYPE: peptide (vi) ORIGINAL SOURCE:
(A) ORGANISM: Naja naja (xi) SEQUENCE DESCRIPTION: SEQ ID NO:38:

Ala Leu Arg Leu Lys Ile Cys Thr Arg Tyr Leu Gly Glu Val Asp Ser
1               5                   10                  15

Thr Met Thr Ile Ile
            20

(2) INFORMATION FOR SEQ ID NO:39:

(i) SEQUENCE CHARACTERISTICS:
(A) LENGTH: 21 amino acids
(B) TYPE: amino acid
(D) TOPOLOGY: linear (ii) MOLECULE TYPE: peptide (vi) ORIGINAL SOURCE:
(A) ORGANISM: Homo sapiens (xi) SEQUENCE DESCRIPTION: SEQ ID NO:39:

Thr Met Ile Leu Glu Ile Cys Thr Arg Tyr Arg Gly Asp Gln Asp Ala
1               5                   10                  15

Thr Met Ser Ile Leu
            20

(2) INFORMATION FOR SEQ ID NO:40:

(i) SEQUENCE CHARACTERISTICS:
(A) LENGTH: 21 amino acids
(B) TYPE: amino acid

-continued (D) TOPOLOGY: linear (ii) MOLECULE TYPE: peptide (xi) SEQUENCE DESCRIPTION: SEQ ID NO:40:

| Thr | Met | Phe | Leu | Glu | Ile | Cys | Thr | Lys | Tyr | Leu | Gly | Asp | Val | Asp | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Met | Ser | Ile | Leu |
|-----|-----|-----|-----|-----|
|     |     |     | 20  |     |

(2) INFORMATION FOR SEQ ID NO:41:

(i) SEQUENCE CHARACTERISTICS:
       (A) LENGTH: 21 amino acids
       (B) TYPE: amino acid
       (D) TOPOLOGY: linear (ii) MOLECULE TYPE: peptide (xi) SEQUENCE DESCRIPTION: SEQ ID NO:41:

| Ser | Met | Ile | Leu | Asp | Ile | Cys | Thr | Arg | Tyr | Leu | Gly | Asp | Val | Asp | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Met | Ser | Ile | Leu |
|-----|-----|-----|-----|-----|
|     |     |     | 20  |     |

(2) INFORMATION FOR SEQ ID NO:42:

(i) SEQUENCE CHARACTERISTICS:
       (A) LENGTH: 21 amino acids
       (B) TYPE: amino acid
       (D) TOPOLOGY: linear (ii) MOLECULE TYPE: peptide (vi) ORIGINAL SOURCE:
       (A) ORGANISM: Oryctolagus cuniculus (xi) SEQUENCE DESCRIPTION: SEQ ID NO:42:

| Thr | Met | Ile | Leu | Gly | His | Cys | Thr | Arg | Tyr | Leu | Gly | Asp | Glu | Asp | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Met | Ser | Ile | Leu |
|-----|-----|-----|-----|-----|
|     |     |     | 20  |     |

(2) INFORMATION FOR SEQ ID NO:43:

(i) SEQUENCE CHARACTERISTICS:
       (A) LENGTH: 21 amino acids
       (B) TYPE: amino acid
       (D) TOPOLOGY: linear (ii) MOLECULE TYPE: peptide (xi) SEQUENCE DESCRIPTION: SEQ ID NO:43:

| Thr | Val | Ser | Ile | Glu | Ala | Cys | Ala | Arg | His | Leu | Lys | Asn | Val | Asp | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Met | Ser | Ile | Ile |
|-----|-----|-----|-----|-----|
|     |     |     | 20  |     |

(2) INFORMATION FOR SEQ ID NO:44:

(i) SEQUENCE CHARACTERISTICS:
       (A) LENGTH: 5924 base pairs
       (B) TYPE: nucleic acid
       (C) STRANDEDNESS: unknown
       (D) TOPOLOGY: unknown (ii) MOLECULE TYPE: DNA (genomic)

( i x ) FEATURE:
  ( A ) NAME/KEY: sig_peptide
  ( B ) LOCATION: 4..69

( i x ) FEATURE:
  ( A ) NAME/KEY: mat_peptide
  ( B ) LOCATION: 70..4929

( i x ) FEATURE:
  ( A ) NAME/KEY: CDS
  ( B ) LOCATION: 4..4929

( x i ) SEQUENCE DESCRIPTION: SEQ ID NO:44:

| | | | | | | | | | | | | | | | | |
|---|---|---|---|---|---|---|---|---|---|---|---|---|---|---|---|---|
| CCC | ATG | GAG | AGG | ATG | GCT | CTC | TAT | CTG | GTG | GCT | GCT | CTA | TTG | ATT | GGT | 48 |
| | Met | Glu | Arg | Met | Ala | Leu | Tyr | Leu | Val | Ala | Ala | Leu | Leu | Ile | Gly | |
| | -22 | | -20 | | | | -15 | | | | | | -10 | | | |
| TTT | CCA | GGG | TCT | TCT | CAT | GGG | GCT | CTC | TAC | ACC | CTC | ATC | ACC | CCT | GCT | 96 |
| Phe | Pro | Gly | Ser | Ser | His | Gly | Ala | Leu | Tyr | Thr | Leu | Ile | Thr | Pro | Ala | |
| | | -5 | | | | | 1 | | | | 5 | | | | | |
| GTT | TTG | CGA | ACA | GAC | ACA | GAA | GAG | CAA | ATT | TTG | GTG | GAG | GCC | CAT | GGA | 144 |
| Val | Leu | Arg | Thr | Asp | Thr | Glu | Glu | Gln | Ile | Leu | Val | Glu | Ala | His | Gly | |
| 10 | | | | | 15 | | | | | 20 | | | | | 25 | |
| GAC | AGT | ACT | CCA | AAA | CAG | CTT | GAC | ATC | TTT | GTT | CAT | GAT | TTT | CCA | CGG | 192 |
| Asp | Ser | Thr | Pro | Lys | Gln | Leu | Asp | Ile | Phe | Val | His | Asp | Phe | Pro | Arg | |
| | | | | 30 | | | | | 35 | | | | | 40 | | |
| AAG | CAG | AAA | ACC | TTG | TTC | CAA | ACC | AGA | GTA | GAT | ATG | AAT | CCA | GCA | GGA | 240 |
| Lys | Gln | Lys | Thr | Leu | Phe | Gln | Thr | Arg | Val | Asp | Met | Asn | Pro | Ala | Gly | |
| | | | 45 | | | | | 50 | | | | | 55 | | | |
| GGC | ATG | CTT | GTC | ACT | CCA | ACT | ATA | GAG | ATT | CCA | GCA | AAA | GAA | GTG | AGT | 288 |
| Gly | Met | Leu | Val | Thr | Pro | Thr | Ile | Glu | Ile | Pro | Ala | Lys | Glu | Val | Ser | |
| | | 60 | | | | | 65 | | | | | 70 | | | | |
| ACG | GAC | TCC | AGG | CAA | AAT | CAA | TAT | GTG | GTT | GTG | CAA | GTA | ACT | GGT | CCT | 336 |
| Thr | Asp | Ser | Arg | Gln | Asn | Gln | Tyr | Val | Val | Val | Gln | Val | Thr | Gly | Pro | |
| | 75 | | | | | 80 | | | | | 85 | | | | | |
| CAA | GTG | AGA | TTG | GAA | AAG | GTG | GTT | CTC | CTT | TCT | TAC | CAG | AGT | AGC | TTT | 384 |
| Gln | Val | Arg | Leu | Glu | Lys | Val | Val | Leu | Leu | Ser | Tyr | Gln | Ser | Ser | Phe | |
| 90 | | | | | 95 | | | | | 100 | | | | | 105 | |
| CTG | TTT | ATC | CAG | ACA | GAT | AAA | GGC | ATC | TAT | ACA | CCA | GGG | TCT | CCA | GTA | 432 |
| Leu | Phe | Ile | Gln | Thr | Asp | Lys | Gly | Ile | Tyr | Thr | Pro | Gly | Ser | Pro | Val | |
| | | | | 110 | | | | | 115 | | | | | 120 | | |
| CTC | TAT | CGT | GTT | TTT | TCT | ATG | GAT | CAC | AAC | ACA | AGC | AAG | ATG | AAC | AAA | 480 |
| Leu | Tyr | Arg | Val | Phe | Ser | Met | Asp | His | Asn | Thr | Ser | Lys | Met | Asn | Lys | |
| | | | 125 | | | | | 130 | | | | | 135 | | | |
| ACT | GTG | ATT | GTT | GAG | TTT | CAG | ACT | CCA | GAA | GGC | ATT | CTT | GTC | AGT | TCT | 528 |
| Thr | Val | Ile | Val | Glu | Phe | Gln | Thr | Pro | Glu | Gly | Ile | Leu | Val | Ser | Ser | |
| | | 140 | | | | | 145 | | | | | 150 | | | | |
| AAT | TCA | GTT | GAC | CTA | AAC | TTC | TTC | TGG | CCT | TAC | AAT | TTA | CCA | GAC | CTT | 576 |
| Asn | Ser | Val | Asp | Leu | Asn | Phe | Phe | Trp | Pro | Tyr | Asn | Leu | Pro | Asp | Leu | |
| | 155 | | | | | 160 | | | | | 165 | | | | | |
| GTC | AGT | TTG | GGG | ACT | TGG | AGG | ATT | GTG | GCC | AAA | TAT | GAA | CAT | TCC | CCA | 624 |
| Val | Ser | Leu | Gly | Thr | Trp | Arg | Ile | Val | Ala | Lys | Tyr | Glu | His | Ser | Pro | |
| 170 | | | | | 175 | | | | | 180 | | | | | 185 | |
| GAG | AAT | TAT | ACT | GCA | TAT | TTT | GAT | GTC | AGG | AAA | TAT | GTG | TTG | CCA | AGC | 672 |
| Glu | Asn | Tyr | Thr | Ala | Tyr | Phe | Asp | Val | Arg | Lys | Tyr | Val | Leu | Pro | Ser | |
| | | | | 190 | | | | | 195 | | | | | 200 | | |
| TTT | GAA | GTC | CGT | CTG | CAA | CCA | TCA | GAG | AAG | TTT | TTT | TAC | ATT | GAC | GGC | 720 |
| Phe | Glu | Val | Arg | Leu | Gln | Pro | Ser | Glu | Lys | Phe | Phe | Tyr | Ile | Asp | Gly | |
| | | | 205 | | | | | 210 | | | | | 215 | | | |
| AAT | GAA | AAT | TTC | CAC | GTG | TCT | ATC | ACT | GCA | AGG | TAC | TTG | TAT | GGA | GAG | 768 |
| Asn | Glu | Asn | Phe | His | Val | Ser | Ile | Thr | Ala | Arg | Tyr | Leu | Tyr | Gly | Glu | |
| | | 220 | | | | | 225 | | | | | 230 | | | | |
| GAA | GTG | GAA | GGT | GTG | GCC | TTT | GTC | CTC | TTT | GGA | GTG | AAA | ATA | GAT | GAT | 816 |
| Glu | Val | Glu | Gly | Val | Ala | Phe | Val | Leu | Phe | Gly | Val | Lys | Ile | Asp | Asp | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 235 |     |     |     |     | 240 |     |     |     |     | 245 |     |     |      |
| GCT | AAA | AAG | AGT | ATT | CCA | GAC | TCA | CTC | ACG | AGA | ATT | CCG | ATT | ATT | GAT | 864  |
| Ala | Lys | Lys | Ser | Ile | Pro | Asp | Ser | Leu | Thr | Arg | Ile | Pro | Ile | Ile | Asp |      |
| 250 |     |     |     |     | 255 |     |     |     |     | 260 |     |     |     |     | 265 |      |
| GGA | GAT | GGG | AAA | GCA | ACA | CTA | AAA | AGA | GAT | ACA | TTC | CGT | TCT | CGA | TTT | 912  |
| Gly | Asp | Gly | Lys | Ala | Thr | Leu | Lys | Arg | Asp | Thr | Phe | Arg | Ser | Arg | Phe |      |
|     |     |     | 270 |     |     |     |     | 275 |     |     |     |     | 280 |     |     |      |
| CCA | AAT | CTC | AAT | GAG | CTT | GTT | GGG | CAT | ACT | CTG | TAT | GCA | TCT | GTA | ACA | 960  |
| Pro | Asn | Leu | Asn | Glu | Leu | Val | Gly | His | Thr | Leu | Tyr | Ala | Ser | Val | Thr |      |
|     |     |     | 285 |     |     |     |     | 290 |     |     |     |     | 295 |     |     |      |
| GTC | ATG | ACA | GAA | TCA | GGC | AGT | GAT | ATG | GTA | GTG | ACT | GAG | CAA | AGC | GGC | 1008 |
| Val | Met | Thr | Glu | Ser | Gly | Ser | Asp | Met | Val | Val | Thr | Glu | Gln | Ser | Gly |      |
|     |     | 300 |     |     |     |     | 305 |     |     |     |     | 310 |     |     |     |      |
| ATT | CAT | ATT | GTG | GCA | TCT | CCC | TAT | CAG | ATC | CAC | TTC | ACA | AAA | ACC | CCC | 1056 |
| Ile | His | Ile | Val | Ala | Ser | Pro | Tyr | Gln | Ile | His | Phe | Thr | Lys | Thr | Pro |      |
|     |     | 315 |     |     |     |     | 320 |     |     |     |     | 325 |     |     |     |      |
| AAA | TAT | TTC | AAG | CCA | GGA | ATG | CCA | TAT | GAA | CTG | ACG | GTG | TAT | GTT | ACC | 1104 |
| Lys | Tyr | Phe | Lys | Pro | Gly | Met | Pro | Tyr | Glu | Leu | Thr | Val | Tyr | Val | Thr |      |
| 330 |     |     |     |     | 335 |     |     |     |     | 340 |     |     |     |     | 345 |      |
| AAC | CCT | GAT | GGC | TCA | CCA | GCT | GCC | CAT | GTG | CCA | GTG | GTA | TCA | GAG | GCC | 1152 |
| Asn | Pro | Asp | Gly | Ser | Pro | Ala | Ala | His | Val | Pro | Val | Val | Ser | Glu | Ala |      |
|     |     |     | 350 |     |     |     |     | 355 |     |     |     |     | 360 |     |     |      |
| TTT | CAT | TCT | ATG | GGA | ACC | ACT | TTG | AGT | GAT | GGG | ACT | GCT | AAG | CTC | ATC | 1200 |
| Phe | His | Ser | Met | Gly | Thr | Thr | Leu | Ser | Asp | Gly | Thr | Ala | Lys | Leu | Ile |      |
|     |     |     | 365 |     |     |     |     | 370 |     |     |     |     | 375 |     |     |      |
| CTG | AAC | ATA | CCA | TTG | AAT | GCT | CAA | AGC | CTA | CCA | ATC | ACT | GTT | AGA | ACT | 1248 |
| Leu | Asn | Ile | Pro | Leu | Asn | Ala | Gln | Ser | Leu | Pro | Ile | Thr | Val | Arg | Thr |      |
|     |     * 380 |     |     |     |     | 385 |     |     |     |     | 390 |     |     |     |      |
| AAC | CAT | GGA | GAC | CTC | CCA | AGA | GAA | CGC | CAG | GCA | ACA | AAG | TCC | ATG | ACA | 1296 |
| Asn | His | Gly | Asp | Leu | Pro | Arg | Glu | Arg | Gln | Ala | Thr | Lys | Ser | Met | Thr |      |
|     | 395 |     |     |     |     | 400 |     |     |     |     | 405 |     |     |     |     |      |
| GCC | ATA | GCC | TAC | CAA | ACC | CAG | GGA | GGA | TCT | GGA | AAC | TAT | CTT | CAT | GTA | 1344 |
| Ala | Ile | Ala | Tyr | Gln | Thr | Gln | Gly | Gly | Ser | Gly | Asn | Tyr | Leu | His | Val |      |
| 410 |     |     |     |     | 415 |     |     |     |     | 420 |     |     |     |     | 425 |      |
| GCC | ATT | ACA | TCT | ACA | GAG | ATT | AAG | CCC | GGA | GAT | AAC | TTA | CCT | GTC | AAA | 1392 |
| Ala | Ile | Thr | Ser | Thr | Glu | Ile | Lys | Pro | Gly | Asp | Asn | Leu | Pro | Val | Lys |      |
|     |     |     |     | 430 |     |     |     |     | 435 |     |     |     |     | 440 |     |      |
| TTT | CAA | TGT | GAA | GGG | CAA | TGC | AAT | TCA | CTG | AAG | CAG | ATC | AAA | TAT | TTC | 1440 |
| Phe | Gln | Cys | Glu | Gly | Gln | Cys | Asn | Ser | Leu | Lys | Gln | Ile | Lys | Tyr | Phe |      |
|     |     |     | 445 |     |     |     |     | 450 |     |     |     |     | 455 |     |     |      |
| ACA | TAC | CTC | ATA | TTG | AAT | AAA | GGG | AAG | ATT | TTC | AAG | GTT | GGC | AGG | CAA | 1488 |
| Thr | Tyr | Leu | Ile | Leu | Asn | Lys | Gly | Lys | Ile | Phe | Lys | Val | Gly | Arg | Gln |      |
|     |     | 460 |     |     |     |     | 465 |     |     |     |     | 470 |     |     |     |      |
| CCC | AGG | AGA | GAT | GGG | CAG | AAT | CTG | GTG | ACC | ATG | AAT | CTG | CAT | ATC | ACT | 1536 |
| Pro | Arg | Arg | Asp | Gly | Gln | Asn | Leu | Val | Thr | Met | Asn | Leu | His | Ile | Thr |      |
|     | 475 |     |     |     |     | 480 |     |     |     |     | 485 |     |     |     |     |      |
| CCA | GAT | CTC | ATC | CCT | TCC | TTC | CGG | TTT | GTG | GCT | TAC | TAC | CAA | GTG | GGA | 1584 |
| Pro | Asp | Leu | Ile | Pro | Ser | Phe | Arg | Phe | Val | Ala | Tyr | Tyr | Gln | Val | Gly |      |
| 490 |     |     |     |     | 495 |     |     |     |     | 500 |     |     |     |     | 505 |      |
| AAC | AAC | GAA | ATT | GTG | GCT | GAT | TCT | GTC | TGG | GTG | GAT | GTG | AAG | GAT | ACC | 1632 |
| Asn | Asn | Glu | Ile | Val | Ala | Asp | Ser | Val | Trp | Val | Asp | Val | Lys | Asp | Thr |      |
|     |     |     |     | 510 |     |     |     |     | 515 |     |     |     |     | 520 |     |      |
| TGC | ATG | GGA | ACG | TTG | GTT | GTG | AAA | GGA | GAC | AAT | CTA | ATA | CAA | ATG | CCA | 1680 |
| Cys | Met | Gly | Thr | Leu | Val | Val | Lys | Gly | Asp | Asn | Leu | Ile | Gln | Met | Pro |      |
|     |     |     |     | 525 |     |     |     |     | 530 |     |     |     |     | 535 |     |      |
| GGA | GCT | GCA | ATG | AAA | ATC | AAA | TTG | GAA | GGG | GAT | CCA | GGT | GCT | CGG | GTT | 1728 |
| Gly | Ala | Ala | Met | Lys | Ile | Lys | Leu | Glu | Gly | Asp | Pro | Gly | Ala | Arg | Val |      |
|     |     |     | 540 |     |     |     |     | 545 |     |     |     |     | 550 |     |     |      |
| GGT | CTT | GTG | GCT | GTG | GAC | AAA | GCA | GTA | TAT | GTT | CTC | AAT | GAT | AAA | TAT | 1776 |
| Gly | Leu | Val | Ala | Val | Asp | Lys | Ala | Val | Tyr | Val | Leu | Asn | Asp | Lys | Tyr |      |

|  |  |  |  |  |  |  |  |  |  |  |  |  |  |  |  |
|---|---|---|---|---|---|---|---|---|---|---|---|---|---|---|---|
|  | 555 |  |  |  | 560 |  |  |  |  | 565 |  |  |  |  |  |
| AAG | ATT | AGC | CAA | GCT | AAG | ATA | TGG | GAC | ACA | ATA | GAA | AAG | AGT | GAC | TTT | 1824 |
| Lys | Ile | Ser | Gln | Ala | Lys | Ile | Trp | Asp | Thr | Ile | Glu | Lys | Ser | Asp | Phe |  |
| 570 |  |  |  |  | 575 |  |  |  |  | 580 |  |  |  |  | 585 |  |
| GGC | TGT | ACA | GCT | GGC | AGT | GGC | CAG | AAT | AAT | CTG | GGT | GTG | TTT | GAA | GAT | 1872 |
| Gly | Cys | Thr | Ala | Gly | Ser | Gly | Gln | Asn | Asn | Leu | Gly | Val | Phe | Glu | Asp |  |
|  |  |  |  |  | 590 |  |  |  |  | 595 |  |  |  |  | 600 |  |
| GCT | GGA | CTG | GCT | CTG | ACA | ACC | AGC | ACT | AAT | CTC | AAC | ACC | AAA | CAG | AGA | 1920 |
| Ala | Gly | Leu | Ala | Leu | Thr | Thr | Ser | Thr | Asn | Leu | Asn | Thr | Lys | Gln | Arg |  |
|  |  |  |  | 605 |  |  |  |  | 610 |  |  |  |  | 615 |  |  |
| TCA | GCT | GCA | AAG | TGT | CCT | CAG | CCT | GCA | AAT | CGG | AGG | CGT | CGC | AGT | TCT | 1968 |
| Ser | Ala | Ala | Lys | Cys | Pro | Gln | Pro | Ala | Asn | Arg | Arg | Arg | Arg | Ser | Ser |  |
|  |  | 620 |  |  |  | 625 |  |  |  |  | 630 |  |  |  |  |  |
| GTT | TTG | CTG | CTT | GAC | AGC | AAC | GCA | AGC | AAA | GCG | GCA | GAA | TTT | CAG | GAT | 2016 |
| Val | Leu | Leu | Leu | Asp | Ser | Asn | Ala | Ser | Lys | Ala | Ala | Glu | Phe | Gln | Asp |  |
| 635 |  |  |  |  | 640 |  |  |  |  | 645 |  |  |  |  |  |  |
| CAA | GAC | CTG | CGT | AAA | TGC | TGT | GAA | GAT | GTC | ATG | CAT | GAG | AAC | CCC | ATG | 2064 |
| Gln | Asp | Leu | Arg | Lys | Cys | Cys | Glu | Asp | Val | Met | His | Glu | Asn | Pro | Met |  |
| 650 |  |  |  |  | 655 |  |  |  |  | 660 |  |  |  |  | 665 |  |
| GGG | TAC | ACT | TGT | GAA | AAG | CGT | GCA | AAA | TAC | ATC | CAG | GAG | GGA | GAT | GCT | 2112 |
| Gly | Tyr | Thr | Cys | Glu | Lys | Arg | Ala | Lys | Tyr | Ile | Gln | Glu | Gly | Asp | Ala |  |
|  |  |  |  | 670 |  |  |  |  | 675 |  |  |  |  | 680 |  |  |
| TGT | AAG | GCT | GCC | TTC | CTT | GAA | TGC | TGT | CGC | TAC | ATC | AAG | GGG | GTC | CGA | 2160 |
| Cys | Lys | Ala | Ala | Phe | Leu | Glu | Cys | Cys | Arg | Tyr | Ile | Lys | Gly | Val | Arg |  |
|  |  |  | 685 |  |  |  |  | 690 |  |  |  |  | 695 |  |  |  |
| GAT | GAA | AAC | CAA | CGG | GAG | AGC | GAG | TTG | TTT | CTG | GCA | AGA | GAT | GAT | AAT | 2208 |
| Asp | Glu | Asn | Gln | Arg | Glu | Ser | Glu | Leu | Phe | Leu | Ala | Arg | Asp | Asp | Asn |  |
|  |  | 700 |  |  |  | 705 |  |  |  |  | 710 |  |  |  |  |  |
| GAA | GAT | GGT | TTC | ATA | GCA | GAT | AGT | GAT | ATC | ATC | TCA | AGG | TCT | GAT | TTC | 2256 |
| Glu | Asp | Gly | Phe | Ile | Ala | Asp | Ser | Asp | Ile | Ile | Ser | Arg | Ser | Asp | Phe |  |
|  | 715 |  |  |  |  | 720 |  |  |  |  | 725 |  |  |  |  |  |
| CCC | AAG | AGT | TGG | TTG | TGG | CTA | ACA | AAG | GAC | TTG | ACC | GAG | GAG | CCT | AAC | 2304 |
| Pro | Lys | Ser | Trp | Leu | Trp | Leu | Thr | Lys | Asp | Leu | Thr | Glu | Glu | Pro | Asn |  |
| 730 |  |  |  |  | 735 |  |  |  |  | 740 |  |  |  |  | 745 |  |
| AGT | CAA | GGG | ATT | TCA | AGC | AAG | ACA | ATG | TCT | TTT | TAT | CTG | AGG | GAT | TCC | 2352 |
| Ser | Gln | Gly | Ile | Ser | Ser | Lys | Thr | Met | Ser | Phe | Tyr | Leu | Arg | Asp | Ser |  |
|  |  |  |  | 750 |  |  |  |  | 755 |  |  |  |  | 760 |  |  |
| ATC | ACA | ACC | TGG | GTG | GTG | CTG | GCT | GTA | AGC | TTT | ACA | CCC | ACC | AAA | GGG | 2400 |
| Ile | Thr | Thr | Trp | Val | Val | Leu | Ala | Val | Ser | Phe | Thr | Pro | Thr | Lys | Gly |  |
|  |  |  | 765 |  |  |  |  | 770 |  |  |  |  | 775 |  |  |  |
| ATC | TGT | GTG | GCT | GAA | CCT | TAT | GAA | ATA | AGA | GTC | ATG | AAA | GTC | TTC | TTC | 2448 |
| Ile | Cys | Val | Ala | Glu | Pro | Tyr | Glu | Ile | Arg | Val | Met | Lys | Val | Phe | Phe |  |
|  |  | 780 |  |  |  | 785 |  |  |  |  | 790 |  |  |  |  |  |
| ATT | GAT | CTT | CAA | ATG | CCA | TAT | TCA | GTA | GTG | AAG | AAT | GAG | CAG | GTG | GAG | 2496 |
| Ile | Asp | Leu | Gln | Met | Pro | Tyr | Ser | Val | Val | Lys | Asn | Glu | Gln | Val | Glu |  |
| 795 |  |  |  |  | 800 |  |  |  |  | 805 |  |  |  |  |  |  |
| ATT | CGA | GCT | ATT | CTG | CAC | AAC | TAC | GTT | AAC | GAG | GAT | ATT | TAT | GTG | CGA | 2544 |
| Ile | Arg | Ala | Ile | Leu | His | Asn | Tyr | Val | Asn | Glu | Asp | Ile | Tyr | Val | Arg |  |
| 810 |  |  |  |  | 815 |  |  |  |  | 820 |  |  |  |  | 825 |  |
| GTG | GAA | CTG | TTA | TAC | AAC | CCA | GCC | TTC | TGC | AGT | GCT | TCC | ACA | AAA | GGA | 2592 |
| Val | Glu | Leu | Leu | Tyr | Asn | Pro | Ala | Phe | Cys | Ser | Ala | Ser | Thr | Lys | Gly |  |
|  |  |  |  | 830 |  |  |  |  | 835 |  |  |  |  | 840 |  |  |
| CAA | AGA | TAC | CGA | CAG | CAG | TTC | CCA | ATT | AAA | GCC | CTG | TCC | TCC | AGA | GCA | 2640 |
| Gln | Arg | Tyr | Arg | Gln | Gln | Phe | Pro | Ile | Lys | Ala | Leu | Ser | Ser | Arg | Ala |  |
|  |  |  | 845 |  |  |  |  | 850 |  |  |  |  | 855 |  |  |  |
| GTA | CCG | TTT | GTG | ATA | GTC | CCA | TTA | GAG | CAA | GGA | TTG | CAT | GAT | GTT | GAG | 2688 |
| Val | Pro | Phe | Val | Ile | Val | Pro | Leu | Glu | Gln | Gly | Leu | His | Asp | Val | Glu |  |
|  |  | 860 |  |  |  | 865 |  |  |  |  | 870 |  |  |  |  |  |
| ATT | AAA | GCA | AGT | GTC | CAG | GAA | GCG | TTG | TGG | TCA | GAC | GGT | GTG | AGG | AAG | 2736 |
| Ile | Lys | Ala | Ser | Val | Gln | Glu | Ala | Leu | Trp | Ser | Asp | Gly | Val | Arg | Lys |  |

|     |     |     |     |     |     |     |     |     |     |     |     |     |     |     |     |      |
|---|---|---|---|---|---|---|---|---|---|---|---|---|---|---|---|---|
|     |     | 875 |     |     |     |     | 880 |     |     |     |     |     | 885 |     |     |      |
| AAA | CTG | AAA | GTT | GTA | CCT | GAA | GGG | GTA | CAG | AAA | TCC | ATT | GTG | ACT | ATT | 2784 |
| Lys | Leu | Lys | Val | Val | Pro | Glu | Gly | Val | Gln | Lys | Ser | Ile | Val | Thr | Ile |      |
| 890 |     |     |     |     | 895 |     |     |     |     | 900 |     |     |     |     | 905 |      |
| GTT | AAA | CTG | GAC | CCA | AGG | GCA | AAA | GGA | GTT | GGT | GGA | ACA | CAG | CTA | GAA | 2832 |
| Val | Lys | Leu | Asp | Pro | Arg | Ala | Lys | Gly | Val | Gly | Gly | Thr | Gln | Leu | Glu |      |
|     |     |     |     | 910 |     |     |     |     | 915 |     |     |     |     | 920 |     |      |
| GTG | ATC | AAA | GCC | CGC | AAA | TTA | GAT | GAC | AGA | GTG | CCT | GAC | ACA | GAA | ATT | 2880 |
| Val | Ile | Lys | Ala | Arg | Lys | Leu | Asp | Asp | Arg | Val | Pro | Asp | Thr | Glu | Ile |      |
|     |     |     | 925 |     |     |     |     | 930 |     |     |     |     | 935 |     |     |      |
| GAA | ACC | AAG | ATT | ATC | ATC | CAA | GGT | GAC | CCT | GTG | GCT | CAG | ATT | ATT | GAA | 2928 |
| Glu | Thr | Lys | Ile | Ile | Ile | Gln | Gly | Asp | Pro | Val | Ala | Gln | Ile | Ile | Glu |      |
|     |     | 940 |     |     |     |     | 945 |     |     |     |     | 950 |     |     |     |      |
| AAC | TCA | ATT | GAT | GGA | AGT | AAA | CTC | AAC | CAT | CTC | ATT | ATC | ACT | CCT | TCT | 2976 |
| Asn | Ser | Ile | Asp | Gly | Ser | Lys | Leu | Asn | His | Leu | Ile | Ile | Thr | Pro | Ser |      |
|     | 955 |     |     |     |     | 960 |     |     |     |     | 965 |     |     |     |     |      |
| GGC | TGT | GGG | GAG | CAA | AAT | ATG | ATC | CGC | ATG | GCC | GCA | CCA | GTT | ATT | GCC | 3024 |
| Gly | Cys | Gly | Glu | Gln | Asn | Met | Ile | Arg | Met | Ala | Ala | Pro | Val | Ile | Ala |      |
| 970 |     |     |     |     | 975 |     |     |     |     | 980 |     |     |     |     | 985 |      |
| ACC | TAC | TAC | CTG | GAC | ACC | ACA | GAG | CAG | TGG | GAG | ACT | CTC | GGC | ATA | AAT | 3072 |
| Thr | Tyr | Tyr | Leu | Asp | Thr | Thr | Glu | Gln | Trp | Glu | Thr | Leu | Gly | Ile | Asn |      |
|     |     |     |     | 990 |     |     |     |     | 995 |     |     |     |     | 1000|     |      |
| CGC | AGG | ACT | GAA | GCT | GTC | AAT | CAG | ATC | GTG | ACT | GGT | TAT | GCC | CAG | CAG | 3120 |
| Arg | Arg | Thr | Glu | Ala | Val | Asn | Gln | Ile | Val | Thr | Gly | Tyr | Ala | Gln | Gln |      |
|     |     |     |     | 1005|     |     |     |     | 1010|     |     |     |     | 1015|     |      |
| ATG | GTG | TAC | AAG | AAA | GCA | GAT | CAT | TCC | TAT | GCA | GCA | TTT | ACA | AAC | CGT | 3168 |
| Met | Val | Tyr | Lys | Lys | Ala | Asp | His | Ser | Tyr | Ala | Ala | Phe | Thr | Asn | Arg |      |
|     |     | 1020|     |     |     |     | 1025|     |     |     |     | 1030|     |     |     |      |
| GCA | TCT | AGT | TCT | TGG | CTA | ACA | GCA | TAT | GTC | GTA | AAA | GTC | TTT | GCC | ATG | 3216 |
| Ala | Ser | Ser | Ser | Trp | Leu | Thr | Ala | Tyr | Val | Val | Lys | Val | Phe | Ala | Met |      |
|     | 1035|     |     |     |     | 1040|     |     |     |     | 1045|     |     |     |     |      |
| GCT | GCC | AAA | ATG | GTA | GCA | GGC | ATT | AGT | CAT | GAA | ATC | ATT | TGT | GGA | GGT | 3264 |
| Ala | Ala | Lys | Met | Val | Ala | Gly | Ile | Ser | His | Glu | Ile | Ile | Cys | Gly | Gly |      |
| 1050|     |     |     |     | 1055|     |     |     |     | 1060|     |     |     |     | 1065|      |
| GTG | AGG | TGG | CTG | ATT | CTG | AAC | AGG | CAA | CAA | CCA | GAT | GGA | GCG | TTC | AAA | 3312 |
| Val | Arg | Trp | Leu | Ile | Leu | Asn | Arg | Gln | Gln | Pro | Asp | Gly | Ala | Phe | Lys |      |
|     |     |     |     | 1070|     |     |     |     | 1075|     |     |     |     | 1080|     |      |
| GAA | AAT | GCC | CCT | GTA | CTT | TCT | GGA | ACA | ATG | CAG | GGA | GGA | ATT | CAA | GGT | 3360 |
| Glu | Asn | Ala | Pro | Val | Leu | Ser | Gly | Thr | Met | Gln | Gly | Gly | Ile | Gln | Gly |      |
|     |     |     | 1085|     |     |     |     | 1090|     |     |     |     | 1095|     |     |      |
| GCT | GAA | GAA | GAA | GTA | TAT | TTA | ACA | GCT | TTC | ATT | CTG | GTT | GCG | TTG | TTG | 3408 |
| Ala | Glu | Glu | Glu | Val | Tyr | Leu | Thr | Ala | Phe | Ile | Leu | Val | Ala | Leu | Leu |      |
|     |     |     | 1100|     |     |     |     | 1105|     |     |     |     | 1110|     |     |      |
| GAA | TCC | AAA | ACA | ATC | TGC | AAT | GAC | TAT | GTC | AAT | AGT | CTA | GAC | AGC | AGC | 3456 |
| Glu | Ser | Lys | Thr | Ile | Cys | Asn | Asp | Tyr | Val | Asn | Ser | Leu | Asp | Ser | Ser |      |
|     | 1115|     |     |     |     | 1120|     |     |     |     | 1125|     |     |     |     |      |
| ATC | AAG | AAG | GCC | ACA | AAT | TAT | TTA | CTC | AAA | AAG | TAT | GAG | AAA | CTG | CAA | 3504 |
| Ile | Lys | Lys | Ala | Thr | Asn | Tyr | Leu | Leu | Lys | Lys | Tyr | Glu | Lys | Leu | Gln |      |
| 1130|     |     |     |     | 1135|     |     |     |     | 1140|     |     |     |     | 1145|      |
| AGG | CCT | TAC | ACT | ACA | GCC | CTC | ACA | GCC | TAT | GCT | TTG | GCT | GCT | GCA | GAC | 3552 |
| Arg | Pro | Tyr | Thr | Thr | Ala | Leu | Thr | Ala | Tyr | Ala | Leu | Ala | Ala | Ala | Asp |      |
|     |     |     |     | 1150|     |     |     |     | 1155|     |     |     |     | 1160|     |      |
| CAA | CTC | AAT | GAT | GAC | AGG | GTA | CTC | ATG | GCA | GCA | TCA | ACA | GGA | AGG | GAT | 3600 |
| Gln | Leu | Asn | Asp | Asp | Arg | Val | Leu | Met | Ala | Ala | Ser | Thr | Gly | Arg | Asp |      |
|     |     |     | 1165|     |     |     |     | 1170|     |     |     |     | 1175|     |     |      |
| CAT | TGG | GAA | GAA | TAC | AAT | GCT | CAC | ACC | CAC | AAC | ATT | GAA | GGC | ACT | TCC | 3648 |
| His | Trp | Glu | Glu | Tyr | Asn | Ala | His | Thr | His | Asn | Ile | Glu | Gly | Thr | Ser |      |
|     |     |     | 1180|     |     |     |     | 1185|     |     |     |     | 1190|     |     |      |
| TAT | GCC | TTG | TTG | GCC | CTG | CTG | AAA | ATG | AAG | AAA | TTT | GAT | CAA | ACT | GGT | 3696 |
| Tyr | Ala | Leu | Leu | Ala | Leu | Leu | Lys | Met | Lys | Lys | Phe | Asp | Gln | Thr | Gly |      |

|  |  |  |  |  |  |  |  |  |  |  |  |  |  |  |  |
|---|---|---|---|---|---|---|---|---|---|---|---|---|---|---|---|
| | | | | 1195 | | | | | 1200 | | | | | 1205 | |

```
CCC ATA GTC AGA TGG CTG ACA GAT CAG AAT TTT TAT GGG GAA ACA TAT      3744
Pro Ile Val Arg Trp Leu Thr Asp Gln Asn Phe Tyr Gly Glu Thr Tyr
1210                1215                1220                1225

GGA CAA ACC CAA GCA ACA GTT ATG GCA TTT CAA GCT CTT GCT GAA TAT      3792
Gly Gln Thr Gln Ala Thr Val Met Ala Phe Gln Ala Leu Ala Glu Tyr
                1230                1235                1240

GAG ATT CAG ATG CCT ACC CAT AAG GAC TTA AAC TTA GAT ATT ACT ATT      3840
Glu Ile Gln Met Pro Thr His Lys Asp Leu Asn Leu Asp Ile Thr Ile
                    1245                1250                1255

GAA CTG CCA GAT CGA GAA GTA CCT ATA AGG TAC AGA ATT AAT TAT GAA      3888
Glu Leu Pro Asp Arg Glu Val Pro Ile Arg Tyr Arg Ile Asn Tyr Glu
1260                1265                1270

AAT GCT CTC CTG GCT CGG ACA GTA GAG ACC AAA CTC AAC CAA GAC ATC      3936
Asn Ala Leu Leu Ala Arg Thr Val Glu Thr Lys Leu Asn Gln Asp Ile
    1275                1280                1285

ACT GTG ACA GCA TCA GGT GAT GGA AAA GCA ACA ATG ACC ATT TTG ACA      3984
Thr Val Thr Ala Ser Gly Asp Gly Lys Ala Thr Met Thr Ile Leu Thr
1290                1295                1300                1305

TTC TAT AAC GCA CAG TTG CAG GAG AAG GCA AAT GTT TGC AAT AAA TTT      4032
Phe Tyr Asn Ala Gln Leu Gln Glu Lys Ala Asn Val Cys Asn Lys Phe
                1310                1315                1320

CAT CTT AAT GTT TCT GTT GAA AAC ATC CAC TTG AAT GCA ATG GGA GCC      4080
His Leu Asn Val Ser Val Glu Asn Ile His Leu Asn Ala Met Gly Ala
                    1325                1330                1335

AAG GGA GCC CTC ATG CTC AAG ATC TGC ACA AGG TAT CTG GGA GAA GTT      4128
Lys Gly Ala Leu Met Leu Lys Ile Cys Thr Arg Tyr Leu Gly Glu Val
                1340                1345                1350

GAT TCT ACA ATG ACA ATA ATT GAT ATT TCT ATG CTG ACT GGT TTT CTC      4176
Asp Ser Thr Met Thr Ile Ile Asp Ile Ser Met Leu Thr Gly Phe Leu
1355                1360                1365

CCT GAT GCT GAA GAC CTT ACA AGG CTT TCT AAA GGA GTG GAC AGA TAC      4224
Pro Asp Ala Glu Asp Leu Thr Arg Leu Ser Lys Gly Val Asp Arg Tyr
1370                1375                1380                1385

ATC TCC AGA TAT GAA GTT GAC AAT AAT ATG GCT CAG AAA GTA GCT GTT      4272
Ile Ser Arg Tyr Glu Val Asp Asn Asn Met Ala Gln Lys Val Ala Val
                    1390                1395                1400

ATC ATT TAC TTA AAC AAG GTC TCC CAC TCT GAA GAT GAA TGC CTG CAC      4320
Ile Ile Tyr Leu Asn Lys Val Ser His Ser Glu Asp Glu Cys Leu His
                1405                1410                1415

TTT AAG ATT CTC AAG CAT TTT GAA GTT GGC TTC ATT CAG CCA GGA TCA      4368
Phe Lys Ile Leu Lys His Phe Glu Val Gly Phe Ile Gln Pro Gly Ser
                1420                1425                1430

GTC AAG GTG TAC AGC TAC TAC AAT CTA GAT GAA AAA TGT ACC AAG TTC      4416
Val Lys Val Tyr Ser Tyr Tyr Asn Leu Asp Glu Lys Cys Thr Lys Phe
1435                1440                1445

TAC CAT CCA GAT AAA GGA ACA GGC CTT CTC AAT AAG ATA TGT ATT GGT      4464
Tyr His Pro Asp Lys Gly Thr Gly Leu Leu Asn Lys Ile Cys Ile Gly
1450                1455                1460                1465

AAC GTT TGC CGA TGT GCA GGA GAA ACC TGT TCC TCG CTC AAC CAT CAG      4512
Asn Val Cys Arg Cys Ala Gly Glu Thr Cys Ser Ser Leu Asn His Gln
                    1470                1475                1480

GAA AGG ATT GAT GTT CCA TTA CAA ATT GAA AAA GCC TGC GAG ACG AAT      4560
Glu Arg Ile Asp Val Pro Leu Gln Ile Glu Lys Ala Cys Glu Thr Asn
                1485                1490                1495

GTG GAT TAT GTC TAC AAA ACC AAG CTG CTT CGA ATA GAA GAA CAA GAT      4608
Val Asp Tyr Val Tyr Lys Thr Lys Leu Leu Arg Ile Glu Glu Gln Asp
                1500                1505                1510

GGT AAT GAT ATC TAT GTC ATG GAT GTT TTA GAA GTT ATT AAA CAA GGT      4656
Gly Asn Asp Ile Tyr Val Met Asp Val Leu Glu Val Ile Lys Gln Gly
```

|   |   |   |   |   |   | 1515 |   |   |   |   |   | 1520 |   |   |   |   | 1525 |   |   |      |
|---|---|---|---|---|---|------|---|---|---|---|---|------|---|---|---|---|------|---|---|------|
| ACT | GAC | AAA | AAT | CCA | CGA | GCA | AAG | ACC | CAC | CAG | TAC | ATA | AGT | CAA | AGG | | | | | 4704 |
| Thr | Asp | Lys | Asn | Pro | Arg | Ala | Lys | Thr | His | Gln | Tyr | Ile | Ser | Gln | Arg | | | | | |
| 1530 | | | | 1535 | | | | | 1540 | | | | | | 1545 | | | | | |

| AAA | TGC | CAG | GAG | GCT | CTG | AAT | CTG | AAG | GTG | AAT | GAT | GAT | TAT | CTG | ATC | 4752 |
| Lys | Cys | Gln | Glu | Ala | Leu | Asn | Leu | Lys | Val | Asn | Asp | Asp | Tyr | Leu | Ile | |
| | | | 1550 | | | | 1555 | | | | | | 1560 | | | |

| TGG | GGT | TCC | AGG | AGT | GAC | CTG | TTG | CCC | ACG | AAA | GAT | AAA | ATT | TCC | TAC | 4800 |
| Trp | Gly | Ser | Arg | Ser | Asp | Leu | Leu | Pro | Thr | Lys | Asp | Lys | Ile | Ser | Tyr | |
| | | | 1565 | | | | | 1570 | | | | | 1575 | | | |

| ATC | ATT | ACA | AAG | AAC | ACA | TGG | ATT | GAG | AGA | TGG | CCA | CAT | GAA | GAC | GAA | 4848 |
| Ile | Ile | Thr | Lys | Asn | Thr | Trp | Ile | Glu | Arg | Trp | Pro | His | Glu | Asp | Glu | |
| | | | 1580 | | | | | 1585 | | | | | 1590 | | | |

| TGT | CAG | GAA | GAA | GAA | TTC | CAA | AAG | TTG | TGT | GAT | GAC | TTT | GCT | CAG | TTT | 4896 |
| Cys | Gln | Glu | Glu | Glu | Phe | Gln | Lys | Leu | Cys | Asp | Asp | Phe | Ala | Gln | Phe | |
| | | 1595 | | | | | 1600 | | | | | 1605 | | | | |

| AGC | TAC | ACA | TTG | ACT | GAG | TTT | GGC | TGC | CCT | ACT | TAAAAGTTCA | GAAGAATCAA | 4949 |
| Ser | Tyr | Thr | Leu | Thr | Glu | Phe | Gly | Cys | Pro | Thr | | | |
| 1610 | | | | | 1615 | | | | | 1620 | | | |

| TGATAGGAAG | GAAATTCTCA | GAAGACAGAT | TTTTGAGCCA | ATGCATATAT | GTTACTTTGC | 5009 |
| CTCTTGATCT | TTTAGTTTTA | TGTCAATTTG | CTCTGTTATT | TTCCCTTAAA | TTGTTTATAC | 5069 |
| ATAAAATAAA | TAATCGATTT | CTTACTTTGA | TATGTTCTTG | ATTTTTAATA | AACAATGGTG | 5129 |
| ATTCATGATT | ATTTTTTTCT | TCTTCTGATC | CATCCAATAT | TTGAAGTGCT | CTGAACAGAG | 5189 |
| CACTTATGGA | GTAATGTTTT | AGTGATGGAT | GAATAAGTTG | GTGAGTCAAT | ATTATCAGGC | 5249 |
| CCTATATACT | CTTATGGAAG | ATCGATTTGT | ACCCAAAGAA | ACATAGATTG | AAATGTGTTA | 5309 |
| CTTTGAAAAC | AGAGGTTTCA | GTTGTATATG | TTTACACTTG | GATACAATCT | TAACTCTTAA | 5369 |
| TAAACACTGA | TCTCAGAACA | TTTAACAGCT | GCTATTTAAT | AATGACAAAA | TATTCTTTGA | 5429 |
| CTGCACCCAC | AGAAAACATT | GCATTACATT | AGAATGGGTT | TTATCAGATG | ACTAAGTCTG | 5489 |
| CTAGACTTGC | CATCTGTCAA | AATGTGCCTC | TTCCCCAGCT | CCAACTTTAA | GGATAGTAAC | 5549 |
| TAATAGATGT | TCTCTCATTG | GCTCCTGACA | GAGGTGTGGT | AGCCACTGAG | TTTCCCTGGA | 5609 |
| TGACACTAGA | AGCTGGCAGC | ACACTGCAGC | CTGGTGGAGG | GGCCTCTTTT | GCTATCCCAT | 5669 |
| GAGCTTCTAT | TCATCCTCTT | ATCTGTTGGG | ATGGGGATGG | GACGTCTCTG | ATTTTCCAGG | 5729 |
| TATACAGGTG | ATCTCATTTA | CTAACATCAC | CACTAACTTC | AAGGATTGGT | TGAGGGGTTA | 5789 |
| TGCCAATGTG | ATTGAAGGTT | TCACCCATGT | GAATCTATTC | TCCAATCCCA | ATGCTGTATC | 5849 |
| TATGCTGCTC | ATTTCTGCTT | GTAAAAATGG | TATAAAAAGA | ATAAACACTG | CCCAGGCAGT | 5909 |
| CAGACATCGG | AATTC | | | | | 5924 |

( 2 ) INFORMATION FOR SEQ ID NO:45:

( i ) SEQUENCE CHARACTERISTICS:
        ( A ) LENGTH: 1642 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

| Met | Glu | Arg | Met | Ala | Leu | Tyr | Leu | Val | Ala | Ala | Leu | Leu | Ile | Gly | Phe |
| -22 | | -20 | | | | -15 | | | | | -10 | | | | |

| Pro | Gly | Ser | Ser | His | Gly | Ala | Leu | Tyr | Thr | Leu | Ile | Thr | Pro | Ala | Val |
| | -5 | | | | 1 | | | | 5 | | | | | | 10 |

| Leu | Arg | Thr | Asp | Thr | Glu | Glu | Gln | Ile | Leu | Val | Glu | Ala | His | Gly | Asp |
| | | | | 15 | | | | | 20 | | | | | 25 | |

| | | | | | | | | | | | | | | | |
|---|---|---|---|---|---|---|---|---|---|---|---|---|---|---|---|
|Ser|Thr|Pro|Lys|Gln|Leu|Asp|Ile|Phe|Val|His|Asp|Phe|Pro|Arg|Lys|
| | | |30| | | |35| | | | |40| | | |
|Gln|Lys|Thr|Leu|Phe|Gln|Thr|Arg|Val|Asp|Met|Asn|Pro|Ala|Gly|Gly|
| | |45| | | |50| | | | |55| | | | |
|Met|Leu|Val|Thr|Pro|Thr|Ile|Glu|Ile|Pro|Ala|Lys|Glu|Val|Ser|Thr|
| |60| | | |65| | | | |70| | | | | |
|Asp|Ser|Arg|Gln|Asn|Gln|Tyr|Val|Val|Val|Gln|Val|Thr|Gly|Pro|Gln|
|75| | | |80| | | | |85| | | | | |90|
|Val|Arg|Leu|Glu|Lys|Val|Val|Leu|Leu|Ser|Tyr|Gln|Ser|Ser|Phe|Leu|
| | | |95| | | |100| | | | |105| | | |
|Phe|Ile|Gln|Thr|Asp|Lys|Gly|Ile|Tyr|Thr|Pro|Gly|Ser|Pro|Val|Leu|
| | |110| | | |115| | | | |120| | | | |
|Tyr|Arg|Val|Phe|Ser|Met|Asp|His|Asn|Thr|Ser|Lys|Met|Asn|Lys|Thr|
| |125| | | |130| | | | |135| | | | | |
|Val|Ile|Val|Glu|Phe|Gln|Thr|Pro|Glu|Gly|Ile|Leu|Val|Ser|Ser|Asn|
|140| | | |145| | | | |150| | | | | | |
|Ser|Val|Asp|Leu|Asn|Phe|Phe|Trp|Pro|Tyr|Asn|Leu|Pro|Asp|Leu|Val|
|155| | | |160| | | |165| | | | |170|
|Ser|Leu|Gly|Thr|Trp|Arg|Ile|Val|Ala|Lys|Tyr|Glu|His|Ser|Pro|Glu|
| | | |175| | | |180| | | | |185| | | |
|Asn|Tyr|Thr|Ala|Tyr|Phe|Asp|Val|Arg|Lys|Tyr|Val|Leu|Pro|Ser|Phe|
| | |190| | | |195| | | | |200| | | | |
|Glu|Val|Arg|Leu|Gln|Pro|Ser|Glu|Lys|Phe|Phe|Tyr|Ile|Asp|Gly|Asn|
| |205| | | |210| | | | |215| | | | | |
|Glu|Asn|Phe|His|Val|Ser|Ile|Thr|Ala|Arg|Tyr|Leu|Tyr|Gly|Glu|Glu|
|220| | | |225| | | | |230| | | | | | |
|Val|Glu|Gly|Val|Ala|Phe|Val|Leu|Phe|Gly|Val|Lys|Ile|Asp|Asp|Ala|
|235| | | |240| | | | |245| | | | |250|
|Lys|Lys|Ser|Ile|Pro|Asp|Ser|Leu|Thr|Arg|Ile|Pro|Ile|Ile|Asp|Gly|
| | | |255| | | |260| | | | |265| | | |
|Asp|Gly|Lys|Ala|Thr|Leu|Lys|Arg|Asp|Thr|Phe|Arg|Ser|Arg|Phe|Pro|
| | |270| | | |275| | | | |280| | | | |
|Asn|Leu|Asn|Glu|Leu|Val|Gly|His|Thr|Leu|Tyr|Ala|Ser|Val|Thr|Val|
| |285| | | |290| | | | |295| | | | | |
|Met|Thr|Glu|Ser|Gly|Ser|Asp|Met|Val|Val|Thr|Glu|Gln|Ser|Gly|Ile|
|300| | | |305| | | | |310| | | | | | |
|His|Ile|Val|Ala|Ser|Pro|Tyr|Gln|Ile|His|Phe|Thr|Lys|Thr|Pro|Lys|
|315| | | |320| | | | |325| | | | |330|
|Tyr|Phe|Lys|Pro|Gly|Met|Pro|Tyr|Glu|Leu|Thr|Val|Tyr|Val|Thr|Asn|
| | | |335| | | |340| | | | |345| | | |
|Pro|Asp|Gly|Ser|Pro|Ala|Ala|His|Val|Pro|Val|Val|Ser|Glu|Ala|Phe|
| | |350| | | |355| | | | |360| | | | |
|His|Ser|Met|Gly|Thr|Thr|Leu|Ser|Asp|Gly|Thr|Ala|Lys|Leu|Ile|Leu|
| |365| | | |370| | | | |375| | | | | |
|Asn|Ile|Pro|Leu|Asn|Ala|Gln|Ser|Leu|Pro|Ile|Thr|Val|Arg|Thr|Asn|
|380| | | |385| | | | |390| | | | | | |
|His|Gly|Asp|Leu|Pro|Arg|Glu|Arg|Gln|Ala|Thr|Lys|Ser|Met|Thr|Ala|
|395| | | |400| | | | |405| | | | |410|
|Ile|Ala|Tyr|Gln|Thr|Gln|Gly|Gly|Ser|Gly|Asn|Tyr|Leu|His|Val|Ala|
| | | |415| | | |420| | | | |425| | | |
|Ile|Thr|Ser|Thr|Glu|Ile|Lys|Pro|Gly|Asp|Asn|Leu|Pro|Val|Lys|Phe|
| | |430| | | |435| | | | |440| | | | |
|Gln|Cys|Glu|Gly|Gln|Cys|Asn|Ser|Leu|Lys|Gln|Ile|Lys|Tyr|Phe|Thr|

|   |   |   | 445 |   |   |   | 450 |   |   |   | 455 |   |   |
|---|---|---|---|---|---|---|---|---|---|---|---|---|---|

Tyr Leu Ile Leu Asn Lys Gly Lys Ile Phe Lys Val Gly Arg Gln Pro
460                 465                 470

Arg Arg Asp Gly Gln Asn Leu Val Thr Met Asn Leu His Ile Thr Pro
475                 480                 485                 490

Asp Leu Ile Pro Ser Phe Arg Phe Val Ala Tyr Tyr Gln Val Gly Asn
                495                 500                 505

Asn Glu Ile Val Ala Asp Ser Val Trp Val Asp Val Lys Asp Thr Cys
            510                 515                 520

Met Gly Thr Leu Val Val Lys Gly Asp Asn Leu Ile Gln Met Pro Gly
        525                 530                 535

Ala Ala Met Lys Ile Lys Leu Glu Gly Asp Pro Gly Ala Arg Val Gly
    540                 545                 550

Leu Val Ala Val Asp Lys Ala Val Tyr Val Leu Asn Asp Lys Tyr Lys
555                 560                 565                 570

Ile Ser Gln Ala Lys Ile Trp Asp Thr Ile Glu Lys Ser Asp Phe Gly
                575                 580                 585

Cys Thr Ala Gly Ser Gly Gln Asn Asn Leu Gly Val Phe Glu Asp Ala
            590                 595                 600

Gly Leu Ala Leu Thr Thr Ser Thr Asn Leu Asn Thr Lys Gln Arg Ser
        605                 610                 615

Ala Ala Lys Cys Pro Gln Pro Ala Asn Arg Arg Arg Ser Ser Val
    620                 625                 630

Leu Leu Leu Asp Ser Asn Ala Ser Lys Ala Ala Glu Phe Gln Asp Gln
635                 640                 645                 650

Asp Leu Arg Lys Cys Cys Glu Asp Val Met His Glu Asn Pro Met Gly
                655                 660                 665

Tyr Thr Cys Glu Lys Arg Ala Lys Tyr Ile Gln Glu Gly Asp Ala Cys
            670                 675                 680

Lys Ala Ala Phe Leu Glu Cys Cys Arg Tyr Ile Lys Gly Val Arg Asp
        685                 690                 695

Glu Asn Gln Arg Glu Ser Glu Leu Phe Leu Ala Arg Asp Asp Asn Glu
    700                 705                 710

Asp Gly Phe Ile Ala Asp Ser Asp Ile Ile Ser Arg Ser Asp Phe Pro
715                 720                 725                 730

Lys Ser Trp Leu Trp Leu Thr Lys Asp Leu Thr Glu Glu Pro Asn Ser
                735                 740                 745

Gln Gly Ile Ser Ser Lys Thr Met Ser Phe Tyr Leu Arg Asp Ser Ile
            750                 755                 760

Thr Thr Trp Val Val Leu Ala Val Ser Phe Thr Pro Thr Lys Gly Ile
        765                 770                 775

Cys Val Ala Glu Pro Tyr Glu Ile Arg Val Met Lys Val Phe Phe Ile
    780                 785                 790

Asp Leu Gln Met Pro Tyr Ser Val Val Lys Asn Glu Gln Val Glu Ile
795                 800                 805                 810

Arg Ala Ile Leu His Asn Tyr Val Asn Glu Asp Ile Tyr Val Arg Val
                815                 820                 825

Glu Leu Leu Tyr Asn Pro Ala Phe Cys Ser Ala Ser Thr Lys Gly Gln
            830                 835                 840

Arg Tyr Arg Gln Gln Phe Pro Ile Lys Ala Leu Ser Ser Arg Ala Val
        845                 850                 855

Pro Phe Val Ile Val Pro Leu Glu Gln Gly Leu His Asp Val Glu Ile
    860                 865                 870

```
Lys  Ala  Ser  Val  Gln  Glu  Ala  Leu  Trp  Ser  Asp  Gly  Val  Arg  Lys  Lys
875            880                 885                 890

Leu  Lys  Val  Val  Pro  Glu  Gly  Val  Gln  Ser  Ile  Val  Thr  Ile  Val
               895                 900                      905

Lys  Leu  Asp  Pro  Arg  Ala  Lys  Gly  Val  Gly  Gly  Thr  Gln  Leu  Glu  Val
               910                 915                      920

Ile  Lys  Ala  Arg  Lys  Leu  Asp  Asp  Arg  Val  Pro  Asp  Thr  Glu  Ile  Glu
          925                      930                 935

Thr  Lys  Ile  Ile  Ile  Gln  Gly  Asp  Pro  Val  Ala  Gln  Ile  Ile  Glu  Asn
          940                      945                 950

Ser  Ile  Asp  Gly  Ser  Lys  Leu  Asn  His  Leu  Ile  Ile  Thr  Pro  Ser  Gly
955                      960                      965                      970

Cys  Gly  Glu  Gln  Asn  Met  Ile  Arg  Met  Ala  Ala  Pro  Val  Ile  Ala  Thr
                    975                 980                 985

Tyr  Tyr  Leu  Asp  Thr  Thr  Glu  Gln  Trp  Glu  Thr  Leu  Gly  Ile  Asn  Arg
               990                      995                 1000

Arg  Thr  Glu  Ala  Val  Asn  Gln  Ile  Val  Thr  Gly  Tyr  Ala  Gln  Gln  Met
          1005                      1010                 1015

Val  Tyr  Lys  Lys  Ala  Asp  His  Ser  Tyr  Ala  Ala  Phe  Thr  Asn  Arg  Ala
     1020                 1025                      1030

Ser  Ser  Ser  Trp  Leu  Thr  Ala  Tyr  Val  Val  Lys  Val  Phe  Ala  Met  Ala
1035                      1040                      1045                      1050

Ala  Lys  Met  Val  Ala  Gly  Ile  Ser  His  Glu  Ile  Ile  Cys  Gly  Gly  Val
               1055                      1060                      1065

Arg  Trp  Leu  Ile  Leu  Asn  Arg  Gln  Gln  Pro  Asp  Gly  Ala  Phe  Lys  Glu
               1070                      1075                      1080

Asn  Ala  Pro  Val  Leu  Ser  Gly  Thr  Met  Gln  Gly  Gly  Ile  Gln  Gly  Ala
               1085                      1090                      1095

Glu  Glu  Glu  Val  Tyr  Leu  Thr  Ala  Phe  Ile  Leu  Val  Ala  Leu  Leu  Glu
               1100                 1105                      1110

Ser  Lys  Thr  Ile  Cys  Asn  Asp  Tyr  Val  Asn  Ser  Leu  Asp  Ser  Ser  Ile
1115                      1120                      1125                      1130

Lys  Lys  Ala  Thr  Asn  Tyr  Leu  Leu  Lys  Lys  Tyr  Glu  Lys  Leu  Gln  Arg
               1135                      1140                      1145

Pro  Tyr  Thr  Thr  Ala  Leu  Thr  Ala  Tyr  Ala  Leu  Ala  Ala  Ala  Asp  Gln
               1150                      1155                      1160

Leu  Asn  Asp  Asp  Arg  Val  Leu  Met  Ala  Ala  Ser  Thr  Gly  Arg  Asp  His
               1165                      1170                      1175

Trp  Glu  Glu  Tyr  Asn  Ala  His  Thr  His  Asn  Ile  Glu  Gly  Thr  Ser  Tyr
     1180                      1185                      1190

Ala  Leu  Leu  Ala  Leu  Leu  Lys  Met  Lys  Lys  Phe  Asp  Gln  Thr  Gly  Pro
1195                      1200                      1205                      1210

Ile  Val  Arg  Trp  Leu  Thr  Asp  Gln  Asn  Phe  Tyr  Gly  Glu  Thr  Tyr  Gly
               1215                      1220                      1225

Gln  Thr  Gln  Ala  Thr  Val  Met  Ala  Phe  Gln  Ala  Leu  Ala  Glu  Tyr  Glu
               1230                      1235                      1240

Ile  Gln  Met  Pro  Thr  His  Lys  Asp  Leu  Asn  Leu  Asp  Ile  Thr  Ile  Glu
          1245                      1250                      1255

Leu  Pro  Asp  Arg  Glu  Val  Pro  Ile  Arg  Tyr  Arg  Ile  Asn  Tyr  Glu  Asn
1260                      1265                      1270

Ala  Leu  Leu  Ala  Arg  Thr  Val  Glu  Thr  Lys  Leu  Asn  Gln  Asp  Ile  Thr
1275                      1280                      1285                      1290

Val  Thr  Ala  Ser  Gly  Asp  Gly  Lys  Ala  Thr  Met  Thr  Ile  Leu  Thr  Phe
               1295                      1300                      1305
```

```
Tyr Asn Ala Gln Leu Gln Glu Lys Ala Asn Val Cys Asn Lys Phe His
                1310                1315                1320
Leu Asn Val Ser Val Glu Asn Ile His Leu Asn Ala Met Gly Ala Lys
                1325                1330                1335
Gly Ala Leu Met Leu Lys Ile Cys Thr Arg Tyr Leu Gly Glu Val Asp
                1340                1345                1350
Ser Thr Met Thr Ile Ile Asp Ile Ser Met Leu Thr Gly Phe Leu Pro
1355                1360                1365                1370
Asp Ala Glu Asp Leu Thr Arg Leu Ser Lys Gly Val Asp Arg Tyr Ile
                1375                1380                1385
Ser Arg Tyr Glu Val Asp Asn Asn Met Ala Gln Lys Val Ala Val Ile
                1390                1395                1400
Ile Tyr Leu Asn Lys Val Ser His Ser Glu Asp Glu Cys Leu His Phe
                1405                1410                1415
Lys Ile Leu Lys His Phe Glu Val Gly Phe Ile Gln Pro Gly Ser Val
                1420                1425                1430
Lys Val Tyr Ser Tyr Tyr Asn Leu Asp Glu Lys Cys Thr Lys Phe Tyr
1435                1440                1445                1450
His Pro Asp Lys Gly Thr Gly Leu Leu Asn Lys Ile Cys Ile Gly Asn
                1455                1460                1465
Val Cys Arg Cys Ala Gly Glu Thr Cys Ser Ser Leu Asn His Gln Glu
                1470                1475                1480
Arg Ile Asp Val Pro Leu Gln Ile Glu Lys Ala Cys Glu Thr Asn Val
                1485                1490                1495
Asp Tyr Val Tyr Lys Thr Lys Leu Leu Arg Ile Glu Glu Gln Asp Gly
                1500                1505                1510
Asn Asp Ile Tyr Val Met Asp Val Leu Glu Val Ile Lys Gln Gly Thr
1515                1520                1525                1530
Asp Lys Asn Pro Arg Ala Lys Thr His Gln Tyr Ile Ser Gln Arg Lys
                1535                1540                1545
Cys Gln Glu Ala Leu Asn Leu Lys Val Asn Asp Asp Tyr Leu Ile Trp
                1550                1555                1560
Gly Ser Arg Ser Asp Leu Leu Pro Thr Lys Asp Lys Ile Ser Tyr Ile
                1565                1570                1575
Ile Thr Lys Asn Thr Trp Ile Glu Arg Trp Pro His Glu Asp Glu Cys
                1580                1585                1590
Gln Glu Glu Glu Phe Gln Lys Leu Cys Asp Asp Phe Ala Gln Phe Ser
1595                1600                1605                1610
Tyr Thr Leu Thr Glu Phe Gly Cys Pro Thr
                1615                1620
```

( 2 ) INFORMATION FOR SEQ ID NO:46:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

```
Glu Asp Gly Phe Ile Ala Asp Ser Asp Ile
1               5                   10
```

( 2 ) INFORMATION FOR SEQ ID NO:47:

( i ) SEQUENCE CHARACTERISTICS:

( A ) LENGTH: 10 amino acids
( B ) TYPE: amino acid
( D ) TOPOLOGY: linear ( i i ) MOLECULE TYPE: peptide ( v i ) ORIGINAL SOURCE:
( A ) ORGANISM: Naja naja ( x i ) SEQUENCE DESCRIPTION: SEQ ID NO:47:

Glu Asp Glu Leu Phe Gly Asp Asp Asn Ile
1               5                   10

( 2 ) INFORMATION FOR SEQ ID NO:48:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( v i ) ORIGINAL SOURCE:
( A ) ORGANISM: Homo sapiens ( x i ) SEQUENCE DESCRIPTION: SEQ ID NO:48:

Asp Glu Asp Ile Ile Ala Glu Glu Asn Ile
1               5                   10

( 2 ) INFORMATION FOR SEQ ID NO:49:

( i ) SEQUENCE CHARACTERISTICS:
( A ) LENGTH: 30 amino acids
( B ) TYPE: amino acid
( D ) TOPOLOGY: linear ( i i ) MOLECULE TYPE: peptide ( x i ) SEQUENCE DESCRIPTION: SEQ ID NO:49:

Val Asp Arg Tyr Ile Ser Arg Tyr Glu Val Asp Asn Asn Met Ala Gln
1               5                   10                  15
Lys Val Ala Val Ile Ile Tyr Leu Asn Lys Val Ser His Ser
            20                  25                  30

( 2 ) INFORMATION FOR SEQ ID NO:50:

( i ) SEQUENCE CHARACTERISTICS:
( A ) LENGTH: 30 amino acids
( B ) TYPE: amino acid
( D ) TOPOLOGY: linear ( i i ) MOLECULE TYPE: peptide ( v i ) ORIGINAL SOURCE:
( A ) ORGANISM: Naja naja ( x i ) SEQUENCE DESCRIPTION: SEQ ID NO:50:

Val Asp Arg Tyr Ile Ser Lys Phe Glu Ile Asp Asn Asn Met Ala Gln
1               5                   10                  15
Lys Gly Thr Val Val Ile Tyr Leu Asp Lys Val Ser His Ser
            20                  25                  30

( 2 ) INFORMATION FOR SEQ ID NO:51:

( i ) SEQUENCE CHARACTERISTICS:
( A ) LENGTH: 30 amino acids
( B ) TYPE: amino acid
( D ) TOPOLOGY: linear ( i i ) MOLECULE TYPE: peptide (v i) ORIGINAL SOURCE:
   (A) ORGANISM: Homo sapiens (x i) SEQUENCE DESCRIPTION: SEQ ID NO:51:

Val Asp Arg Tyr Ile Ser Lys Tyr Glu Leu Asp Lys Ala Phe Ser Asp
1               5                   10                  15

Arg Asn Thr Leu Ile Ile Tyr Leu Asp Lys Val Ser His Ser
            20                  25                  30

(2) INFORMATION FOR SEQ ID NO:52:

(i) SEQUENCE CHARACTERISTICS:
      (A) LENGTH: 26 amino acids
      (B) TYPE: amino acid
      (D) TOPOLOGY: linear (i i) MOLECULE TYPE: peptide (x i) SEQUENCE DESCRIPTION: SEQ ID NO:52:

Leu Ile Ile Thr Pro Ser Gly Cys Gly Gln Asn Met Ile Arg Met
1               5                   10                  15

Ala Ala Pro Val Ile Ala Thr Tyr Tyr Leu
            20                  25

(2) INFORMATION FOR SEQ ID NO:53:

(i) SEQUENCE CHARACTERISTICS:
      (A) LENGTH: 26 amino acids
      (B) TYPE: amino acid
      (D) TOPOLOGY: linear (i i) MOLECULE TYPE: peptide (v i) ORIGINAL SOURCE:
      (A) ORGANISM: Naja naja (x i) SEQUENCE DESCRIPTION: SEQ ID NO:53:

Leu Ile Ile Thr Pro Ser Gly Cys Gly Gln Asn Met Ile Thr Met
1               5                   10                  15

Thr Pro Ser Val Ile Ala Thr Tyr Tyr Leu
            20                  25

(2) INFORMATION FOR SEQ ID NO:54:

(i) SEQUENCE CHARACTERISTICS:
      (A) LENGTH: 26 amino acids
      (B) TYPE: amino acid
      (D) TOPOLOGY: linear (i i) MOLECULE TYPE: peptide (v i) ORIGINAL SOURCE:
      (A) ORGANISM: Homo sapiens (x i) SEQUENCE DESCRIPTION: SEQ ID NO:54:

Leu Ile Val Thr Pro Ser Gly Cys Gly Gln Asn Met Ile Gly Met
1               5                   10                  15

Thr Pro Thr Val Ile Ala Val His Tyr Leu
            20                  25

(2) INFORMATION FOR SEQ ID NO:55:

(i) SEQUENCE CHARACTERISTICS:
      (A) LENGTH: 14 amino acids
      (B) TYPE: amino acid
      (D) TOPOLOGY: linear ( i i ) MOLECULE TYPE: peptide ( x i ) SEQUENCE DESCRIPTION: SEQ ID NO:55:

Leu Ala Arg Asp Asp Asn Glu Asp Gly Phe Ile Ala Asp Ser
1               5                   10

( 2 ) INFORMATION FOR SEQ ID NO:56:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( v i ) ORIGINAL SOURCE:
( A ) ORGANISM: Naja naja ( x i ) SEQUENCE DESCRIPTION: SEQ ID NO:56:

Leu Ala Arg Ser Asp Phe Glu Asp Glu Leu Phe Gly Asp Asp
1               5                   10

( 2 ) INFORMATION FOR SEQ ID NO:57:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( v i ) ORIGINAL SOURCE:
( A ) ORGANISM: Homo sapiens ( x i ) SEQUENCE DESCRIPTION: SEQ ID NO:57:

Leu Ala Arg Ser Asn Leu Asp Glu Asp Ile Ile Ala Glu Glu
1               5                   10

( 2 ) INFORMATION FOR SEQ ID NO:58:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:58:

Asp Asp Asn Glu Asp Gly Phe Ile Ala Asp Ser Asp Ile Ile Ser Arg
1               5                   10                  15

Ser Asp Phe Pro Lys
            20

( 2 ) INFORMATION FOR SEQ ID NO:59:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( v i ) ORIGINAL SOURCE:
( A ) ORGANISM: Naja naja ( x i ) SEQUENCE DESCRIPTION: SEQ ID NO:59:

Ser Asp Phe Glu Asp Glu Leu Phe Gly Asp Asp Asn Ile Ile Ser Arg
1               5                   10                  15

Ser Asp Phe Pro Glu

20

(2) INFORMATION FOR SEQ ID NO:60:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (vi) ORIGINAL SOURCE:
        (A) ORGANISM: Homo sapiens (xi) SEQUENCE DESCRIPTION: SEQ ID NO:60:

```
Ser  Asn  Leu  Asp  Glu  Asp  Ile  Ile  Ala  Glu  Glu  Asn  Ile  Val  Ser  Arg
 1                  5                            10                       15
Ser  Glu  Phe  Pro  Glu
                    20
```

(2) INFORMATION FOR SEQ ID NO:61:

(i) SEQUENCE CHARACTERISTICS:
        (A) LENGTH: 63 amino acids
        (B) TYPE: amino acid
        (D) TOPOLOGY: linear (ii) MOLECULE TYPE: peptide (xi) SEQUENCE DESCRIPTION: SEQ ID NO:61:

```
Val  Leu  Met  Ala  Ala  Ser  Thr  Gly  Arg  Asp  His  Trp  Glu  Glu  Tyr  Asn
 1                  5                            10                       15
Ala  His  Thr  His  Asn  Ile  Glu  Gly  Thr  Ser  Tyr  Ala  Leu  Leu  Ala  Leu
                    20                      25                       30
Leu  Lys  Met  Lys  Lys  Phe  Asp  Gln  Thr  Gly  Pro  Ile  Val  Arg  Trp  Leu
               35                      40                  45
Thr  Asp  Gln  Asn  Phe  Tyr  Gly  Glu  Thr  Tyr  Gly  Gln  Thr  Gln  Ala
          50                      55                      60
```

(2) INFORMATION FOR SEQ ID NO:62:

(i) SEQUENCE CHARACTERISTICS:
        (A) LENGTH: 63 amino acids
        (B) TYPE: amino acid
        (D) TOPOLOGY: linear (ii) MOLECULE TYPE: peptide (vi) ORIGINAL SOURCE:
        (A) ORGANISM: Naja naja (xi) SEQUENCE DESCRIPTION: SEQ ID NO:62:

```
Val  Leu  Met  Ala  Ala  Ser  Thr  Gly  Arg  Asn  Arg  Trp  Glu  Glu  Tyr  Asn
 1                  5                            10                       15
Ala  Arg  Thr  His  Asn  Ile  Glu  Gly  Thr  Ser  Tyr  Ala  Leu  Leu  Ala  Leu
                    20                      25                       30
Leu  Lys  Met  Lys  Lys  Phe  Val  Glu  Ala  Gly  Pro  Val  Val  Arg  Trp  Leu
               35                      40                  45
Ile  Asp  Gln  Lys  Tyr  Tyr  Gly  Gly  Thr  Tyr  Gly  Gln  Thr  Gln  Ala
          50                      55                      60
```

(2) INFORMATION FOR SEQ ID NO:63:

(i) SEQUENCE CHARACTERISTICS:
        (A) LENGTH: 63 amino acids
        (B) TYPE: amino acid ( D ) TOPOLOGY: linear ( i i ) MOLECULE TYPE: peptide ( v i ) ORIGINAL SOURCE:
    ( A ) ORGANISM: Homo sapiens ( x i ) SEQUENCE DESCRIPTION: SEQ ID NO:63:

| Lys | Phe | Leu | Thr | Thr | Ala | Lys | Asp | Lys | Asn | Arg | Trp | Glu | Asp | Pro | Gly |
|---|---|---|---|---|---|---|---|---|---|---|---|---|---|---|---|
| 1 | | | | 5 | | | | | 10 | | | | | 15 | |

| Lys | Gln | Leu | Tyr | Asn | Val | Glu | Ala | Thr | Ser | Tyr | Ala | Leu | Leu | Ala | Leu |
|---|---|---|---|---|---|---|---|---|---|---|---|---|---|---|---|
| | | | 20 | | | | | 25 | | | | | 30 | | |

| Leu | Gln | Leu | Lys | Asp | Phe | Asp | Phe | Val | Pro | Pro | Val | Val | Arg | Trp | Leu |
|---|---|---|---|---|---|---|---|---|---|---|---|---|---|---|---|
| | | 35 | | | | | 40 | | | | | 45 | | | |

| Asn | Glu | Gln | Arg | Tyr | Tyr | Gly | Gly | Gly | Tyr | Gly | Ser | Thr | Gln | Ala |
|---|---|---|---|---|---|---|---|---|---|---|---|---|---|---|
| | 50 | | | | | 55 | | | | | 60 | | | |

( 2 ) INFORMATION FOR SEQ ID NO:64:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Naja naja ( x i ) SEQUENCE DESCRIPTION: SEQ ID NO:64:

| Ala | Leu | Tyr | Thr | Leu | Ile | Thr | Pro | Ala | Val | Leu | Arg | Thr | Asp | Thr |
|---|---|---|---|---|---|---|---|---|---|---|---|---|---|---|
| 1 | | | | 5 | | | | | 10 | | | | | 15 |

( 2 ) INFORMATION FOR SEQ ID NO:65:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:65:

| Ser | Pro | Met | Tyr | Ser | Ile | Ile | Thr | Pro | Asn | Ile | Leu | Arg | Leu | Glu | Ser |
|---|---|---|---|---|---|---|---|---|---|---|---|---|---|---|---|
| 1 | | | | 5 | | | | | 10 | | | | | 15 | |

( 2 ) INFORMATION FOR SEQ ID NO:66:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:66:

| Ile | Pro | Met | Tyr | Ser | Ile | Ile | Thr | Pro | Asn | Val | Leu | Arg | Leu | Glu | Ser |
|---|---|---|---|---|---|---|---|---|---|---|---|---|---|---|---|
| 1 | | | | 5 | | | | | 10 | | | | | 15 | |

( 2 ) INFORMATION FOR SEQ ID NO:67:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:67:

Glu Ile Gln Met Pro Thr His Lys Asp Leu Asn Leu Asp Ile Thr Ile
1               5                   10                  15

Glu Leu Pro Asp Arg Glu Val
            20

( 2 ) INFORMATION FOR SEQ ID NO:68:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Naja naja ( x i ) SEQUENCE DESCRIPTION: SEQ ID NO:68:

Glu Ile Gln Met Pro Thr His Gln Asp Leu Asn Leu Asp Ile Ser Ile
1               5                   10                  15

Lys Leu Pro Glu Arg Glu Val
            20

( 2 ) INFORMATION FOR SEQ ID NO:69:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:69:

Gln Lys Asp Ala Pro Asp His Gln Glu Leu Asn Leu Asp Val Ser Leu
1               5                   10                  15

Gln Leu Pro Ser Arg Ser Ser
            20

( 2 ) INFORMATION FOR SEQ ID NO:70:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:70:

Gln Thr Asp Val Pro Asp His Lys Asp Leu Asn Met Asp Val Ser Phe
1               5                   10                  15

His Leu Pro Ser Arg Ser Ser
            20

( 2 ) INFORMATION FOR SEQ ID NO:71:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:71:

Asp Asp Asn Glu Asp Gly Phe Ile Ala Asp Ser Asp Ile Ile Ser Arg
1               5                           10                          15

Ser Asp Phe Pro Lys Ser
              20

( 2 ) INFORMATION FOR SEQ ID NO:72:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Naja naja ( x i ) SEQUENCE DESCRIPTION: SEQ ID NO:72:

Ser Asp Phe Glu Asp Glu Leu Phe Gly Asp Asp Asn Ile Ile Ser Arg
1               5                           10                          15

Ser Asp Phe Pro Glu Ser
              20

( 2 ) INFORMATION FOR SEQ ID NO:73:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:73:

Ser Asn Leu Asp Glu Asp Ile Ile Ala Glu Glu Asn Ile Val Ser Arg
1               5                           10                          15

Ser Glu Phe Pro Glu Ser
              20

( 2 ) INFORMATION FOR SEQ ID NO:74:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:74:

Ser Glu Leu Glu Glu Asp Ile Ile Pro Glu Glu Asp Ile Ile Ser Arg
1               5                           10                          15

Ser His Phe Pro Gln Ser
              20

( 2 ) INFORMATION FOR SEQ ID NO:75:

( i ) SEQUENCE CHARACTERISTICS:
        ( A ) LENGTH: 4138 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:

(A) NAME/KEY: CDS
(B) LOCATION: 3..4001

(xi) SEQUENCE DESCRIPTION: SEQ ID NO:75:

| | | | | | | | | | | | | | | | | |
|---|---|---|---|---|---|---|---|---|---|---|---|---|---|---|---|---|
| GA | ATT | CCA | TCA | GGA | GGT | GAT | ATG | GTA | ATG | ACT | GAG | CAA | AGT | GGC | ATT | 47 |
| | Ile | Pro | Ser | Gly | Gly | Asp | Met | Val | Met | Thr | Glu | Gln | Ser | Gly | Ile | |
| | 1 | | | | 5 | | | | | 10 | | | | | 15 | |
| CAT | ATT | GTG | ACA | TCT | CCC | TAT | CAG | ATC | TAC | TTC | ACA | AAA | ACC | CCC | AAA | 95 |
| His | Ile | Val | Thr | Ser | Pro | Tyr | Gln | Ile | Tyr | Phe | Thr | Lys | Thr | Pro | Lys | |
| | | | | 20 | | | | | 25 | | | | | 30 | | |
| TAT | TTC | AAG | CCA | GGA | ATG | CCA | TAT | GAA | CTG | ACG | GTG | TAT | GTT | ACC | AAA | 143 |
| Tyr | Phe | Lys | Pro | Gly | Met | Pro | Tyr | Glu | Leu | Thr | Val | Tyr | Val | Thr | Lys | |
| | | | 35 | | | | | 40 | | | | | 45 | | | |
| CCT | GAT | GGC | TCA | CCA | GCT | GCC | CAT | GTG | CCA | GTG | GTA | TCA | GAG | GCC | ATT | 191 |
| Pro | Asp | Gly | Ser | Pro | Ala | Ala | His | Val | Pro | Val | Val | Ser | Glu | Ala | Ile | |
| | | 50 | | | | | 55 | | | | | 60 | | | | |
| CAT | TCT | GAG | GGA | ACC | ACT | TTG | AGT | GAT | GGG | ACT | GCT | AAG | CTC | TTC | CTG | 239 |
| His | Ser | Glu | Gly | Thr | Thr | Leu | Ser | Asp | Gly | Thr | Ala | Lys | Leu | Phe | Leu | |
| | 65 | | | | | 70 | | | | | 75 | | | | | |
| AAC | ACA | CCA | CAA | AAT | GCT | CAA | AGC | CTA | CCG | ATC | ACT | GTT | AGA | ACT | AAC | 287 |
| Asn | Thr | Pro | Gln | Asn | Ala | Gln | Ser | Leu | Pro | Ile | Thr | Val | Arg | Thr | Asn | |
| 80 | | | | | 85 | | | | | 90 | | | | | 95 | |
| CAT | GGA | GAC | CTC | CCA | AGA | GAA | CGC | CAG | GCA | ATA | AAG | TCC | ATG | ACA | GCC | 335 |
| His | Gly | Asp | Leu | Pro | Arg | Glu | Arg | Gln | Ala | Ile | Lys | Ser | Met | Thr | Ala | |
| | | | | 100 | | | | | 105 | | | | | 110 | | |
| ACA | GCC | TAC | CAA | ACC | CAG | GGA | GGA | TCT | GGA | AAC | TAT | CTT | CAT | GTA | GCC | 383 |
| Thr | Ala | Tyr | Gln | Thr | Gln | Gly | Gly | Ser | Gly | Asn | Tyr | Leu | His | Val | Ala | |
| | | | 115 | | | | | 120 | | | | | 125 | | | |
| ATT | ACA | TCT | ACA | GAG | ATT | AAG | CCC | GGA | GAT | AAC | TTA | CCT | GTC | AAT | TTC | 431 |
| Ile | Thr | Ser | Thr | Glu | Ile | Lys | Pro | Gly | Asp | Asn | Leu | Pro | Val | Asn | Phe | |
| | | 130 | | | | | 135 | | | | | 140 | | | | |
| AAT | GTG | AGG | GGC | AAT | GCA | AAT | TCA | CTG | AAC | CAG | ATC | AAA | TAT | TTC | ACA | 479 |
| Asn | Val | Arg | Gly | Asn | Ala | Asn | Ser | Leu | Asn | Gln | Ile | Lys | Tyr | Phe | Thr | |
| | 145 | | | | | 150 | | | | | 155 | | | | | |
| TAC | CTC | ATA | CTG | AAT | AAA | GGG | AAG | ATT | TTC | AAG | GTT | GGC | AGG | CAA | CAC | 527 |
| Tyr | Leu | Ile | Leu | Asn | Lys | Gly | Lys | Ile | Phe | Lys | Val | Gly | Arg | Gln | His | |
| 160 | | | | | 165 | | | | | 170 | | | | | 175 | |
| AGG | GGA | GAT | GGG | GAG | AAT | CTG | GTG | ACC | ATG | AAT | CTA | CAT | ATC | ACT | CCA | 575 |
| Arg | Gly | Asp | Gly | Glu | Asn | Leu | Val | Thr | Met | Asn | Leu | His | Ile | Thr | Pro | |
| | | | | 180 | | | | | 185 | | | | | 190 | | |
| GAT | CTC | ATT | CCT | TCC | TTC | CGG | TTT | GTG | GCT | TAC | TAC | CAA | GTG | GGA | AAC | 623 |
| Asp | Leu | Ile | Pro | Ser | Phe | Arg | Phe | Val | Ala | Tyr | Tyr | Gln | Val | Gly | Asn | |
| | | | 195 | | | | | 200 | | | | | 205 | | | |
| AAT | GAA | ATT | GTG | GCT | GAT | TCT | GTC | TGG | GTG | GAT | GTG | AAG | GAT | ACC | TGC | 671 |
| Asn | Glu | Ile | Val | Ala | Asp | Ser | Val | Trp | Val | Asp | Val | Lys | Asp | Thr | Cys | |
| | | 210 | | | | | 215 | | | | | 220 | | | | |
| ATG | GGA | ACG | TTG | GTT | GTG | AAA | GGA | GCG | ACT | TCC | AGA | GAC | AAT | CGA | ATA | 719 |
| Met | Gly | Thr | Leu | Val | Val | Lys | Gly | Ala | Thr | Ser | Arg | Asp | Asn | Arg | Ile | |
| | 225 | | | | | 230 | | | | | 235 | | | | | |
| CAA | ATG | CCA | GGA | GCT | GCA | ATG | AAA | ATC | AAA | TTG | GAA | GGG | GAT | CCA | GGT | 767 |
| Gln | Met | Pro | Gly | Ala | Ala | Met | Lys | Ile | Lys | Leu | Glu | Gly | Asp | Pro | Gly | |
| 240 | | | | | 245 | | | | | 250 | | | | | 255 | |
| GCT | TGG | ATT | GGT | CTT | GTG | GCT | GTG | GAC | AAA | GCA | GAA | TAT | GTT | CTC | AAT | 815 |
| Ala | Trp | Ile | Gly | Leu | Val | Ala | Val | Asp | Lys | Ala | Glu | Tyr | Val | Leu | Asn | |
| | | | | 260 | | | | | 265 | | | | | 270 | | |
| GAT | AAA | TAT | AAG | ATT | AGC | CAA | GCT | AAG | ATA | TGG | GAC | ACA | ATA | GAA | AAG | 863 |
| Asp | Lys | Tyr | Lys | Ile | Ser | Gln | Ala | Lys | Ile | Trp | Asp | Thr | Ile | Glu | Lys | |
| | | | 275 | | | | | 280 | | | | | 285 | | | |
| AGT | GAC | TTT | GGC | TGT | ACA | GCT | GGC | AGT | GGC | CAG | AAT | AAT | CTG | GGT | GTG | 911 |
| Ser | Asp | Phe | Gly | Cys | Thr | Ala | Gly | Ser | Gly | Gln | Asn | Asn | Leu | Gly | Val | |
| | | 290 | | | | | 295 | | | | | 300 | | | | |

| | |
|---|---|
| TTT GAA GAT GCT GGA CTG GCT CTG ACA ACC AGC ACT AAT CTC AAC ACC<br>Phe Glu Asp Ala Gly Leu Ala Leu Thr Thr Ser Thr Asn Leu Asn Thr<br>305                            310                         315 | 959 |
| AAA CAG AGA TCA GCT GCA AAG TGT CCT CAG CCT GCA AAT CGG AGG CGT<br>Lys Gln Arg Ser Ala Ala Lys Cys Pro Gln Pro Ala Asn Arg Arg Arg<br>320                         325                        330                        335 | 1007 |
| CGC AGT TCT GTT TTG CTG CTT GAC AGC AAC GCA AGC AAA GCG GCA CAG<br>Arg Ser Ser Val Leu Leu Leu Asp Ser Asn Ala Ser Lys Ala Ala Gln<br>                         340                        345                        350 | 1055 |
| TTT CAG GAT CAA GAC CTG CGT AAA TGC TGT GAA GAT GGC ATG CAT GAG<br>Phe Gln Asp Gln Asp Leu Arg Lys Cys Cys Glu Asp Gly Met His Glu<br>               355                        360                        365 | 1103 |
| AAC CCC ATG GGG CAC ACT TGT GAA AAG CGT GAA AAA TAC ATC CAG GAG<br>Asn Pro Met Gly His Thr Cys Glu Lys Arg Glu Lys Tyr Ile Gln Glu<br>          370                        375                        380 | 1151 |
| GGA GAT GCT TGT AAG GCT GCC TTC CTC GAA TGC TGT CAC TAC ATC AAA<br>Gly Asp Ala Cys Lys Ala Ala Phe Leu Glu Cys Cys His Tyr Ile Lys<br>385                            390                         395 | 1199 |
| GGG ATC CAA GAT GAC AAT AAA CGG GAG AGC GAG TTG TTT CTG GCA AGA<br>Gly Ile Gln Asp Asp Asn Lys Arg Glu Ser Glu Leu Phe Leu Ala Arg<br>400                            405                        410                        415 | 1247 |
| AGT GAT TTT GAA GAT GAT TTA TTT GGA GAA GGT AAC ATC ACC TCA AGG<br>Ser Asp Phe Glu Asp Asp Leu Phe Gly Glu Gly Asn Ile Thr Ser Arg<br>                         420                        425                        430 | 1295 |
| TCT GAT TTT CCT GAG AGT TGG TTG TGG CTA ATG GAG CAG CTG TCT GAA<br>Ser Asp Phe Pro Glu Ser Trp Leu Trp Leu Met Glu Gln Leu Ser Glu<br>               435                        440                        445 | 1343 |
| CAT CCT AAC AGT AAA GGG ATT TCA AGC AAG ATA GTA CCT TTT TAT CTG<br>His Pro Asn Ser Lys Gly Ile Ser Ser Lys Ile Val Pro Phe Tyr Leu<br>          450                        455                        460 | 1391 |
| AGG GAT TCC ATC ACA ACC TGG GAG TTG CTG GCT GTG GGC CTT TCA CCC<br>Arg Asp Ser Ile Thr Thr Trp Glu Leu Leu Ala Val Gly Leu Ser Pro<br>465                            470                         475 | 1439 |
| ACC AAA GGG ATC TGT GTG GCT GAA CCT TAT GAA ATA ACA GTC ATG AAA<br>Thr Lys Gly Ile Cys Val Ala Glu Pro Tyr Glu Ile Thr Val Met Lys<br>480                            485                        490                        495 | 1487 |
| GAC TTC TTC ATT GAT CTT CAA CTG CCG TAT TCA GTA GTG AAG AAT GAG<br>Asp Phe Phe Ile Asp Leu Gln Leu Pro Tyr Ser Val Val Lys Asn Glu<br>                         500                        505                        510 | 1535 |
| CAG GTG AAA ATT CGA GCT GTT TTG TAC AAC TAC GCT GAC AAG GAT ATT<br>Gln Val Lys Ile Arg Ala Val Leu Tyr Asn Tyr Ala Asp Lys Asp Ile<br>               515                        520                        525 | 1583 |
| TAT GTA CGA GTG GAA CTG TTA TAC AGC CCA GCC TTC TGC AGT GCT TCC<br>Tyr Val Arg Val Glu Leu Leu Tyr Ser Pro Ala Phe Cys Ser Ala Ser<br>          530                        535                        540 | 1631 |
| ACA GAA AGT CAA AGA TAC CGA GAG CAG TTG CCA ATT AAA GCC CTG TCC<br>Thr Glu Ser Gln Arg Tyr Arg Glu Gln Leu Pro Ile Lys Ala Leu Ser<br>545                            550                        555 | 1679 |
| TCC AGG GCA GTA TCG TTT GTG ATA GTC CCA TTA GAG CAA GGA TTG CAT<br>Ser Arg Ala Val Ser Phe Val Ile Val Pro Leu Glu Gln Gly Leu His<br>560                            565                        570                        575 | 1727 |
| GAT GTT GAG GTT ACA GCA AGT GTC CAG GGA GAG TTG ATG TCA GAT GGT<br>Asp Val Glu Val Thr Ala Ser Val Gln Gly Glu Leu Met Ser Asp Gly<br>                         580                        585                        590 | 1775 |
| GTG AAG AAG AAA CTG AAA GTT GTA CCT GAA GGG GAA TGG AAA AGT ATT<br>Val Lys Lys Lys Leu Lys Val Val Pro Glu Gly Glu Trp Lys Ser Ile<br>               595                        600                        605 | 1823 |
| GTT ACT ATT ATT GAA CTG GAC CCA CAT ACA AAA GGA ATT GGT GGA ACA<br>Val Thr Ile Ile Glu Leu Asp Pro His Thr Lys Gly Ile Gly Gly Thr<br>          610                        615                        620 | 1871 |

| | | | | | | | | | | | | | | | | |
|---|---|---|---|---|---|---|---|---|---|---|---|---|---|---|---|---|
| CAG | GTA | GAA | TTG | GTC | AAA | GCC | AAT | AAA | TTA | AAT | GAC | AGG | GTT | CCT | GAT | 1919 |
| Gln | Val | Glu | Leu | Val | Lys | Ala | Asn | Lys | Leu | Asn | Asp | Arg | Val | Pro | Asp | |
| | 625 | | | | 630 | | | | | | 635 | | | | | |
| ACG | GAA | ATA | GAA | ACC | AAG | ATT | ACT | ATT | CAA | GGT | GAT | CCT | GTG | GCT | CAG | 1967 |
| Thr | Glu | Ile | Glu | Thr | Lys | Ile | Thr | Ile | Gln | Gly | Asp | Pro | Val | Ala | Gln | |
| 640 | | | | | 645 | | | | | 650 | | | | | 655 | |
| ACT | ATT | GAA | AAC | TCA | ATT | GAT | GGA | AGT | AAA | CTC | AAC | CAT | CTC | ATT | ATC | 2015 |
| Thr | Ile | Glu | Asn | Ser | Ile | Asp | Gly | Ser | Lys | Leu | Asn | His | Leu | Ile | Ile | |
| | | | | 660 | | | | | 665 | | | | | 670 | | |
| ACT | CCT | TTT | GGC | TGT | GGG | GAG | CAA | AAT | ATG | ATC | CGC | ATG | ACT | GCA | CCA | 2063 |
| Thr | Pro | Phe | Gly | Cys | Gly | Glu | Gln | Asn | Met | Ile | Arg | Met | Thr | Ala | Pro | |
| | | | 675 | | | | | 680 | | | | | 685 | | | |
| GTT | ATT | GCC | ACC | TAC | TAC | CTG | GAC | ACC | ACA | CAG | CAG | TGG | GAG | ACT | CTC | 2111 |
| Val | Ile | Ala | Thr | Tyr | Tyr | Leu | Asp | Thr | Thr | Gln | Gln | Trp | Glu | Thr | Leu | |
| | | 690 | | | | | 695 | | | | | 700 | | | | |
| GGC | ATA | AAT | CGC | AGG | ACT | GAA | GCT | GTC | AAT | CAG | ATC | ATG | ACT | GGT | TAT | 2159 |
| Gly | Ile | Asn | Arg | Arg | Thr | Glu | Ala | Val | Asn | Gln | Ile | Met | Thr | Gly | Tyr | |
| | 705 | | | | | 710 | | | | | 715 | | | | | |
| GCC | CAG | CAG | TTG | GTG | TAC | AAG | AAA | GCA | GAC | CAT | TCC | TAT | GCA | GCA | TTT | 2207 |
| Ala | Gln | Gln | Leu | Val | Tyr | Lys | Lys | Ala | Asp | His | Ser | Tyr | Ala | Ala | Phe | |
| 720 | | | | | 725 | | | | | 730 | | | | | 735 | |
| ACA | AAC | AGT | GCA | TCT | AGT | TCT | TGG | CTA | ACA | GCA | TAT | GTT | GTA | AAA | ATC | 2255 |
| Thr | Asn | Ser | Ala | Ser | Ser | Ser | Trp | Leu | Thr | Ala | Tyr | Val | Val | Lys | Ile | |
| | | | | 740 | | | | | 745 | | | | | 750 | | |
| TTT | GCC | TTG | GCT | GCC | AAA | ATT | GTA | AAA | GAC | ATT | AAC | CAT | GAA | ATC | GTT | 2303 |
| Phe | Ala | Leu | Ala | Ala | Lys | Ile | Val | Lys | Asp | Ile | Asn | His | Glu | Ile | Val | |
| | | | 755 | | | | | 760 | | | | | 765 | | | |
| TGT | GGA | GGT | ATG | AGG | TGG | CTG | ATT | CTG | AAC | AGG | CAA | CGA | ACA | GAT | GGA | 2351 |
| Cys | Gly | Gly | Met | Arg | Trp | Leu | Ile | Leu | Asn | Arg | Gln | Arg | Thr | Asp | Gly | |
| | | 770 | | | | | 775 | | | | | 780 | | | | |
| GTG | TTC | AGA | GAA | AAC | GCC | CCT | GTA | CTT | TTT | GGA | ACA | ATG | CAG | GGA | GGC | 2399 |
| Val | Phe | Arg | Glu | Asn | Ala | Pro | Val | Leu | Phe | Gly | Thr | Met | Gln | Gly | Gly | |
| | 785 | | | | | 790 | | | | | 795 | | | | | |
| ATT | CAA | GGT | GCT | GAA | CCA | GAA | GGA | TCT | TTA | ACA | GCT | TTC | ATT | CTG | GTT | 2447 |
| Ile | Gln | Gly | Ala | Glu | Pro | Glu | Gly | Ser | Leu | Thr | Ala | Phe | Ile | Leu | Val | |
| 800 | | | | | 805 | | | | | 810 | | | | | 815 | |
| GCG | TTG | TTG | GAA | TCC | AGA | TCA | ATC | TGC | AAT | GCA | TAT | ATC | AAT | ATT | CTA | 2495 |
| Ala | Leu | Leu | Glu | Ser | Arg | Ser | Ile | Cys | Asn | Ala | Tyr | Ile | Asn | Ile | Leu | |
| | | | | 820 | | | | | 825 | | | | | 830 | | |
| GAC | AGC | AGC | ATC | AGT | AAG | GCC | ACA | GAT | TAT | TTA | CTC | AAA | AAG | TAT | GAG | 2543 |
| Asp | Ser | Ser | Ile | Ser | Lys | Ala | Thr | Asp | Tyr | Leu | Leu | Lys | Lys | Tyr | Glu | |
| | | | 835 | | | | | 840 | | | | | 845 | | | |
| AAA | CTG | CAA | AGG | CCT | TAC | ACT | ACA | GCC | CTC | ACA | GCC | TAT | GCT | TTG | GCT | 2591 |
| Lys | Leu | Gln | Arg | Pro | Tyr | Thr | Thr | Ala | Leu | Thr | Ala | Tyr | Ala | Leu | Ala | |
| | | 850 | | | | | 855 | | | | | 860 | | | | |
| GCT | GCA | GAA | CGA | CTC | AAT | GAT | GAC | AGG | GTA | CTC | ATG | GCA | GCA | TCA | ACA | 2639 |
| Ala | Ala | Glu | Arg | Leu | Asn | Asp | Asp | Arg | Val | Leu | Met | Ala | Ala | Ser | Thr | |
| | 865 | | | | | 870 | | | | | 875 | | | | | |
| GGA | AGG | AAT | CGT | TGG | GAA | GAA | CCT | AAC | GCC | CAC | ACC | CAT | AAC | ATT | GAA | 2687 |
| Gly | Arg | Asn | Arg | Trp | Glu | Glu | Pro | Asn | Ala | His | Thr | His | Asn | Ile | Glu | |
| 880 | | | | | 885 | | | | | 890 | | | | | 895 | |
| GGC | ACT | TCC | TAT | GCC | TTG | TTG | GCC | CTG | CTG | AAA | ATG | AAG | AAA | TTT | GTT | 2735 |
| Gly | Thr | Ser | Tyr | Ala | Leu | Leu | Ala | Leu | Leu | Lys | Met | Lys | Lys | Phe | Val | |
| | | | | 900 | | | | | 905 | | | | | 910 | | |
| GAG | GCC | GGT | CCT | GTA | GTC | CAA | TGG | CTG | ATA | GAT | CAG | CAA | TAT | TAT | GGG | 2783 |
| Glu | Ala | Gly | Pro | Val | Val | Gln | Trp | Leu | Ile | Asp | Gln | Gln | Tyr | Tyr | Gly | |
| | | | 915 | | | | | 920 | | | | | 925 | | | |
| GGA | ACA | TAT | GGA | CAA | ACC | CAA | GCA | ACA | GTT | ATG | ATG | TTT | CAA | GCT | CTT | 2831 |
| Gly | Thr | Tyr | Gly | Gln | Thr | Gln | Ala | Thr | Val | Met | Met | Phe | Gln | Ala | Leu | |
| | | 930 | | | | | 935 | | | | | 940 | | | | |

```
GCT GAA TAT GAG ATT CAG ATG CCT ACC CAT AAG GAC TTA AAC TTA GAT       2879
Ala Glu Tyr Glu Ile Gln Met Pro Thr His Lys Asp Leu Asn Leu Asp
    945                 950                 955

ATT ACT ATT GAA CTG CCA GAT CGA GAA GTA CCT ATA AGG TAC AGA ATT       2927
Ile Thr Ile Glu Leu Pro Asp Arg Glu Val Pro Ile Arg Tyr Arg Ile
960                 965                 970                 975

AAT TAT GAA AAT GCT CTC CTG GCT CAG ACA GTA GAG ACC AAA CTC AAC       2975
Asn Tyr Glu Asn Ala Leu Leu Ala Gln Thr Val Glu Thr Lys Leu Asn
                980                 985                 990

GAA GAC TTC ACT GTG TCA GCA TCA GGT GAT GGA AAA GCA ACA ATG ACC       3023
Glu Asp Phe Thr Val Ser Ala Ser Gly Asp Gly Lys Ala Thr Met Thr
            995                 1000                1005

ATT TTG ACG GTC TAT AAT GCA CAA TTG AGG GAG GAT GCA AAT GTT TGC       3071
Ile Leu Thr Val Tyr Asn Ala Gln Leu Arg Glu Asp Ala Asn Val Cys
    1010                1015                1020

AAC AAA TTC CAT CTT GAT GTT TCT GTT GAA AAC GTC CAG TTG AAC TTA       3119
Asn Lys Phe His Leu Asp Val Ser Val Glu Asn Val Gln Leu Asn Leu
1025                1030                1035

AAA GAG GCA AAG GGA GCC AAG GGA GCC CTC AAG CTC AAA ATC TGC ACT       3167
Lys Glu Ala Lys Gly Ala Lys Gly Ala Leu Lys Leu Lys Ile Cys Thr
1040                1045                1050                1055

AGG TAT CTG GGA GAA GTT GAT TCT ACA ATG ACA ATA ATT GAT GTT TCT       3215
Arg Tyr Leu Gly Glu Val Asp Ser Thr Met Thr Ile Ile Asp Val Ser
                1060                1065                1070

ATG CTG ACT GGT TTT GTC CCT GAT ACT GAA GAC CTT ACG AGG CTT TCT       3263
Met Leu Thr Gly Phe Val Pro Asp Thr Glu Asp Leu Thr Arg Leu Ser
            1075                1080                1085

AAA GGA GTC GAC AGA TAT ATC TCC ATG TTT GAA ATT AAC AAT AAT ATG       3311
Lys Gly Val Asp Arg Tyr Ile Ser Met Phe Glu Ile Asn Asn Asn Met
        1090                1095                1100

GCT CAG AAA GGA ACT GTT ATC ATT TAC TTA GAC AAG GTC TCC CAC TCT       3359
Ala Gln Lys Gly Thr Val Ile Ile Tyr Leu Asp Lys Val Ser His Ser
    1105                1110                1115

GAA GAT GAA TGC CTG CAC TTT AAG ATT CTC AAG CAT TTT GAA GTT GGC       3407
Glu Asp Glu Cys Leu His Phe Lys Ile Leu Lys His Phe Glu Val Gly
1120                1125                1130                1135

TTC ATT CAG CCA GGA TCA GTC AAG GTG TAC AGC TAC TAC AAT CTA GAT       3455
Phe Ile Gln Pro Gly Ser Val Lys Val Tyr Ser Tyr Tyr Asn Leu Asp
                1140                1145                1150

GAA AAA TGT ACC AAG ATC TAC CAT CCA GAT GAA GCA ACA GGC CTT CTC       3503
Glu Lys Cys Thr Lys Ile Tyr His Pro Asp Glu Ala Thr Gly Leu Leu
            1155                1160                1165

AAT AAG ATA TGT GTT GGT AAC GTT TGC CGA TGT GCA GAA GAA ACC TGT       3551
Asn Lys Ile Cys Val Gly Asn Val Cys Arg Cys Ala Glu Glu Thr Cys
        1170                1175                1180

TCC TTG CTC AAC CAG CAG AAG AAT GTT ACT CGG CAA TTG CGA ATT CAG       3599
Ser Leu Leu Asn Gln Gln Lys Asn Val Thr Arg Gln Leu Arg Ile Gln
    1185                1190                1195

AAA GCC TTC GAT CCA AAT GTG GAT TAT GTC TAT AAA ACC AAG CTG CTT       3647
Lys Ala Phe Asp Pro Asn Val Asp Tyr Val Tyr Lys Thr Lys Leu Leu
1200                1205                1210                1215

CGA ATA GAA GAA AAA GAT GGT AAT GAT ATC TAT GTC ATG GAC GTT TTA       3695
Arg Ile Glu Glu Lys Asp Gly Asn Asp Ile Tyr Val Met Asp Val Leu
                1220                1225                1230

GAA GTT CTT AAA CAA GGC ACT GAC CAA AAT CAA CAA GTA AAG GTC CGC       3743
Glu Val Leu Lys Gln Gly Thr Asp Gln Asn Gln Gln Val Lys Val Arg
            1235                1240                1245

CAG TAT GTA AGT CAA AGG AAA TGC CAG GAG GCT TTG AAT CTG ATG GTG       3791
Gln Tyr Val Ser Gln Arg Lys Cys Gln Glu Ala Leu Asn Leu Met Val
        1250                1255                1260
```

```
AAT  AAT  GAT  TAT  CTG  ATC  TGG  GGT  CCA  AGC  AGT  GAC  CTG  TGG  CCC  ATG          3839
Asn  Asn  Asp  Tyr  Leu  Ile  Trp  Gly  Pro  Ser  Ser  Asp  Leu  Trp  Pro  Met
          1265               1270                    1275

AAA  GAT  AAA  ATT  TCC  TAT  CTC  ATT  ACA  AAG  AAC  ACC  TGG  ATT  GAG  AGA          3887
Lys  Asp  Lys  Ile  Ser  Tyr  Leu  Ile  Thr  Lys  Asn  Thr  Trp  Ile  Glu  Arg
1280                    1285                    1290                    1295

TGG  CCA  CAT  GAA  GAC  AAA  TGT  CAG  GAA  GAA  GAA  TTC  CAA  AAG  TTG  TGT          3935
Trp  Pro  His  Glu  Asp  Lys  Cys  Gln  Glu  Glu  Glu  Phe  Gln  Lys  Leu  Cys
               1300                    1305                    1310

GAT  GAC  TTT  GCT  CTG  TTT  AGC  TAC  GCA  ATG  AGT  TTG  CTG  CCC  TAC  TTA          3983
Asp  Asp  Phe  Ala  Leu  Phe  Ser  Tyr  Ala  Met  Ser  Leu  Leu  Pro  Tyr  Leu
               1315                    1320                    1325

AAA  GTT  CAG  AAT  AAT  CAA  TGATAGGAAG  GAAATTCTCA  GAAGACAGAT                        4031
Lys  Val  Gln  Asn  Asn  Gln
               1330

TTTTGAGCCA  ATACATATAT  GTTACTTTGT  CTCTTAATTT  TTTAGTTTTC  TGTCATTTGC                  4091

TGTGCTGTTT  TCCCTTAAAT  TGTTTATACA  TAGAATAAAT  GGAATTC                                 4138
```

( 2 ) INFORMATION FOR SEQ ID NO:76:

( i ) SEQUENCE CHARACTERISTICS:
    ( A ) LENGTH: 1333 amino acids
    ( B ) TYPE: amino acid
    ( D ) TOPOLOGY: linear ( i i ) MOLECULE TYPE: protein ( x i ) SEQUENCE DESCRIPTION: SEQ ID NO:76:

```
Ile  Pro  Ser  Gly  Gly  Asp  Met  Val  Met  Thr  Glu  Gln  Ser  Gly  Ile  His
 1                   5                    10                       15

Ile  Val  Thr  Ser  Pro  Tyr  Gln  Ile  Tyr  Phe  Thr  Lys  Thr  Pro  Lys  Tyr
               20                    25                       30

Phe  Lys  Pro  Gly  Met  Pro  Tyr  Glu  Leu  Thr  Val  Tyr  Val  Thr  Lys  Pro
          35                    40                       45

Asp  Gly  Ser  Pro  Ala  Ala  His  Val  Pro  Val  Val  Ser  Glu  Ala  Ile  His
     50                    55                       60

Ser  Glu  Gly  Thr  Thr  Leu  Ser  Asp  Gly  Thr  Ala  Lys  Leu  Phe  Leu  Asn
65                       70                       75                       80

Thr  Pro  Gln  Asn  Ala  Gln  Ser  Leu  Pro  Ile  Thr  Val  Arg  Thr  Asn  His
                    85                    90                       95

Gly  Asp  Leu  Pro  Arg  Glu  Arg  Gln  Ala  Ile  Lys  Ser  Met  Thr  Ala  Thr
               100                   105                      110

Ala  Tyr  Gln  Thr  Gln  Gly  Gly  Ser  Gly  Asn  Tyr  Leu  His  Val  Ala  Ile
          115                   120                      125

Thr  Ser  Thr  Glu  Ile  Lys  Pro  Gly  Asp  Asn  Leu  Pro  Val  Asn  Phe  Asn
     130                   135                      140

Val  Arg  Gly  Asn  Ala  Asn  Ser  Leu  Asn  Gln  Ile  Lys  Tyr  Phe  Thr  Tyr
145                   150                      155                      160

Leu  Ile  Leu  Asn  Lys  Gly  Lys  Ile  Phe  Lys  Val  Gly  Arg  Gln  His  Arg
               165                   170                      175

Gly  Asp  Gly  Glu  Asn  Leu  Val  Thr  Met  Asn  Leu  His  Ile  Thr  Pro  Asp
               180                   185                      190

Leu  Ile  Pro  Ser  Phe  Arg  Phe  Val  Ala  Tyr  Tyr  Gln  Val  Gly  Asn  Asn
          195                   200                      205

Glu  Ile  Val  Ala  Asp  Ser  Val  Trp  Val  Asp  Val  Lys  Asp  Thr  Cys  Met
     210                   215                      220

Gly  Thr  Leu  Val  Val  Lys  Gly  Ala  Thr  Ser  Arg  Asp  Asn  Arg  Ile  Gln
```

|     |     |     |     |     |     |     |     |     |     |     |     |     |     |     |
| --- | --- | --- | --- | --- | --- | --- | --- | --- | --- | --- | --- | --- | --- | --- |
| 225 |     |     |     |     | 230 |     |     |     |     | 235 |     |     |     | 240 |
| Met | Pro | Gly | Ala | Ala | Met | Lys | Ile | Lys | Leu | Glu | Gly | Asp | Pro | Gly |
|     |     |     |     | Ala |     |     |     | 250 |     |     |     | 255 |     | Ala |
|     |     |     |     | 245 |     |     |     |     |     |     |     |     |     |     |
| Trp | Ile | Gly | Leu | Val | Ala | Val | Asp | Lys | Ala | Glu | Tyr | Val | Leu | Asn | Asp |
|     |     |     | 260 |     |     |     | 265 |     |     |     |     | 270 |     |     |
| Lys | Tyr | Lys | Ile | Ser | Gln | Ala | Lys | Ile | Trp | Asp | Thr | Ile | Glu | Lys | Ser |
|     |     | 275 |     |     |     | 280 |     |     |     |     | 285 |     |     |     |
| Asp | Phe | Gly | Cys | Thr | Ala | Gly | Ser | Gly | Gln | Asn | Asn | Leu | Gly | Val | Phe |
|     | 290 |     |     |     |     | 295 |     |     |     |     | 300 |     |     |     |
| Glu | Asp | Ala | Gly | Leu | Ala | Leu | Thr | Thr | Ser | Thr | Asn | Leu | Asn | Thr | Lys |
| 305 |     |     |     |     | 310 |     |     |     |     | 315 |     |     |     |     | 320 |
| Gln | Arg | Ser | Ala | Ala | Lys | Cys | Pro | Gln | Pro | Ala | Asn | Arg | Arg | Arg |
|     |     |     |     | 325 |     |     |     |     | 330 |     |     |     |     | 335 | Arg |
| Ser | Ser | Val | Leu | Leu | Leu | Asp | Ser | Asn | Ala | Ser | Lys | Ala | Ala | Gln | Phe |
|     |     |     | 340 |     |     |     |     | 345 |     |     |     |     | 350 |     |     |
| Gln | Asp | Gln | Asp | Leu | Arg | Lys | Cys | Cys | Glu | Asp | Gly | Met | His | Glu | Asn |
|     |     |     | 355 |     |     |     |     | 360 |     |     |     |     | 365 |     |     |
| Pro | Met | Gly | His | Thr | Cys | Glu | Lys | Arg | Glu | Lys | Tyr | Ile | Gln | Glu | Gly |
|     | 370 |     |     |     |     | 375 |     |     |     |     | 380 |     |     |     |     |
| Asp | Ala | Cys | Lys | Ala | Ala | Phe | Leu | Glu | Cys | Cys | His | Tyr | Ile | Lys | Gly |
| 385 |     |     |     |     | 390 |     |     |     |     | 395 |     |     |     |     | 400 |
| Ile | Gln | Asp | Asp | Asn | Lys | Arg | Glu | Ser | Glu | Leu | Phe | Leu | Ala | Arg | Ser |
|     |     |     |     | 405 |     |     |     |     | 410 |     |     |     |     | 415 |     |
| Asp | Phe | Glu | Asp | Asp | Leu | Phe | Gly | Glu | Gly | Asn | Ile | Thr | Ser | Arg | Ser |
|     |     |     | 420 |     |     |     |     | 425 |     |     |     |     | 430 |     |     |
| Asp | Phe | Pro | Glu | Ser | Trp | Leu | Trp | Leu | Met | Glu | Gln | Leu | Ser | Glu | His |
|     |     | 435 |     |     |     |     | 440 |     |     |     |     | 445 |     |     |     |
| Pro | Asn | Ser | Lys | Gly | Ile | Ser | Ser | Lys | Ile | Val | Pro | Phe | Tyr | Leu | Arg |
|     | 450 |     |     |     |     | 455 |     |     |     |     | 460 |     |     |     |     |
| Asp | Ser | Ile | Thr | Thr | Trp | Glu | Leu | Leu | Ala | Val | Gly | Leu | Ser | Pro | Thr |
| 465 |     |     |     |     | 470 |     |     |     |     | 475 |     |     |     |     | 480 |
| Lys | Gly | Ile | Cys | Val | Ala | Glu | Pro | Tyr | Glu | Ile | Thr | Val | Met | Lys | Asp |
|     |     |     |     | 485 |     |     |     |     | 490 |     |     |     |     | 495 |     |
| Phe | Phe | Ile | Asp | Leu | Gln | Leu | Pro | Tyr | Ser | Val | Val | Lys | Asn | Glu | Gln |
|     |     |     |     | 500 |     |     |     |     | 505 |     |     |     |     | 510 |     |
| Val | Lys | Ile | Arg | Ala | Val | Leu | Tyr | Asn | Tyr | Ala | Asp | Lys | Asp | Ile | Tyr |
|     |     |     | 515 |     |     |     |     | 520 |     |     |     |     | 525 |     |     |
| Val | Arg | Val | Glu | Leu | Leu | Tyr | Ser | Pro | Ala | Phe | Cys | Ser | Ala | Ser | Thr |
|     | 530 |     |     |     |     | 535 |     |     |     |     | 540 |     |     |     |     |
| Glu | Ser | Gln | Arg | Tyr | Arg | Glu | Gln | Leu | Pro | Ile | Lys | Ala | Leu | Ser | Ser |
| 545 |     |     |     |     | 550 |     |     |     |     | 555 |     |     |     |     | 560 |
| Arg | Ala | Val | Ser | Phe | Val | Ile | Val | Pro | Leu | Glu | Gln | Gly | Leu | His | Asp |
|     |     |     |     | 565 |     |     |     |     | 570 |     |     |     |     | 575 |     |
| Val | Glu | Val | Thr | Ala | Ser | Val | Gln | Gly | Glu | Leu | Met | Ser | Asp | Gly | Val |
|     |     |     | 580 |     |     |     |     | 585 |     |     |     |     | 590 |     |     |
| Lys | Lys | Lys | Leu | Lys | Val | Val | Pro | Glu | Gly | Glu | Trp | Lys | Ser | Ile | Val |
|     |     | 595 |     |     |     |     | 600 |     |     |     |     | 605 |     |     |     |
| Thr | Ile | Ile | Glu | Leu | Asp | Pro | His | Thr | Lys | Gly | Ile | Gly | Gly | Thr | Gln |
|     | 610 |     |     |     |     | 615 |     |     |     |     | 620 |     |     |     |     |
| Val | Glu | Leu | Val | Lys | Ala | Asn | Lys | Leu | Asn | Asp | Arg | Val | Pro | Asp | Thr |
| 625 |     |     |     |     | 630 |     |     |     |     | 635 |     |     |     |     | 640 |
| Glu | Ile | Glu | Thr | Lys | Ile | Thr | Ile | Gln | Gly | Asp | Pro | Val | Ala | Gln | Thr |
|     |     |     |     | 645 |     |     |     |     | 650 |     |     |     |     | 655 |     |

-continued

| | | | | | | | | | | | | | | |
|---|---|---|---|---|---|---|---|---|---|---|---|---|---|---|
|Ile|Glu|Asn|Ser|Ile|Asp|Gly|Ser|Lys|Leu|Asn|His|Leu|Ile|Ile|Thr|
| | | |660| | | |665| | | |670| | | |
|Pro|Phe|Gly|Cys|Gly|Glu|Gln|Asn|Met|Ile|Arg|Met|Thr|Ala|Pro|Val|
| | |675| | | |680| | | | |685| | | |
|Ile|Ala|Thr|Tyr|Tyr|Leu|Asp|Thr|Thr|Gln|Gln|Trp|Glu|Thr|Leu|Gly|
|690| | | | |695| | | | |700| | | | |
|Ile|Asn|Arg|Arg|Thr|Glu|Ala|Val|Asn|Gln|Ile|Met|Thr|Gly|Tyr|Ala|
|705| | | |710| | | |715| | | |720| | | |
|Gln|Gln|Leu|Val|Tyr|Lys|Lys|Ala|Asp|His|Ser|Tyr|Ala|Ala|Phe|Thr|
| | | |725| | | |730| | | |735| | | | |
|Asn|Ser|Ala|Ser|Ser|Ser|Trp|Leu|Thr|Ala|Tyr|Val|Val|Lys|Ile|Phe|
| | |740| | | |745| | | | |750| | | | |
|Ala|Leu|Ala|Ala|Lys|Ile|Val|Lys|Asp|Ile|Asn|His|Glu|Ile|Val|Cys|
| |755| | | | |760| | | | |765| | | | |
|Gly|Gly|Met|Arg|Trp|Leu|Ile|Leu|Asn|Arg|Gln|Arg|Thr|Asp|Gly|Val|
|770| | | | |775| | | | |780| | | | | |
|Phe|Arg|Glu|Asn|Ala|Pro|Val|Leu|Phe|Gly|Thr|Met|Gln|Gly|Gly|Ile|
|785| | | |790| | | | |795| | | | | |800|
|Gln|Gly|Ala|Glu|Pro|Glu|Gly|Ser|Leu|Thr|Ala|Phe|Ile|Leu|Val|Ala|
| | | |805| | | | |810| | | | |815| |
|Leu|Leu|Glu|Ser|Arg|Ser|Ile|Cys|Asn|Ala|Tyr|Ile|Asn|Ile|Leu|Asp|
| | |820| | | |825| | | | |830| | | | |
|Ser|Ser|Ile|Ser|Lys|Ala|Thr|Asp|Tyr|Leu|Leu|Lys|Lys|Tyr|Glu|Lys|
| |835| | | | |840| | | | |845| | | | |
|Leu|Gln|Arg|Pro|Tyr|Thr|Thr|Ala|Leu|Thr|Ala|Tyr|Ala|Leu|Ala|Ala|
|850| | | | |855| | | | |860| | | | | |
|Ala|Glu|Arg|Leu|Asn|Asp|Asp|Arg|Val|Leu|Met|Ala|Ala|Ser|Thr|Gly|
|865| | | |870| | | | |875| | | | | |880|
|Arg|Asn|Arg|Trp|Glu|Glu|Pro|Asn|Ala|His|Thr|His|Asn|Ile|Glu|Gly|
| | | |885| | | | |890| | | | |895| |
|Thr|Ser|Tyr|Ala|Leu|Leu|Ala|Leu|Leu|Lys|Met|Lys|Lys|Phe|Val|Glu|
| | | |900| | | |905| | | | |910| | | |
|Ala|Gly|Pro|Val|Val|Gln|Trp|Leu|Ile|Asp|Gln|Gln|Tyr|Tyr|Gly|Gly|
| | |915| | | | |920| | | | |925| | | |
|Thr|Tyr|Gly|Gln|Thr|Gln|Ala|Thr|Val|Met|Met|Phe|Gln|Ala|Leu|Ala|
| |930| | | | |935| | | | |940| | | | |
|Glu|Tyr|Glu|Ile|Gln|Met|Pro|Thr|His|Lys|Asp|Leu|Asn|Leu|Asp|Ile|
|945| | | | |950| | | | |955| | | | |960|
|Thr|Ile|Glu|Leu|Pro|Asp|Arg|Glu|Val|Pro|Ile|Arg|Tyr|Arg|Ile|Asn|
| | | |965| | | | |970| | | | |975| | |
|Tyr|Glu|Asn|Ala|Leu|Leu|Ala|Gln|Thr|Val|Glu|Thr|Lys|Leu|Asn|Glu|
| | | |980| | | | |985| | | | |990| | |
|Asp|Phe|Thr|Val|Ser|Ala|Ser|Gly|Asp|Gly|Lys|Ala|Thr|Met|Thr|Ile|
| | |995| | | | |1000| | | | |1005| | | |
|Leu|Thr|Val|Tyr|Asn|Ala|Gln|Leu|Arg|Glu|Asp|Ala|Asn|Val|Cys|Asn|
| | |1010| | | | |1015| | | | |1020| | | |
|Lys|Phe|His|Leu|Asp|Val|Ser|Val|Glu|Asn|Val|Gln|Leu|Asn|Leu|Lys|
|1025| | | | |1030| | | | |1035| | | | |1040|
|Glu|Ala|Lys|Gly|Ala|Lys|Gly|Ala|Leu|Lys|Leu|Lys|Ile|Cys|Thr|Arg|
| | | | |1045| | | | |1050| | | | |1055| |
|Tyr|Leu|Gly|Glu|Val|Asp|Ser|Thr|Met|Thr|Ile|Ile|Asp|Val|Ser|Met|
| | | |1060| | | | |1065| | | | |1070| | |
|Leu|Thr|Gly|Phe|Val|Pro|Asp|Thr|Glu|Asp|Leu|Thr|Arg|Leu|Ser|Lys|
| | | |1075| | | | |1080| | | | |1085| | |

Gly Val Asp Arg Tyr Ile Ser Met Phe Glu Ile Asn Asn Met Ala
1090                1095                1100

Gln Lys Gly Thr Val Ile Ile Tyr Leu Asp Lys Val Ser His Ser Glu
1105                1110                1115                1120

Asp Glu Cys Leu His Phe Lys Ile Leu Lys His Phe Glu Val Gly Phe
                    1125                1130                1135

Ile Gln Pro Gly Ser Val Lys Val Tyr Ser Tyr Asn Leu Asp Glu
                1140                1145                1150

Lys Cys Thr Lys Ile Tyr His Pro Asp Glu Ala Thr Gly Leu Leu Asn
                1155                1160                1165

Lys Ile Cys Val Gly Asn Val Cys Arg Cys Ala Glu Glu Thr Cys Ser
        1170                1175                1180

Leu Leu Asn Gln Gln Lys Asn Val Thr Arg Gln Leu Arg Ile Gln Lys
1185                1190                1195                1200

Ala Phe Asp Pro Asn Val Asp Tyr Val Tyr Lys Thr Lys Leu Leu Arg
                1205                1210                1215

Ile Glu Glu Lys Asp Gly Asn Asp Ile Tyr Val Met Asp Val Leu Glu
                1220                1225                1230

Val Leu Lys Gln Gly Thr Asp Gln Asn Gln Val Lys Val Arg Gln
                1235                1240                1245

Tyr Val Ser Gln Arg Lys Cys Gln Glu Ala Leu Asn Leu Met Val Asn
    1250                1255                1260

Asn Asp Tyr Leu Ile Trp Gly Pro Ser Ser Asp Leu Trp Pro Met Lys
1265                1270                1275                1280

Asp Lys Ile Ser Tyr Leu Ile Thr Lys Asn Thr Trp Ile Glu Arg Trp
                1285                1290                1295

Pro His Glu Asp Lys Cys Gln Glu Glu Phe Gln Lys Leu Cys Asp
                1300                1305                1310

Asp Phe Ala Leu Phe Ser Tyr Ala Met Ser Leu Leu Pro Tyr Leu Lys
                1315                1320                1325

Val Gln Asn Asn Gln
        1330

( 2 ) INFORMATION FOR SEQ ID NO:77:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:77:

CGCTCGACCC ACGCGTCCGC CATGGAGAGG ATGGC    35

( 2 ) INFORMATION FOR SEQ ID NO:78:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:78:

CTGCGACGCC TCCGATTTGC AGGC    24

(2) INFORMATION FOR SEQ ID NO:79:

(i) SEQUENCE CHARACTERISTICS:
(A) LENGTH: 25 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:79:

GCATTTTCAT AATTAATTCT GTACC 25

(2) INFORMATION FOR SEQ ID NO:80:

(i) SEQUENCE CHARACTERISTICS:
(A) LENGTH: 41 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:80:

GACTAGTTCT AGATCGCGAG CGGCCGCCCT TTTTTTTTT T 41

(2) INFORMATION FOR SEQ ID NO:81:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:81:

Leu Tyr Asn Val Glu Ala
1               5